United States Patent
Azmi et al.

(10) Patent No.: US 12,286,472 B2
(45) Date of Patent: Apr. 29, 2025

(54) BIOPHARMACEUTICAL COMPOSITIONS AND METHODS FOR PEDIATRIC PATIENTS

(71) Applicant: GLAXOSMITHKLINE INTELLECTUAL PROPERTY (NO.2) LIMITED, Brentford (GB)

(72) Inventors: Jahanara Azmi, Middlesex (GB); Jonathan Steinfeld, Collegeville, PA (US)

(73) Assignee: GlaxoSmithKline Intellectual Property (No.2) Limited (GB)

( * ) Notice: Subject to any disclaimer, the term of this patent is extended or adjusted under 35 U.S.C. 154(b) by 247 days.

(21) Appl. No.: 17/835,321

(22) Filed: Jun. 8, 2022

(65) Prior Publication Data

US 2022/0380451 A1    Dec. 1, 2022

Related U.S. Application Data

(62) Division of application No. 16/619,146, filed as application No. PCT/US2018/031518 on May 8, 2018, now Pat. No. 11,390,671.

(60) Provisional application No. 62/619,206, filed on Jan. 19, 2018, provisional application No. 62/515,641, filed on Jun. 6, 2017.

(51) Int. Cl.
*C07K 16/24* (2006.01)
*A61K 9/00* (2006.01)
*A61P 11/06* (2006.01)

(52) U.S. Cl.
CPC .......... *C07K 16/244* (2013.01); *A61K 9/0019* (2013.01); *A61P 11/06* (2018.01); *C07K 2317/24* (2013.01); *C07K 2317/76* (2013.01); *C07K 2317/94* (2013.01)

(58) Field of Classification Search
CPC .......................................... A61K 2039/55527
See application file for complete search history.

(56) References Cited

U.S. PATENT DOCUMENTS

| | | |
|---|---|---|
| 4,980,359 A | 12/1990 | Hasspacher et al. |
| 5,096,704 A | 3/1992 | Coffman et al. |
| 5,683,892 A | 11/1997 | Ames, Jr. et al. |
| 5,693,323 A | 12/1997 | Ames, Jr. et al. |
| 5,783,184 A | 7/1998 | Appelbaum et al. |
| 5,851,525 A | 12/1998 | Ames, Jr. et al. |
| 5,858,089 A | 1/1999 | Martinovic |
| 6,248,723 B1 | 6/2001 | Irvin |
| 6,555,566 B2 | 4/2003 | Ponikau |
| 2003/0059429 A1 | 3/2003 | Ames et al. |
| 2003/0194404 A1 | 10/2003 | Greenfeder et al. |
| 2006/0029594 A1 | 2/2006 | Ames et al. |
| 2009/0035216 A1 | 2/2009 | Svenson et al. |
| 2010/0006554 A1 | 1/2010 | Inoue et al. |
| 2010/0086547 A1 | 4/2010 | Patel et al. |
| 2014/0044717 A1 | 2/2014 | Kranz et al. |
| 2014/0044727 A1 | 2/2014 | Monck et al. |
| 2016/0096886 A1 | 4/2016 | Patel et al. |
| 2016/0207993 A1 | 7/2016 | Ashman et al. |
| 2018/0022799 A1 | 1/2018 | Patel et al. |
| 2020/0040073 A1 | 2/2020 | Patel et al. |

FOREIGN PATENT DOCUMENTS

| | | |
|---|---|---|
| EP | 0367596 A1 | 5/1990 |
| JP | 06141885 | 5/1994 |
| JP | 2000515494 A | 11/2000 |
| WO | 1993015210 A1 | 8/1993 |
| WO | 1993016184 A1 | 8/1993 |
| WO | 1995035375 A1 | 12/1995 |
| WO | 1997048418 A1 | 12/1997 |
| WO | 2008134721 A1 | 11/2008 |
| WO | 2008134724 A3 | 2/2009 |
| WO | 2014141149 A1 | 9/2014 |
| WO | 2017033121 A1 | 3/2017 |

OTHER PUBLICATIONS

Choy, Min Sung et al: "Mepolizumab (Nucala) for severe Eosinophilic Asthma", Pharmacy and Therapeutics (PT), vol. 41, No. 10, Oct. 1, 2016, pp. 619-622, XP055815969, pp. 619-620.
Deeks E D: "Mepolizumab: A review in Eosinophilic Asthma", Biodrugs, Adis International Ltd, NZ. vol. 30, No. 4; Aug. 1, 2016, pp. 361-370, XP009509648, ISSN: 1173-8804, DOI: 10.1007/S40259-016-0182-5, abstract, pp. 362-367.
NCT00358449 May 1, 2007.
NCT00358449 Aug. 17 2007.
NCT00358449 Nov. 9, 2007.
NCT00358449 Feb. 28, 2008.
U.S. Appl. No. 60/914,833.
U.S. Appl. No. 60/990,715.
Assa'Ad et al., "An Antibody Against IL-5 Reduces Numbers of Esophageal Intraepithelial Eosinophils in Children With Eosinophilic Esophagitis", Gastroenterology, Elsevier Inc, US, vol. 141, No. 5, Jul. 19, 2011 (Jul. 19, 2011), pp. 1593-1604.
Assa'Ad et al., The Pharmacodynamic Effects of Mepolizumab, A Humanized Monoclonal Antibody Against IL-5, in Pediatric Patients with EE: A Randomized, Double-blind, Controlled Clinical Trial, AAAAI (2010) American Academy of Allergy, Asthma & Immunology—66th Annual Meeting (Poster presentation), 2010.
Assa'Ad et al., The Pharmacodynamic Effects of Mepolizumab, A Humanized Monoclonal Antibody Against IL-5, in Pediatric Patients with EE: A Randomized, Double-blind, Controlled Clinical Trial, AAAAI (2010) American Academy of Allergy, Asthma & Immunology—66th Annual Meeting, J Allergy Clin Immunol 2010; 125 (2): AB129 [Abstract 510].
Chee Ng, et al., Rationale for Fixed Dosing of Pertuzumab in Cnacer Patients Based on Population Phamacokinetic Analysis., Pharma. reserch, vol. 23, No. 6, pp. 1275-1284, 2006.

(Continued)

*Primary Examiner* — Prema M Mertz
(74) *Attorney, Agent, or Firm* — Cynthia Lan Martin

(57) ABSTRACT

The present disclosure relates to compositions, for treating interleukin 5 (IL-5) mediated diseases in pediatric subjects, and related methods.

13 Claims, 5 Drawing Sheets
Specification includes a Sequence Listing.

(56) References Cited

OTHER PUBLICATIONS

Collins, et al., A Monoclonal Antibody (Mepolizumab) Against Interleukin-5 (IL-5) Significantly Reduces Eosinophilic Inflammation in Eosinophilic Esophagitis (EoE) in Children, SPP (2010) Society for Pediatric Pathology—2010 Spring Meeting.
Collins, et al., A Monoclonal Antibody (Mepolizumab) Against Interleukin-5 (IL-5) Significantly Reduces Eosinophilic Inflammation in Eosinophilic Esophagitis (EoE) in Children, SPP (2010) Society for Pediatric Pathology—2010 Spring Meeting (Oral Presentation).
Gnanakumaran Gnanasegaram, et al., Technology evaluation: mepolizumab, "GlaxoSmithKline", Current Opinion in Molecular Therapeutics, Current Drugs, vol. 5, No. 3, pp. 321-325, Jun. 1, 2003.
Gunaratna, C., Drug Metabolism and Pharmacokinetics in Drug Discovery: A primer For Bioanalytical Chemists, Part II. Current Seperations 19:3(2001), pp. 87-92.
Gupta, et al., PK and PD of Mepolizumab in Pediatric Subjects with Eosinophilic Esophagitis: A Randomized, Double-blind Controlled Clinical Trial, NASPGHAN (2009) North American Society for Pediatric Gastroenterology, Hepatology, and Nutrition 22nd Annual Meeting, J Pediatr Gastroenterol Nutr 2009; 49 (Suppl 1): E65-66 [abstract 147].
Gupta, et al., PK and PD of Mepolizumab in Pediatric Subjects with Eosinophilic Esophagitis: A Randomized, Double-blind Controlled Clinical Trial, NASPGHAN (2009) North American Society for Pediatric Gastroenterology, Hepatology, and Nutrition 22nd Annual Meeting, (Oral Presentation).
Gurney, Howard, Dose Calculation of Anticancer Drugs: J. Clin. Oneal., vol. 14, No. 9, Sep. 1996: pp. 2590-2611.
Hart Timothy K, et al., Preclinical eficiacy and safety of mepolizumab (SB-240563) a humanized monoclonal antibody to IL-5, in cynomolgus monkeys., Journal of Allergy and Clinical Immunoloov, vol. 108, No. 2, pp. 250-257, Aug. 2001.
Garrett, et al., Journal Allergy Clin Immunol, 2004, vol. 113, No. 1, pp. 115-119.
Mathijssen, et al., "Flat-Fixed Dosing Versus Body Surface Area-Based Dosing of Anticancer Drugs in Adults", The Oncologist, 2007; 12:913-923 www.TheOncologist.com.
Mehr, et al., Treatment of a Case of Pediatric Hypereosinophilic Syndrome with Anti-interleukin-5, J Pediatr 2009; 155 (2): 289-291.
NCT00358449 Jul. 28, 2006.
NCT00358449 Sep. 22, 2006.
Ortega, et al., "Mepolizumab Treatment in Patients with Severe Eosinophilic Asthma", The New England Journal of Medicine, vol. 371, No. 13, Sep. 25, 2014 (Sep. 25, 2014), pp. 1198-1207.
Ortega, et al., Pharmacokinetics and absolute bioavailability of mepolizumab following administration at subcutaneous and intramuscular sites, Clin Pharmacol Drug Devel., Clin Pharmacol Drug Devel. 2013; 3(1):57-62 (Primary Manuscript).
Rothenberg, et al., Mar. 2008, The New England Journal of Medicine, vol. 358, No. 12, pp. 1215-1228.
Smith, et al., Pharmacokinetics and Pharmacodynamics of Mepolizumab, an Anti-Interleukin-5 Monoclonal Antibody. Clin. Pharmacokinet. 2011; 50(4):215-227.
Takanaka, "About clinical pharmacokinetic studies of drugs", JPN Journal Clin. Pharmacol. Ther., 2001, vol. 32, No. 5, pp. 217-222.
Thomson, et al., Safety and PD of Mepolizumab, a Humanised Monoclonal Antibody Against IL-5, in Paediatric Subjects with Eosinophilic Oesophagitis: A Randomised, Double-blind Controlled Clinical Trial, UEGW (2009) United European Gastroenterology Week—17th Annual Conference (See WCOG).
Thomson, et al., Safety and PD of Mepolizumab, a Humanised Monoclonal Antibody Against IL-5, in Paediatric Subjects with Eosinophilic Oesophagitis: A Randomised, Double-blind Controlled Clinical Trial, UEGW (2009) United European Gastroenterology Week—17th Annual Conference (See WCOG), (Oral Presentation).
Tsukamoto, et al., Pharmacokinetics and pharmacodynamics of mepolizumab, an anti-interleukin-5 monoclonal antibody, in healthy Japanese male subjects, Clin Pharmacol Drug Devel., Clin Pharmacol Drug Devel. 2016;5 (2):105-108 (Primary Manuscript).
Wang, et al., Fixed Dosing Versus Body-Based Dosing of Monoclonal Antibodies in Adult Clinical Trials. J. Clin. Pharmacol., 2009 49:1012.
Zia-Amirhosseini, et al., Pharmacokinetics and pharmacodynamics of SB-240563, a humanized monoclonal antibody directed to human interleukin-5, in mild asthmatics., Clinical Pharmacoloov and Therapeutics, vol. 65, No. 2, p. 147,Feb. 1, 1999.
Zia-Amirhosseini, et al., Pharmacokinetics and pharmacodynamics of SB-240563, a humanized monoclonal antibody directed to human interleukin-5, in monkeys, Journal of Pharmacology and Experimental Therapeutics, vol. 291, No. 3, pp. 1060-1067, Dec. 1999.
Bai, et al., A Guide to Rational Dosing of Monoclonal Antibodies. Clin. Pharmacokinet 2012; 51 (2): 119-135.
Greenfeder, et al., "Th2 cytokines and asthma—The role of interleukin-5 in allergic eosinophilic disease", Respiratory Research, Biomed Central Ltd., London, GB, vol. 2, No. 2, Mar. 8, 2001 (Mar. 8, 2001), pp. 71-79.
Revill, P., et al., Mepolizumab. Humanized anti-IL-5 monoclonal antibody, Treatment of hypereosinophilic syndromes, Drugs of the Future, vol. 32, No. 10, pp. 868-876, Oct. 2007.
NCT00266565 Dec. 16, 2005.
NCT00266565 Dec. 19, 2005.
NCT00266565 Dec. 28, 2005.
NCT00266565 May 26, 2006.
NCT00266565 Jun. 21, 2006.
NCT00266565 Jun. 27, 2006.
NCT00266565 Dec. 14, 2006.
NCT00266565 Jan. 23, 2007.
NCT00266565 Jan. 29, 2007.
NCT00266565 Feb. 5, 2007.
NCT00266565 Sep. 13, 2007.
NCT00266565 Apr. 3, 2008.
NCT00358449 Dec. 21, 2006.
NCT00358449 Feb. 6, 2007.
NCT00358449 Mar. 18, 2007.
NCT00358449 Mar. 28, 2007.
NCT00358449 Apr. 19, 2007.

FIG. 4

| BODY SURFACE AREA | | | |
|---|---|---|---|
| • %BSA AREA SCORE MAY BE DETERMINED BY FOLLOWING THE 3 STEPS DESCRIBED HERE TO CALCULATE TOTAL % BSA INVOLVEMENT. | | | |
| • STEP 1: ESTIMATE %BSA INVOLVEMENT IN EACH BODY REGION; STEP 2: MULTIPLY % INVOLVEMENT BY FRACTION OF TOTAL BODY AREA; STEP 3: CALCULATE THE TOTAL INVOLVED %BSA. THE AN EXAMPLE OF HOW % TOTAL INVOLVED BSA MAY BE CALCULATED IS PROVIDED BELOW: | | | |
| BODY REGION | % INVOLVEMENT (0-100% EACH AREA) | % INVOLVEMENT X PROPORTIONALITY MULTIPLIER | REGIONAL % BSA INVOLVEMENT |
| HEAD AND NECK | | ........ X 0.1 | |
| UPPER EXTREMITIES | | ........ X 0.2 | |
| TRUNK | | ........ X 0.3 | |
| LOWER EXTREMITIES | | ........ X 0.4 | |
| TOTAL INVOLVED % BSA (SUM OF THE 4 AREA VALUES) * | | | |

FIG. 5

| ECZEMA AREA AND SEVERITY INDEX (EASI) |
|---|

ONCE A % BSA INVOLVEMENT FOR EACH REGION IS DETERMINED, EACH PERCENTAGE IS TRANSLATED TO AN AREA SCORE BASED ON THE FOLLOWING DEFINITIONS:

0 = NO INVOLVEMENT
1 = <10%
2 = 10% - 29%
3 = 30% - 49%
4 = 50% - 69%
5 = 70% - 89%
6 = 90% - 100%

SEVERITY OF SIGNS: GRADE THE SEVERITY OF EACH SIGN ON A SCALE OF 0 TO 3:

✓ TAKE AN AVERAGE OF THE SEVERITY ACROSS THE INVOLVED AREA
✓ HALF-POINTS MAY BE USED, E.G., 2.5

| 0 | ABSENT |
|---|---|
| 1 | MILD |
| 2 | MODERATE |
| 3 | SEVERE |

SCORING TABLE:

| BODY REGION | ERYTHEMA (0-3) | INDURATION/ PAPULATION (0-3) | EXCORIATION (0-3) | LICHENIFICATION (0-3) | REGION SCORE (0-6) | MULTIPLIER | SCORE PER BODY REGION |
|---|---|---|---|---|---|---|---|
| HEAD/NECK | ( + | + | + | ) | X | X 0.1 | |
| TRUNK | ( + | + | + | ) | X | X 0.3 | |
| UPPER EXTREMITIES | ( + | + | + | ) | X | X 0.2 | |
| LOWER EXTREMITIES | ( + | + | + | ) | X | X 0.4 | |
| | | | | THE FINAL EASI SCORE IS THE SUM OF THE 4 REGION SCORES: | | | (0-72) |

BIOPHARMACEUTICAL COMPOSITIONS AND METHODS FOR PEDIATRIC PATIENTS

CROSS REFERENCE TO RELATED APPLICATIONS

This application is a Divisional of U.S. application Ser. No. 16/619,146 filed Dec. 4, 2019, which is a 371 of International Application No. PCT/US2018/031518 filed May 8, 2018, which claims the benefit of U.S. Provisional Application No. 62/619,206 filed Jan. 19, 2018, and U.S. Provisional Application No. 62/515,641 filed Jun. 6, 2017, the disclosures of which are incorporated herein in their entireties.

FIELD OF THE DISCLOSURE

The present disclosure relates to compositions, for treating interleukin 5 (IL-5) mediated diseases, and related methods in pediatric patients.

BACKGROUND OF THE DISCLOSURE

IL-5 a secreted protein. IL-5 plays a role in a number of different diseases such as asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis. These serious diseases affect hundreds of millions of people, including pediatric patients, world wide.

This means a need exists for compositions suitable for treating IL-5 mediated disease in pediatric patients. Such compositions and related methods are provided by the present disclosure.

SUMMARY OF THE DISCLOSURE

One aspect of the disclosure is a method of treating a disease in a pediatric subject comprising the steps of: a) identifying a pediatric subject weighing less than 40 kg with a disease selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis; and b) administering a therapeutically effective amount of an antibody comprising the heavy chain amino acid sequence shown in SEQ ID NO: 1 and the light chain amino acid sequences shown in SEQ ID NO: 2 subcutaneously to the pediatric subject wherein the therapeutically effective amount of the antibody provides a maximum plasma concentration (Cmax) of the antibody that is about 10.1960±0.3345 µg/mL and an Area Under the Curve [0-infinity] value that is about 454.39±15.8876 µg*day/mL; whereby the disease in the pediatric subject is treated.

Another aspect of the disclosure is a method of treating a disease in a pediatric subject comprising the steps of: a) identifying a pediatric subject weighing greater than or equal to 40 kg with a disease selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis; and b) administering a therapeutically effective amount of an antibody comprising the heavy chain amino acid sequence shown in SEQ ID NO: 1 and the light chain amino acid sequences shown in SEQ ID NO: 2 subcutaneously to the pediatric subject wherein the therapeutically effective amount of the antibody provides a maximum plasma concentration (Cmax) of the antibody that is about 16.3412±0.6364 µg/mL and an Area Under the Curve [0-infinity] value that is about 675.20±35.8980 µg*day/mL; whereby the disease in the pediatric subject is treated.

Another aspect of the disclosure is a method of decreasing an absolute blood eosinophil count in a pediatric subject comprising the steps of: a) identifying a pediatric subject weighing less than 40 kg having a condition selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis and atopic dermatitis; and b) administering a therapeutically effective amount of an antibody comprising the heavy chain amino acid sequence shown in SEQ ID NO: 1 and the light chain amino acid sequences shown in SEQ ID NO: 2 subcutaneously to the pediatric subject wherein the therapeutically effective amount of the antibody provides a maximum plasma concentration (Cmax) of the antibody that is about 10.1960±0.3345 µg/mL and an Area Under the Curve [0-infinity] value that is about 454.39±15.8876 µg*day/mL; whereby the absolute blood eosinophil count in the pediatric subject is decreased.

Another aspect of the disclosure is a method of decreasing an absolute blood eosinophil count in a pediatric subject comprising the steps of: a) identifying a pediatric subject weighing greater than or equal to 40 kg having a condition selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis and atopic dermatitis; and b) administering a therapeutically effective amount of an antibody comprising the heavy chain amino acid sequence shown in SEQ ID NO: 1 and the light chain amino acid sequences shown in SEQ ID NO: 2 subcutaneously to the pediatric subject wherein the therapeutically effective amount of the antibody provides a maximum plasma concentration (Cmax) of the antibody that is about 16.3412±0.6364 µg/mL and an Area Under the Curve [0-infinity] value that is about 675.20±35.8980 µg*day/mL; whereby the absolute blood eosinophil count in a pediatric subject is decreased.

Another aspect of the disclosure is a composition for treating a disease selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis in a pediatric subject weighing less than 40 kg wherein said composition comprises an antibody comprising the heavy chain amino acid sequence shown in SEQ ID NO: 1 and the light chain amino acid sequences shown in SEQ ID NO: 2 and a therapeutically effective amount of the antibody administered subcutaneously to the pediatric subject provides a maximum plasma concentration (Cmax) of the antibody that is about 10.1960±0.3345 µg/mL and an Area Under the Curve [0-infinity] value that is about 454.39±15.8876 µg*day/mL.

Another aspect of the disclosure is a composition for treating a disease selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis in a pediatric subject weighing greater than or equal to 40 kg wherein said composition comprises an antibody comprising the heavy chain amino acid sequence shown in SEQ ID NO: 1 and the light chain amino acid sequences shown in SEQ ID NO: 2 and a therapeutically effective amount of the antibody administered subcutaneously to the pediatric subject provides a maximum plasma concentration (Cmax) of the antibody that is about 16.3412±0.6364 µg/mL and an Area Under the Curve [0-infinity] value that is about 675.20±35.8980 µg*day/mL.

Another aspect of the disclosure is a composition for decreasing an absolute blood eosinophil count in a pediatric subject weighing less than 40 kg, wherein said pediatric subject has a disease selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis; and said composition comprises an antibody comprising the heavy chain amino acid sequence shown in SEQ ID NO: 1 and the light chain amino acid sequences shown in SEQ ID NO: 2; and a therapeutically effective amount of the antibody administered subcutaneously to the pediatric subject provides a maximum plasma concentration (Cmax) of the antibody that is about 10.1960±0.3345 µg/mL and an Area Under the Curve [0-infinity] value that is about 454.39±15.8876 µg*day/mL.

Another aspect of the disclosure is a composition for decreasing an absolute blood eosinophil count in a pediatric subject weighing greater than or equal to 40 kg, wherein said pediatric subject has a disease selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis; and said composition comprises an antibody comprising the heavy chain amino acid sequence shown in SEQ ID NO: 1 and the light chain amino acid sequences shown in SEQ ID NO: 2; and a therapeutically effective amount of the antibody provides a maximum plasma concentration (Cmax) of the antibody that is about 16.3412±0.6364 µg/mL and an Area Under the Curve [0-infinity] value that is about 675.20±35.8980 m*day/mL.

BRIEF DESCRIPTION OF THE DRAWINGS

FIG. 4. Body Surface Area.

FIG. 5. Eczema Area and Severity Index (EASI).

DETAILED DESCRIPTION OF THE DISCLOSURE present disclosure provides compositions and methods, for treating interleukin 5 (IL-5) mediated diseases in pediatric patients, and related subject matter.

The term "asthma" as used herein means an inflammatory disease of the airways characterized by reversible airflow obstruction and bronchospasm. Common symptoms include wheezing, coughing, chest tightness, and shortness of breath. Asthma is a heterogeneous disease, usually characterized by chronic airway inflammation. It is defined by the history of respiratory symptoms such as wheeze, shortness of breath, chest tightness and cough that vary over time and in intensity, together with variable expiratory airflow limitation.

Figure 1:
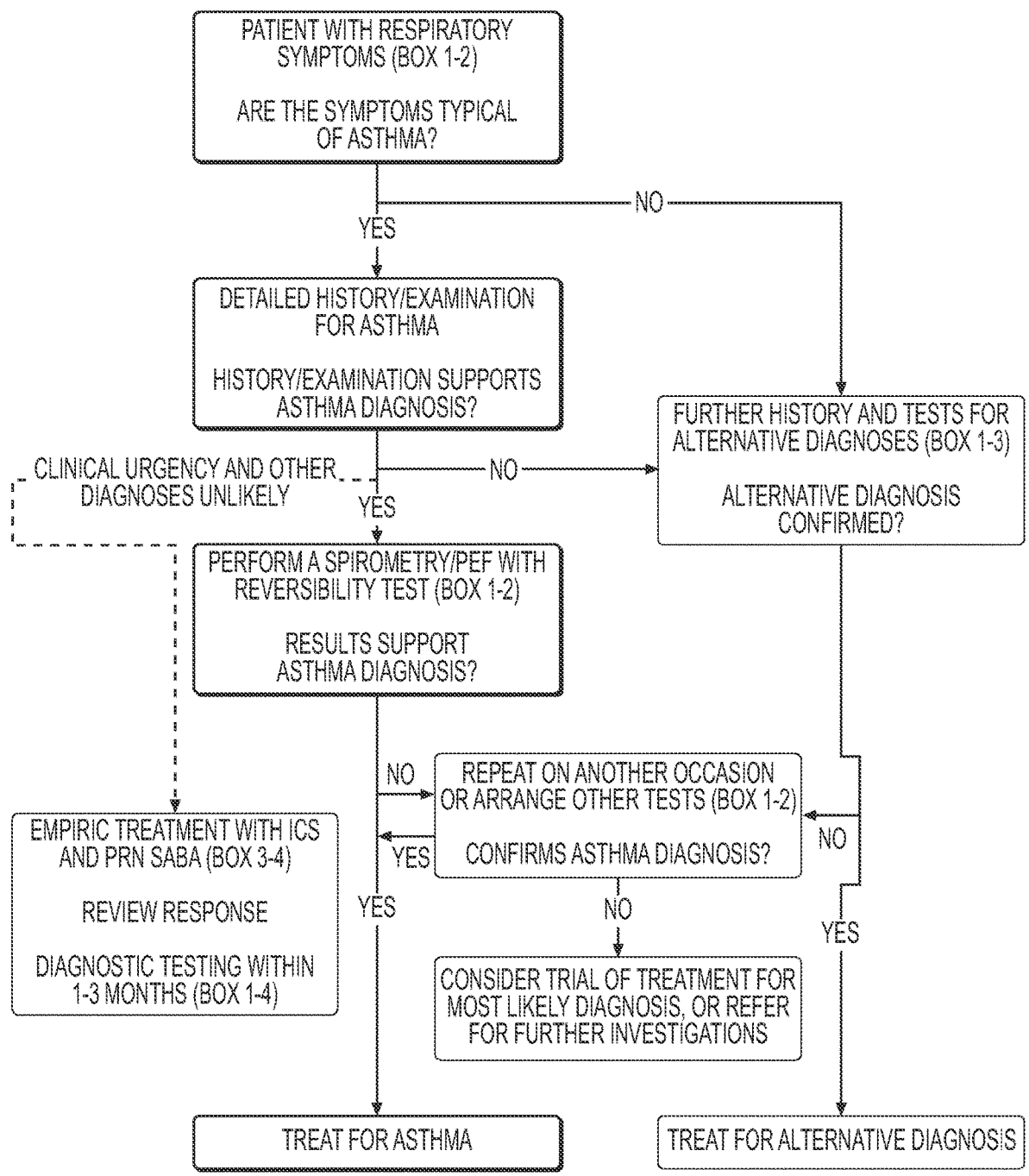
FIG. 1. Box 1-1. Diagnostic flowchart for clinical practice—initial presentation.

In the methods of the disclosure a diagnosis of asthma in a subject may be made according to the guidance provided by the Global Initiative for Asthma (GINA) the Global Strategy for Asthma Management and Prevention (2016 update) document. Those of ordinary skill in the art will be familiar with the GINA diagnostic flow chart for clinical practice (FIG. 1) and diagnostic criteria for asthma in adults, adolescents and children 6-11 years (Table 1) shown below as well as other aspect of the guidance (e.g., for pregnant women etc.). See also Table 2 and Table 3.

TABLE 1

| Box 1-2. Diagnostic criteria for asthma in adults, adolescents, and children 6-11 years. Asthma is a heterogeneous disease, usually characterized by chronic airway inflammation. It is defined by the history of respiratory symptoms such as wheeze, shortness of breath, chest tightness and cough that vary over time and in intensity, together with variable expiratory airflow limitation. ||
|---|---|
| DIAGNOSTIC FEATURE | DIAGNOSTIC FEATURE |
| 1. History of variable respiratory symptoms ||
| Wheeze, shortness of breath, chest tightness and cough<br>Descriptors may vary between cultures and by age, e.g. children may be described as having heavy breathing | Generally more than one type of respiratory symptom (in adults, isolated cough is seldom due to asthma)<br>Symptoms occur variably over time and vary in intensity<br>Symptoms are often worse at night or on waking<br>Symptoms are often triggered by exercise, laughter, allergens, cold air<br>Symptoms often appear or worsen with viral infections |
| 2. Confirmed variable expiratory airflow limitation ||
| Documented excessive variability in lung function* (one or more of the tests below) AND documented airflow limitation* | The greater the variations, or the more occasions excess variation is seen, the more confident the diagnosis<br>At least once during diagnostic process when FEV1 is low, confirm that FEV1/FVC is reduced (normally >0.75-0.80 in adults, >0.90 in children) |
| Positive bronchodilator (BD) reversibility test* (more likely to be positive if BD medication is withheld before test: SABA ≥4 hours, LABA ≥15 hours) | Adults: increase in FEV1 of >12% and >200 mL from baseline, 10-15 minutes after 200-400 mcg albuterol or equivalent (greater confidence if increase is >15% and >400 mL).<br>Children: increase in FEV1 of >12% predicted |
| Excessive variability in twice-daily PEF over 2 weeks* | Adults: average daily diurnal PEF variability >10%<br>Children: average daily diurnal PEF variability >13% |
| Significant increase in lung function after 4 weeks of anti-inflammatory treatment | Adults: increase in FEV1 by >12% and >200 mL (or PEF† by >20%) from baseline after 4 weeks of treatment, outside respiratory infections |
| Positive exercise challenge test* | Adults: fall in FEV1 of >10% and >200 mL from baseline<br>Children: fall in FEV1 of >12% predicted, or PEF >15% |
| Positive bronchial challenge test (usually only performed in adults) | Fall in FEV1 from baseline of ≥20% with standard doses of methacholine or histamine, or ≥15% with standardized hyperventilation, hypertonic saline or mannitol challenge |
| Excessive variation in lung function between visits* (less reliable) | Adults: variation in FEV1 of >12% and >200 mL between visits, outside of respiratory infections<br>Children: variation in FEV1 of >12% in FEV1 or >15% in PEF† between visits (may include respiratory infections) |

BD: bronchodilator (short-acting SABA or rapid-acting LABA); FEV1: forced expiratory volume in 1 second; LABA: long-acting beta2-agonist; PEF: peak expiratory flow (highest of three readings); SABA: short-acting beta2-agonist. See Box 1-4 for diagnosis in patients already taking controller treatment.
*These tests can be repeated during symptoms or in the early morning.
**Daily diurnal PEF variability is calculated from twice daily PEF as ([day's highest minus day's lowest]/mean of day's highest and lowest), and averaged over one week.
†For PEF, use the same meter each time, as PEF may vary by up to 20% between different meters. BD reversibility may be lost during severe exacerbations or viral infections. If bronchodilator reversibility is not present at initial presentation, the next step depends on the availability of other tests and the urgency of the need for treatment. In a situation of clinical urgency, asthma treatment may be commenced and diagnostic testing arranged within the next few weeks (Box 1-4), but other conditions that can mimic asthma (Box 1-3) should be considered, and the diagnosis of asthma confirmed as soon as possible.

TABLE 2

Box 1-3. Differential diagnosis of asthma in adults, adolescents and children 6-11 years.

| Age | Condition | Symptoms |
|---|---|---|
| 6-11 years | Chronic upper airway cough syndrome | Sneezing, itching, blocked nose, throat-clearing |
| | Inhaled foreign body | Sudden onset of symptoms, unilateral wheeze |
| | Bronchiectasis | Recurrent infections, productive cough |
| | Primary ciliary dyskinesia | Recurrent infections, productive cough, sinusitis |
| | Congenital heart disease | Cardiac murmurs |
| | Bronchopulmonary dysplasia | Pre-term delivery, symptoms since birth |
| | Cystic fibrosis | Excessive cough and mucus production, gastrointestinal symptoms |
| 12-39 years | Chronic upper airway cough syndrome | Sneezing, itching, blocked nose, throat-clearing |
| | Vocal cord dysfunction | Dyspnea, inspiratory wheezing (stridor) |
| | Hyperventilation, dysfunctional breathing | Dizziness, paresthesia, sighing |
| | Bronchiectasis | Productive cough, recurrent infections |
| | Cystic fibrosis | Excessive cough and mucus production |
| | Congenital heart disease | Cardiac murmurs |
| | Alpha1-antitrypsin deficiency | Shortness of breath, family history of early emphysema |
| | Inhaled foreign body | Sudden onset of symptoms |
| 40+ years | Vocal cord dysfunction | Dyspnea, inspiratory wheezing (stridor) |
| | Hyperventilation, dysfunctional breathing | Dizziness, paresthesia, sighing |
| | COPD* | Cough, sputum, dyspnea on exertion, smoking or noxious exposure |
| | Bronchiectasis | Productive cough, recurrent infections |
| | Cardiac failure | Dyspnea with exertion, nocturnal symptoms |
| | Medication-related cough | Treatment with angiotensin converting enzyme (ACE) inhibitor |
| | Parenchymal lung disease | Dyspnea with exertion, non-productive cough, finger clubbing |
| | Pulmonary embolism | Sudden onset of dyspnea, chest pain |
| | Central airway obstruction | Dyspnea, unresponsive to bronchodilators |

*Any of the above conditions may also contribute to respiratory symptoms in patients with confirmed asthma.

TABLE 3

Box 1-4. Confirming the diagnosis of asthma in a patient already taking controller treatment.

| Current status | Steps to confirm the diagnosis of asthma |
|---|---|
| Variable respiratory symptoms and variable airflow limitation | Diagnosis of asthma is confirmed. Assess the level of asthma control and review controller treatment. |
| Variable respiratory symptoms but no variable airflow limitation | Repeat BD reversibility test again after withholding BD (SABA: 4 hours; LABA: 12+ hours) or during symptoms. If normal, consider alternative diagnoses (Box 1-3). If FEV1 is >70% predicted: consider a bronchial provocation test. If negative, consider stepping down controller treatment and reassess in 2-4 weeks. If FEV1 is <70% predicted: consider stepping up controller treatment for 3 months, then reassess symptoms and lung function. If no response, resume previous treatment and refer patient for diagnosis and investigation |
| Few respiratory symptoms, normal lung function, and no variable airflow limitation | Repeat BD reversibility test again after withholding BD (SABA: 4 hours; LABA: 12+ hours) or during symptoms. If normal, consider alternative diagnoses (Box 1-3). Consider stepping down controller treatment: If symptoms emerge and lung function falls: asthma is confirmed. Step up controller treatment to lowest previous effective dose. If no change in symptoms or lung function at lowest controller step: consider ceasing controller, and monitor patient closely for at least 12 months. |

TABLE 3-continued

Box 1-4. Confirming the diagnosis of asthma in a patient already taking controller treatment.

| Current status | Steps to confirm the diagnosis of asthma |
|---|---|
| Persistent shortness of breath and fixed airflow limitation | Consider stepping up controller treatment for 3 months, then reassess symptoms and lung function. If no response, resume previous treatment and refer patient for diagnosis and investigation. Consider asthma-COPD overlap syndrome. |

BD: bronchodilator;
LABA: long-acting beta2-agonist;
SABA: short-acting beta2-agonist In the methods of the disclosure "asthma" may be "mild asthma," "moderate asthma" or "severe asthma." In the methods of the disclosure asthma severity can be assessed according to the GINA guidance. In particular, asthma severity can assessed retrospectively from the level of treatment required to control symptoms and exacerbations. For example, it can be assessed once the patient has been on controller treatment for several months and, if appropriate, treatment step down has been attempted to find the patient's minimum effective level of treatment. Asthma severity is not a static feature and may change over months or years.

Figure 2:
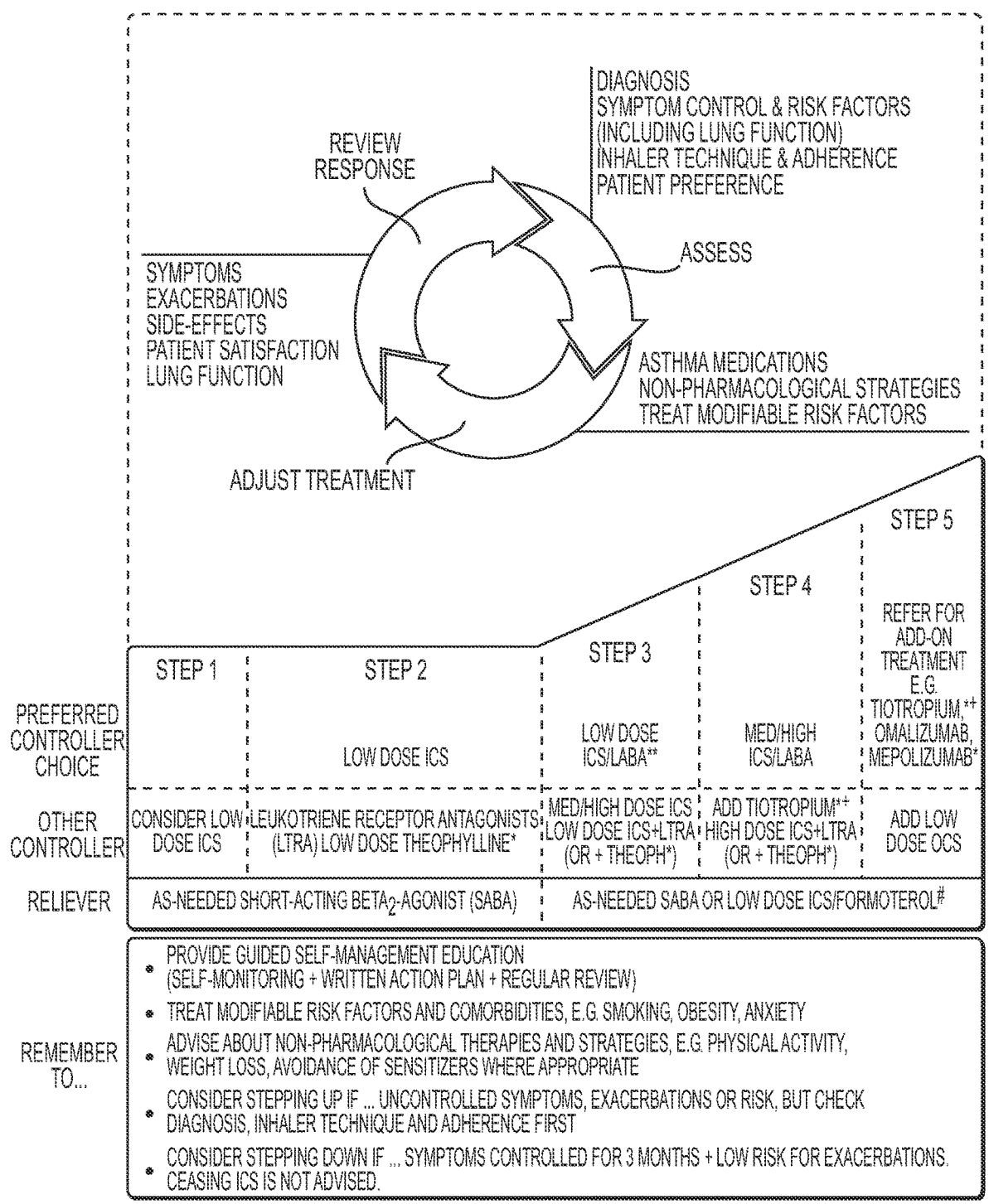
FIG. 2. Box 3-5. Stepwise approach to control symptoms and minimize future risk.

Asthma severity can be assessed when the patient has been on regular controller treatment for several months:

"Mild asthma" is asthma that is well controlled with Step 1 or Step 2 treatment (see FIG. 2; Box 3-5), i.e., with as-needed reliever medication alone, or with low-intensity controller treatment such as low dose ICS, leukotriene receptor antagonists or chromones.

"Moderate asthma" is asthma that is well controlled with Step 3 treatment (see FIG. 2; Box 3-5), e.g., low dose ICS/LABA.

"Severe asthma" is asthma that requires Step 4 or 5 treatment (see FIG. 2; Box 3-5), e.g., high-dose ICS/LABA, to prevent it from becoming 'uncontrolled', or asthma that remains 'uncontrolled' despite this treatment. While many patients with uncontrolled asthma may be difficult to treat due to inadequate or inappropriate treatment, or persistent problems with adherence or comorbidities such as chronic rhinosinusitis or obesity, the European Respiratory Society/American Thoracic Society Task Force on Severe Asthma considered that the definition of "severe asthma" should be reserved for patients with refractory asthma and those in whom response to treatment of comorbidities is incomplete. Table 4 can also be referred to during the assessment of asthma severity.

TABLE 4

Box 3-6. Low, medium and high daily doses of inhaled corticosteroids.

| Drug | Daily dose (mcg) | | |
|---|---|---|---|
| | Low | Medium | High |
| Beclometasone dipropionate (CFC)* | 200-500 | >500-1000 | >1000 |
| Beclometasone dipropionate (HFA) | 100-200 | >200-400 | >400 |
| Budesonide (DPI) | 200-400 | >400-800 | >800 |
| Ciclesonide (HFA) | 80-160 | >160-320 | >320 |
| Fluticasone furoate (DPI) | 100 | n.a. | 200 |
| Fluticasone propionate (DPI) | 100-250 | >250-500 | >500 |
| Fluticasone propionate (HFA) | 100-250 | >250-500 | >500 |

TABLE 4-continued

Box 3-6. Low, medium and high daily doses of inhaled corticosteroids.

| Drug | Daily dose (mcg) | | |
|---|---|---|---|
| | Low | Medium | High |
| Mometasone furoate | 110-220 | >220-440 | >440 |
| Triamcinolone acetonide | 400-1000 | >1000-2000 | >2000 |
| Children 6-11 years (for children 5 years and younger) | | | |
| Beclometasone dipropionate (CFC)* | 100-200 | >200-400 | >400 |
| Beclometasone dipropionate (HFA) | 50-100 | >100-200 | >200 |
| Budesonide (DPI) | 100-200 | >200-400 | >400 |
| Budesonide (nebules) | 250-500 | >500-1000 | >1000 |
| Ciclesonide | 80 | >80-160 | >160 |
| Fluticasone furoate (DPI) | n.a. | n.a. | n.a. |
| Fluticasone propionate (DPI) | 100-200 | >200-400 | >400 |
| Fluticasone propionate (HFA) | 100-200 | >200-500 | >500 |
| Mometasone furoate | 110 | ≥220-<440 | ≥440 |
| Triamcinolone acetonide | 400-800 | >800-1200 | >1200 |

CFC: chlorofluorocarbon propellant;
DPI: dry powder inhaler;
HFA: hydrofluoroalkane propellant;
n.a. not applicable
*Beclometasone dipropionate CFC is included for comparison with older literature In the methods of the disclosure "asthma" may be "mild eosinophilic asthma," "moderate eosinophilic asthma," or "severe eosinophilic asthma."

"Mild eosinophilic asthma" is mild asthma with an eosinophilic phenotype. For example, subjects with mild eosinophilic asthma may have mild asthma and blood eosinophils greater than or equal to 150 eosinophils per per μL of blood in the past 12 months, greater than or equal to 200 eosinophils per μL of blood in the past 12 months, greater than or equal to 300 eosinophils per μL of blood in the past 12 months or greater than or equal to 350 eosinophils per μL of blood in the past 12 months.

"Moderate eosinophilic asthma" is moderate asthma with an eosinophilic phenotype. For example, subjects with moderate eosinophilic asthma may have moderate asthma and blood eosinophils greater than or equal to 150 eosinophils per per μL of blood in the past 12 months, greater than or equal to 200 eosinophils per μL of blood in the past 12 months, greater than or equal to 300 eosinophils per μL of blood in the past 12 months or greater than or equal to 350 eosinophils per μL of blood in the past 12 months.

"Severe eosinophilic asthma" is severe asthma with an eosinophilic phenotype. For example, subjects with severe eosinophilic asthma may have severe asthma and blood eosinophils greater than or equal to 150 eosinophils per per μL of blood in the past 12 months, greater than or equal to 200 eosinophils per μL of blood in the past 12 months, greater than or equal to 300 eosinophils per μL of blood in the past 12 months (preferred) or greater than or equal to 350 eosinophils per μL of blood in the past 12 months.

Subjects with severe eosinophilic asthma may also meet, one or more of, the criteria described in Table 5.

TABLE 5

A subject has severe eosinophilic asthma if they meet the following criteria:

1) The subject has clinical features of severe refractory asthma similar to those indicated in the American Thoracic Society Workshop on Refractory Asthma (162 *Am. J. Respir. Crit. Care Med.* 2341 (2000) for ≥12 months.
2) The subject has a well-documented requirement for regular treatment with high dose ICS (inhaled corticosteroids) (i.e., ≥880 μg/day fluticasone propionate or equivalent daily), with or without maintenance OCS (oral corticosteroids), in the past 12 months.
3) The subject has a well-documented requirement for controller medication, e.g., long-acting beta-2-agonist, leukotriene receptor antagonist or theophylline in the past 12 months.
4) The subject has persistent airflow obstruction as indicated by a pre-bronchodilator $FEV_1$ <80% predicted recorded or peak flow diurnal variability of >20% on 3 or more days.
5) The subject has airway inflammation which is likely to be eosinophilic in nature as indicated by one of the following characteristics at present or documented in the previous 12 months:
An elevated peripheral blood eosinophil level of ≥300/μL that is related to asthma or
Sputum eosinophils ≥3% or
Exhaled nitric oxide ≥50 ppb or
Prompt deterioration of asthma control (based on documented clinical history or objective measures) following a ≤25% reduction in regular maintenance dose of inhaled or oral corticosteroid dose in the previous 12 months
8) The subject has a previously confirmed history of two or more asthma exacerbations requiring treatment with oral or systemic corticosteroids in the prior 12 months prior, despite the use of high-dose ICS and additional controller medication. For subjects receiving maintenance OCS with high-dose ICS plus controller, the OCS treatment for exacerbations had to be a two-fold or greater increase in the dose of OCS.
9) The subject has asthma as documented by either:
Airway reversibility ($FEV_1$ ≥12% and 200 mL) at present or documented in the previous 12 months or
Airway hyper-responsiveness (provocative concentration causing a 20% fall in $FEV_1$ of methacholine <8 mg/mL or provocative dose causing a 20% fall in $FEV_1$ of histamine <7.8 μmol) documented in the prior 12 months or
Airflow variability in clinic $FEV_1$ ≥20% between two examinations documented in the prior 12 months ($FEV_1$ recorded during an exacerbation is not valid) or
Airflow variability as indicated by >20% diurnal variability in peak flow observed on 3 or more days.

Importantly, subjects with severe eosinophilic asthma according to these criteria may have less than 150 eosinophils per μL, of blood at the initiation of treatment.

Mepolizumab is a monoclonal antibody comprising the heavy chain amino acid sequence shown in SEQ ID NO: 1 and the light chain amino acid sequence shown in SEQ ID NO: 2. Mepolizumab, and antigen binding proteins, in particular antibody molecules, comprising the heavy chain CDRs and light chain CDRs of mepolizumab (e.g., SEQ ID NO:s 5-10) or heavy chain variable region and light chain variable region of mepolizumab (e.g., SEQ ID NO: 3 and SEQ ID NO: 4), may be used to treat patients according to the methods of the disclosure. Mepolizumab specifically binds human IL-5 (SEQ ID NO: 11) and antagonizes the activity of the IL-5R receptor (comprising SEQ ID NO:s 12 and 13). NUCALA™ is an example of a FDA approved pharmaceutical composition comprising mepolizumab.

Mepolizumab or the compositions of the disclosure comprising mepolizumab, may be indicated for add-on maintenance treatment of severe eosinophilic asthma, as identified by blood eosinophils greater than or equal to 300 cells/μL in the past 12 months and/or blood eosinophils greater than or equal to 150 cells/μL at initiation of treatment and/or blood eosinophils less than 150 cells/μL at initiation of treatment, in pediatric patients. Alternatively, mepolizumab or the compositions of the disclosure comprising mepolizumab, may be indicated for add-on maintenance treatment of severe eosinophilic asthma, as identified by blood eosinophils greater than or equal to 300 cells/μL in the past 12 months and/or blood eosinophils greater than or equal to 150 cells/μL at initiation of treatment, in pediatric patients. Mepolizumab or the compositions of the disclosure comprising mepolizumab, may be indicated for add-on maintenance treatment of severe eosinophilic asthma, as identified by blood eosinophils greater than or equal to 300 cells/μL in the past 12 months and/or blood eosinophils less than 150 cells/μL at initiation of treatment, in pediatric patients. Such pediatric patients may be between 11 years of age and 6 years of age inclusive. Treatment with mepolizumab or the compositions of the disclosure comprising mepolizumab, may reduce exacerbations of asthma in pediatric patients (e.g., patients with an exacerbation history). The methods of the disclosure may be used when treatment with mepolizumab or the compositions of the disclosure comprising mepolizumab, is indicated (i.e., such treatment with mepolizumab, may be combined with the methods of the disclosure). Treatment with mepolizumab or the compositions of the disclosure comprising mepolizumab can:

a) Produce a reduction in exacerbation frequency. Compared with placebo, treatment with mepolizumab or the compositions of the disclosure comprising mepolizumab, can reduce the rate of 1) clinically significant exacerbations, 2) exacerbations requiring hospitalization or ED visits, and 3) exacerbations requiring hospitalization. This benefit may potentially lead to reductions in morbidity and fatal events due to asthma.
b) Produce a reduction in daily OCS dose: Treatment with mepolizumab or the compositions of the disclosure comprising mepolizumab may allow subjects to reduce their daily dose of concomitant corticosteroid without experiencing loss of asthma control. Subjects treated with mepolizumab or the compositions of the disclosure comprising mepolizumab may achieve a median percentage reduction of from baseline in daily oral corticosteroid (OCS) dose versus those treated with placebo. In addition, subjects treated with mepolizumab or the compositions of the disclosure comprising mepolizumab, or the antigen binding compositions of the disclosure may achieve a reduction of OCS dose compared to subjects treated with placebo.

c) Produce an improvement in lung function: Clinically relevant changes in pre- and post-bronchodilator $FEV_1$ may be demonstrated by treatment with mepolizumab or the compositions of the disclosure comprising mepolizumab compared with placebo. Any improvements in lung function are of particular clinical importance in this population of subjects as most are on maximal asthma therapy including high dose ICS (inhaled corticosteroids) and/or OCS plus a controller medication.

d) Produce an improvement in asthma control: Statistically significant and clinically relevant improvements may be observed in ACQ-5 or ACQ-7 with mepolizumab or the compositions of the disclosure comprising mepolizumab, compared with placebo, indicating subjects may achieve asthma control with the addition of mepolizumab or the compositions of the disclosure comprising mepolizumab to their existing asthma treatment.

e) Produce an improvement in quality of life: Statistically significant and clinically relevant changes in SGRQ scores may be demonstrated with mepolizumab or the compositions of the disclosure comprising mepolizumab compared with placebo. Subjects may experience marked improvement in asthma symptoms and ability of perform daily activities.

f) Produce a persistence of efficacy and pharmacodynamic effect: Over a period treatment duration (e.g., 4, 8, 9, 12 16 and 20 weeks), a sustained reduction in asthma exacerbations and blood eosinophils, and improvements in lung function, asthma control, and quality of life with no development of tolerance may be observed. and g) Produce a reduction in blood eosinophils. Treatment with compositions comprising mepolizumab or the compositions of the disclosure comprising mepolizumab may result in rapid reduction of blood eosinophils in a subject.

In the methods of the disclosure "asthma" may be "severe asthma." In the methods of the disclosure "asthma" may also be "mild asthma," "moderate asthma," "severe asthma," "mild eosinophilic asthma," "moderate eosinophilic asthma," or "severe eosinophilic asthma" as discussed above. Treatment with compositions comprising mepolizumab or the compositions of the disclosure comprising mepolizumab, may be used to treat these conditions according to the methods of the disclosure.

In the methods of the disclosure "asthma" may be "uncontrolled eosinophilic asthma." Subjects with uncontrolled eosinophilic asthma meet the criteria described in Table 6.

TABLE 6

| A subject has uncontrolled eosinophilic asthma if they meet the following criteria: |
| --- |
| 1) The subject has a history of diagnosed asthma for at least the prior 12 months.
2) The subject has been prescribed daily use of medium-dose or high-dose ICS (inhaled corticosteroid) plus LABA (long-acting beta agonists) for at least the prior 12 months.
3) The subject's dose of other asthma controller medications must be stable for at least the prior 30 days.
4) The subject has at least 2 documented asthma exacerbations in the prior 12 months that required use of a systemic corticosteroid burst. |

Treatment with compositions comprising mepolizumab or the compositions of the disclosure comprising mepolizumab, may be used to treat uncontrolled eosinophilic asthma according to the methods of the disclosure.

In the methods of the disclosure "asthma" may be "eosinophilic asthma." Subjects with eosinophilic asthma meet the criteria described in Table 7.

TABLE 7

| A subject has eosinophilic asthma if they meet the following criteria: |
| --- |
| 1) The patient has a previous diagnosis of asthma.
2) The patient has had at least 1 asthma exacerbation requiring oral, intramuscular (im), or intravenous (iv) corticosteroid use for at least 3 days in the prior 12 months.
3) The patient has a current blood eosinophil level of at least 400/µl.
4) The patient has airway reversibility of at least 12% to beta-agonist administration.
5) The patient has an ACQ score of at least 1.5.
6) The patient is taking inhaled fluticasone at a dosage of at least 440 µg, or equivalent, daily. Chronic oral corticosteroid use (no more than 10 mg/day prednisone or equivalent) is allowed. The patient's baseline asthma therapy regimen (including, but not limited to, inhaled corticosteroids, oral corticosteroids up to a maximum dose of 10 mg prednisone daily or equivalent, leukotriene antagonists, 5-lipoxygenase inhibitors, or cromolyn) must be stable for the prior 30 days. |

In the methods of the disclosure "asthma" may be "sub-eosinophilic asthma." Subjects with sub-eosinophilic asthma meet the criteria described in Table 8.

TABLE 8

A subject has sub-eosinophilic asthma if they meet the following criteria:

1) The patient has a previous diagnosis of asthma.
2) The patient has had at least 1 asthma exacerbation requiring oral, intramuscular (im), or intravenous (iv) corticosteroid use for at least 3 days in the prior 12 months.
3) The patient has a current blood eosinophil level of less than 400/μl.
4) The patient has airway reversibility of at least 12% to beta-agonist administration.
5) The patient has an ACQ score of at least 1.5.
6) The patient is taking inhaled fluticasone at a dosage of at least 440 μg, or equivalent, daily. Chronic oral corticosteroid use (no more than 10 mg/day prednisone or equivalent) is allowed. The patient's baseline asthma therapy regimen (including, but not limited to, inhaled corticosteroids, oral corticosteroids up to a maximum dose of 10 mg prednisone daily or equivalent, leukotriene antagonists, 5-lipoxygenase inhibitors, or cromolyn) must be stable for the prior 30 days.

Treatment with compositions comprising mepolizumab or the compositions of the disclosure comprising mepolizumab may be used to treat eosinophilic asthma and may also be used to treat sub-eosinophilic asthma according to the methods of the disclosure.

The term "bullous pemphigoid" (BP) as used herein means an acute or chronic autoimmune skin disease, involving the formation of blisters, more appropriately known as bullae, at the space between the skin layers epidermis and dermis. BP is the most common autoimmune blistering skin disease. It characteristically affects the elderly (>70 years) with an annual incidence of 5 to 35 per million. The incidence of BP is dramatically increasing with an average of 17% per year. BP often starts with extremely pruritic skin lesions resembling eczema or urticaria before vesicles and blisters arise. In 10-30% of patients, BP also involves the oral mucosa. Disease severity can be determined by means of the autoimmune bullous skin disorder intensity score (ABSIS) that evaluates the involved area as well as the disease activity. The disease is due to an autoimmune response to structural components of junctional adhesion complexes leading to the damage of the dermal-epidermal junction with subepidermal blister formation. Specifically, autoreactive B and T cell responses against the hemidesmosomal antigens BP180 and BP230 have been identified. Serum levels of autoantibodies to BP180 reflect the disease severity and activity. The T cells are memory CD4+ cells producing both Th1 and Th2 cytokines, mostly IL-4, IL-5 and IL-13. IL-5 as well as eotaxin are abundantly found in blister fluids. The production of IL-5 is indeed associated with blood eosinophilia and significant eosinophil infiltration in the skin of BP patients. Eosinophils are thought to be critically implicated in blister formation by releasing toxic granule proteins (ESP, MBP) and proteolytic enzymes.

The term "eosinophilic esophagitis" (EoE) as used herein means an allergic inflammatory condition of the esophagus that involves eosinophils. Symptoms are swallowing difficulty, food impaction, and heartburn. EoE is characterised by a dense infiltrate with white blood cells of the eosinophil type into the epithelial lining of the esophagus. EoE is believed to be an allergic reaction against ingested food, based on the important role eosinophils play in allergic reactions. The EoE diagnostic panel can be used to diagnose EoE. EoE can also be diagnosed if gastroesophageal reflux does not respond to a 6 week trial of twice-a-day high-dose proton-pump inhibitors (PPIs) or if a negative ambulatory pH study ruled out gastroesophageal reflux disease (GERD). Endoscopically, ridges, furrows, or rings may be seen in the oesophageal wall. Sometimes, multiple rings may occur in the esophagus, leading to the term "corrugated esophagus" or "feline esophagus" due to similarity of the rings to the cat esophagus. The presence of white exudates in esophagus is also suggestive of the diagnosis. On biopsy taken at the time of endoscopy, numerous eosinophils can typically be seen in the superficial epithelium. A minimum of 15 eosinophils per high-power field are required to make the diagnosis. Eosinophilic inflammation is not limited to the oesophagus alone, and does extend though the whole gastrointestinal tract. Profoundly degranulated eosinophils may also be present, as may microabcesses and an expansion of the basal layer. Radiologically, the term "ringed esophagus" has been used for the appearance of eosinophilic esophagitis on barium swallow studies to contrast with the appearance of transient transverse folds sometimes seen with esophageal reflux (termed "feline esophagus").

Treatment with compositions comprising mepolizumab or the compositions of the disclosure comprising mepolizumab may be used to treat COPD according to the methods of the disclosure.

Subjects with "chronic obstructive pulmonary disease" (COPD) may meet one or more of the following criteria: a) a prior COPD diagnosis: subjects with a clinically documented history of COPD for at least 1 year in accordance with the definition by the American Thoracic Society/European Respiratory Society; b) severity of COPD: Subjects may present with the following: a measured pre and post-salbutamol Forced Expiratory Volume in one second/Forced vital capacity ($FEV_1$/FVC) ratio of <0.70 to confirm a diagnosis of COPD; a measured post-salbutamol $FEV_1$>20 percent and <=80 percent of predicted normal values calculated using National Health and Nutrition Examination Survey (NHANES) III reference equations; c) a history of exacerbations: a well documented history (like medical record verification) in the 12 months of: at least two moderate COPD exacerbations. Moderate is defined as the use of systemic corticosteroids (IM, intravenous, or oral) and/or treatment with antibiotics, or at least one severe COPD exacerbation. Severe is defined as having required hospitalization. Note: At least one exacerbation must have occurred while the subject was taking Inhaled corticosteroid (ICS) plus long acting beta2-agonist (LABA) plus long acting muscarinic antagonist (LAMA). Note: Prior use of antibiotics alone does not qualify as a moderate exacerbation unless the use was specifically for the treatment of worsening symptoms of COPD; and d) concomitant COPD therapy: a well documented requirement for optimized standard of care (SoC) background therapy that includes ICS plus 2 additional COPD medications (i.e., triple therapy) for the 12 months prior and meets the following criteria: Immediately prior to visit to the healthcare provider, a minimum of 3 months of use of an inhaled corticosteroid (at a dose >=500 micrograms (mcg)/day fluticasone propionate dose equivalent plus); or LABA and LAMA.

Treatment with compositions comprising mepolizumab or the compositions of the disclosure comprising mepolizumab may be used to treat COPD according to the methods of the disclosure.

The term "eosinophilic granulomatosis with polyangiitis" (EGPA) as used herein means an autoimmune condition that causes inflammation of small and medium-sized blood vessels (vasculitis) in persons with a history of airway allergic hypersensitivity (atopy). EGPA may also be referred to as Churg-Strauss Syndrome (CSS) or allergic granulomatosis. EGPA usually manifests in three stages. The early (prodromal) stage is marked by airway inflammation; almost all patients experience asthma and/or allergic rhinitis. The second stage is characterized by abnormally high numbers of eosinophils (hypereosinophilia), which causes tissue damage, most commonly to the lungs and the digestive tract. The third stage consists of vasculitis, which can eventually lead to cell death and can be life-threatening.

Subjects with EGPA may meet one or more following criteria: a) asthma; b) blood eosinophil levels greater than 10% of a differential white blood cell count; c) presence of mononeuropathy or polyneuropathy; d) unfixed pulmonary infiltrates; e) presence of paranasal sinus abnormalities; and e) histological evidence of extravascular eosinophils. For classification purposes, a patient shall be said to have EGPA if at least four of the preceding six criteria are positive.

Treatment with compositions comprising mepolizumab or the compositions of the disclosure comprising mepolizumab may be used to treat EGPA according to the methods of the disclosure. The compositions of the disclosure may be administered to a pediatric EGPA patient in an amount of 300 mg once every 4 weeks.

The term "hypereosinophilic syndrome" (HES) as used herein means a disease characterized by a persistently elevated eosinophil count (≥1500 eosinophils/mm³) in the blood for at least six months without any recognizable cause, with involvement of either the heart, nervous system, or bone marrow.

Subjects with hypereosinophilic syndrome may meet one or more following criteria:

a) a documented history of hypereosinophilic syndrome; b) a blood eosinophil count greater than 1500 cells for 6 months; c) signs and symptoms of organ system involvement; and d) no evidence of parasitic, allergic or other causes of eosinophilia after comprehensive evaluation.

Treatment with compositions comprising mepolizumab or the compositions of the disclosure comprising mepolizumab may be used to treat hypereosinophilic syndrome according to the methods of the disclosure.

The term "nasal polyposis" as used herein means a disease characterized by the presence of polyps nasal cavity. Such polyps may be in the upper nasal cavity and/or may originate from within the ostiomeatal complex.

Subjects with nasal polyposis may meet one or more following criteria: a) a documented history of nasal polyposis; or b) nasal polyps apparent on examination (e.g., endoscopic examination).

Treatment with compositions comprising mepolizumab or the compositions of the disclosure comprising mepolizumab may be used to treat nasal polyposis according to the methods of the disclosure.

The term "atopic dermatitis" as used herein means an inflammatory skin condition characterized by chronic pruritus, lichenification, xerosis, erythematous papules and plaques.

In the methods of the disclosure "atopic dermatitis" may be "moderate to severe atopic dermatitis." Subjects with moderate to severe atopic dermatitis may meet, one or more of, the criteria described in Table 9.

TABLE 9

A subject has moderate to severe atopic dermatitis if they meet the following criteria (e.g., all, or "one or more"):

1. An atopic dermatitis diagnosis according to the Eichenfield revised criteria of Hanifin and Rajka (Eichenfield et al., 70 J Am Acad Dermatol 338 (2014)). See Table 10.
2. Diagnosis of atopic dermatitis ≥2 years prior to beginning treatment.
3. A health care professional's global assessment (HGA; also sometimes called an investigator's global assessment or IGA) score ≥3 prior to beginning treatment. See Table 11.
4. Atopic dermatitis involvement of ≥10% BSA prior to beginning treatment. See Table 12.
5. An eczema area and severity index (EASI) score ≥16 prior to beginning treatment. See Table 13.
6. An absolute blood eosinophil count ≥350 cells/µL prior to beginning treatment.
7. Optionally, applied a non-prescription, non-medicated (without an active ingredient) emollient twice-daily for at least 7 days immediately prior to beginning treatment.
8. Prior to beginning treatment having at least one of: a) an inadequate response ≤6 months to a stable regimen of prescription topical medication for atopic dermatitis; b) poor tolerance of prescription topical medications for atopic dermatitis; c) a concern for potential side effects from prescription topical medications for atopic dermatitis, such as skin thinning or increased risk of hypothalamic-pituitary-adrenal [HPA] suppression; and/or d) an inadequate response to optimization of nonpharmacological measures for atopic dermatitis such as moisturizers. An "inadequate response" to a stable regimen of prescription topical medication for atopic dermatitis (such as medium to high potency topical corticosteroids or topical calcineurin inhibitors) is defined as failure to achieve and maintain remission or low disease activity state (equivalent to an HGA score = 0 [clear] to 2 [mild]) despite treatment for the recommended duration as per label or for the maximum duration recommended for the subject treatment, whichever is shorter.

Subjects with moderate to severe atopic dermatitis may be children under 18 years of age, adults at least 18 years of age or older, adults between 18 and 70 years of age inclusive, or pediatric subjects between 11 years of age and 6 years of age inclusive. Subjects may be male or female. It is preferred female subjects to be treated are not pregnant, not lactating and/or not likely to become pregnant.

The diagnosis of atopic dermatitis is based on the Eichenfield revised criteria of Hanifin and Rajka Eichenfield revised criteria of Hanifin and Rajka. See Table 10 and Eichenfield et al., 70 J Am Acad Dermatol 338 (2014).

TABLE 10

Criteria for Atopic Dermatitis Diagnosis

ESSENTIAL FEATURES- Must be present:
    Pruritus
    Eczema (acute, subacute, chronic)
        Typical morphology and age-specific patterns*
        Chronic or relapsing history
  *Patterns include:
    1. Facial, neck, and extensor involvement in infants and children
    2. Current or previous flexural lesions in any age group
    3. Sparing of the groin and axillary regions
IMPORTANT FEATURES- Seen in most cases, adding support to the diagnosis:
    Early age of onset
    Atopy
        Personal and/or family history
        Immunoglobulin E reactivity
    Xerosis
ASSOCIATED FEATURES- These clinical associations help to suggest the diagnosis of atopic dermatitis but are too nonspecific to be used for defining or detecting atopic dermatitis for research and epidemiologic studies:
    Atypical vascular responses (e.g., facial pallor, white dermographism, delayed
    blanch response)
    Keratosis pilaris/pityriasis alba/hyperlinear palms/ichthyosis
    Ocular/periorbital changes
    Other regional findings (e.g., perioral changes/periauricular lesions)
    Perifollicular accentuation/lichenification/prurigo lesions
EXCLUSIONARY CONDITIONS-It should be noted that a diagnosis of atopic dermatitis depends on excluding conditions, such as:
    Scabies
    Seborrheic dermatitis
    Contact dermatitis (irritant or allergic)
    Ichthyoses
    Cutaneous T-cell lymphoma
    Psoriasis
    Photosensitivity dermatoses
    Immune deficiency diseases
    Erythroderma of other causes The health care professional's global assessment (HGA) a clinical tool for assessing the current state/severity of a subject's atopic dermatitis. See Rehal et al, 6 PLos ONE e17520 (2011) and Table 11. It is a static 5-point morphological assessment of overall disease severity as determined by a trained healthcare professional using the clinical characteristics of erythema, infiltration, papulation, oozing, and crusting as guidelines. The HGA is made without reference to previous scores. Each assessment should be made as a visual 'average' of the severity of all affected areas at the time of the assessment.

TABLE 11

Healthcare Professional's Global Assessment (HGA)

| Score/Grade | Description |
| --- | --- |
| 0 Clear | No erythema or induration/papulation, no oozing/crusting; there may be residual discoloration. |
| 1 Almost Clear | There may be trace faint pink erythema, with almost no induration/papulation, and no oozing/crusting. |
| 2 Mild | There may be faint pink erythema, with induration/papulation with barely perceptible elevations, and no oozing/crusting. |
| 3 Moderate | There may be clearly distinguishable dull red erythema with induration/papulation with clearly perceptible elevations but not prominent; there may be some oozing/crusting. |
| 4 Severe | There may be deep or bright red erythema with induration/papulation with prominent elevations (deep step off of border), with oozing/crusting. |

The assessment of percentage of body surface area (% BSA) is an estimate of the percentage of total involved skin with atopic dermatitis. See FIG. 4. The % BSA assessment may be performed by looking at inflamed areas from within each of the 4 body surface regions separately: the head and neck, the upper extremities, the trunk and the lower extremities, and each of these body regions can potentially have up to 100% involvement. The raters (e.g., health care professional) will estimate the percentage of involved skin for each of the regions for a % BSA area score that is then multiplied by the appropriate proportionality multiplier to yield the % BSA regional involved value (for subjects ≥8 years of age, 0.1 for head, 0.2 upper extremities, 0.3 for trunk and 0.4 for lower extremities). The regional % BSA involved values are summed to generate the total involved % BSA. The regional % BSA area score will also be utilized as part of the matrix to calculate the EASI score.

The EASI scoring system is a standardized clinical tool for the assessment of atopic dermatitis that takes into account the overall extent of the % body surface area (% BSA) involved and the severity scores for each of the clinical signs: erythema, induration/papulation, excoriation, and lichenification. See Hanifin et al., 10 Exp Dermatol 11 (2001); Rullo et al., 36 Allergol et Immunopathol 201 (2008) and FIG. 5. The % BSA area score from the % BSA assessment is to be used as part of the matrix to calculate the EASI score. Severity scores for each of the clinical signs (erythema, induration/papulation, excoriation, and lichenification) are graded on a 4-point scale (0 to 3) for each of the 4 body regions (head and neck, upper extremities, lower extremities, and trunk). The severity scores for each of the signs are summed for each region and multiplied by the % BSA area score and by the appropriate proportionality multiplier (for subjects >8 years of age, 0.1 for head, 0.2 upper extremities, 0.3 for trunk and 0.4 for lower extremities) to generate a regional EASI score. The regional EASI scores are then summed to yield the final EASI score. The EASI score is a static assessment made without reference to previous scores.

Therapeutically effective amounts of mepolizumab or the compositions of the disclosure comprising mepolizumab can be used to treat a patient with atopic dermatitis or reduce absolute blood eosinophil counts in such patients. Such atopic dermatitis may be moderate atopic dermatitis or severe atopic dermatitis.

Treatment of atopic dermatitis—such as moderate atopic dermatitis or severe atopic dermatitis—with mepolizumab or the compositions of the disclosure comprising mepolizumab, according to the methods of the disclosure can produce at least one result selected from the group consisting of:
  a) an HGA score of 0 or 1 and at least a 2-grade improvement in the HGA (e.g., relative to a starting HGA score);
  b) a decrease in Eczema Area and Severity Index (EASI) score (e.g., relative to a starting EASI score);
  c) a decrease in percent of total body surface area (% BSA) affected (e.g., relative to a starting % BSA); and/or
  d) a determination by a health care professional that a subject does not have atopic dermatitis according to the Eichenfield revised criteria of Hanifin and Rajka (Eichenfield et al., 70 J Am Acad Dermatol 338 (2014).

The EASI score after treatment according to the methods of the disclosure may be less than 16 such as for example from about 0 to less than 16. The EASI score after treatment may also be from about 0 to about 15, about 0 to about 14, about 0 to about 13, about 0 to about 12, about 0 to about 11, about 0 to about 10, about 0 to about 9, about 0 to about 8, about 0 to about 7, about 0 to about 6, about 0 to about 5, about 0 to about 4, about 0 to about 3, about 0 to about 2, about 0 to about 1, from about 1 to less than 16, from about 2 to less than 16, from about 3 to less than 16, from about 4 to less than 16, from about 5 to less than 16, from about 6 to less than 16, from about 7 to less than 16, from about 8 to less than 16, from about 9 to less than 16, from about 10 to less than 16, from about 11 to less than 16, from about 12 to less than 16, from about 13 to less than 16, from about 14 to less than 16, from about 15 to less than 16, from about 2 to about 15, from about 3 to about 14, from about 4 to about 13, from about 5 to about 12, from about 6 to about 11, from about 7 to about 10, from about 8 to about 9, from about 0 to about 8, from about 8 to less than 16, from about 0 to about 4, from about 4 to about 8, from about 8 to about 12 and from about 12 to less than 16.

The % BSA after treatment according to the methods of the disclosure may be less than about 10% such as for example from about 0% to less than 10%. The % BSA after treatment may also be from about 1% to less than 10%, from about 2% to less than 10%, from about 3% to less than 10%, from about 4% to less than 10%, from about 5% to less than 10%, from about 6% to less than 10%, from about 7% to less than 10%, from about 8% to less than 10%, from about 9% to less than 10%, from about 0% to about 9%, from about 0% to about 8%, from about 0% to about 7%, from about 0% to about 6%, from about 0% to about 5%, from about 0% to about 4%, from about 0% to about 3%, from about 0% to about 3%, from about 0% to about 2%, from about 0% to about 1%, from about 0% to about 5%, from about 5% to less than 10%, from about 0% to about 2.5%, from about 2.5% to about 5%, from about 5% to about 7.5% and from about 7.5% to less than 10%.

The term "antigen binding protein", as used herein refers to isolated antibodies, antibody fragments (e.g., Fabs etc.) and other antibody derived protein constructs—such as those comprising antibody domains (e.g., domain antibodies etc.)—which are capable of binding to human IL-5 (SEQ ID NO: 11).

The term "antibody" as used herein refers to molecules with an immunoglobulin-like domain (e.g., IgG, IgM, IgA, IgD or IgE) and includes monoclonal, recombinant, polyclonal, monoclonal, recombinant, polyclonal, chimeric, human, and humanized molecules of this type. Monoclonal antibodies may be produced by a eukaryotic cell clone expressing an antibody. Monoclonal antibodies may also be produced by a eukaryotic cell line which can recombinantly express the heavy chain and light chain of the antibody by virtue of having nucleic acid sequences encoding these introduced into the cell. Methods to produce antibodies from different eukaryotic cell lines such as Chinese Hamster Ovary cells, hybridomas or immortalized antibody cells derived from an animal (e.g., human) are well known.

The antibody may be derived from rat, mouse, primate (e.g., cynomolgus, Old World monkey or Great Ape), human or other sources such as nucleic acids generated using molecular biology techniques which encode an antibody molecule.

The antibody may comprise a constant region, which may be of any isotype or subclass. The constant region may be of the IgG isotype, for example, $IgG_1$, $IgG_2$, $IgG_3$, $IgG_4$ or variants thereof. The antigen binding protein constant region may be $IgG_1$.

The antigen binding protein may comprise one or more modifications selected from a mutated constant domain such that the antibody has enhanced effector functions/ADCC and/or complement activation.

An antibody may be capable of binding to a target antigen. Examples, of such target antigens include human IL-5 comprising the amino acid sequence shown in SEQ ID NO: 11.

Mepolizumab comprising the heavy chain amino acid sequence shown in SEQ ID NO: 1 and the light chain amino acid sequence shown in SEQ ID NO: 2 is an example of such an antibody. Mepolizumab or the compositions of the disclosure comprising mepolizumab bind human IL-5 and antagonizes its activity.

Mepolizumab is a recombinant humanized monoclonal antibody (IgG$_1$, Kappa). Mepolizumab has two light and two heavy chains.

The mepolizumab heavy and light chains are covalently linked by a single disulfide bond and the heavy chains are linked to each other by two disulfide bonds resulting in a typical IgG molecule.

Mepolizumab or the compositions of the disclosure comprising mepolizumab can be provided as a lyophilized powder containing the antibody and excipients which can be reconstituted with a pharmaceutically acceptable carrier (e.g., sterile water). This reconstituted pharmaceutical composition can then be administered either subcutaneously or intravenously (e.g., with further dilution). Mepolizumab or the compositions of the disclosure comprising mepolizumab can also be provided as a liquid formulation containing the antibody, excipients and a pharmaceutically acceptable carrier. This liquid pharmaceutical composition can then be administered either subcutaneously or intravenously (e.g., with further dilution).

The term "antibody variant" as used herein means an antibody that differs from a parent antibody by virtue of at least one amino acid modification (e.g., by having a different amino acid side chain), post-translational modification or other modification in at least one heavy chain, light chain, or combinations of these that results in a structural change (e.g., different amino acid side chain, different post-translational modification or other modification) relative to the parent antibody. Mepolizumab is an example of a such a parent antibody. Structural changes can be determined directly by a variety of methods well know in the art such as LC-MS, direct sequencing or indirectly via methods such as isoelectric focusing and the like. Such methods are well known to those of ordinary skill in the art.

The term "IL-5" as used herein means human IL-5 comprising the amino acid sequence shown in SEQ ID NO: 11.

The term "specifically binds", as used herein in relation to antigen binding proteins means that the antigen binding protein binds to a target antigen as well as a discrete domain, or discrete amino acid sequence, within a target antigen with no or insignificant binding to other (for example, unrelated) proteins. This term, however, does not exclude the fact that the antigen binding proteins may also be cross-reactive with closely related molecules (for example, those with a high degree of sequence identity or from another genera or species). The antigen binding proteins described herein may bind to human IL-5 or the human IL-5 receptor with at least 2, 5, 10, 50, 100, or 1000-fold greater affinity than they bind to closely related molecules.

The binding affinity ($K_D$) of the antigen binding protein-target antigen interaction may be 1 mM or less, 100 nM or less, 10 nM or less, 2 nM or less or 1 nM or less. Alternatively, the $K_D$ may be between 5 and 10 nM; or between 1 and 2 nM. The $K_D$ may be between 1 pM and 500 pM; or between 500 pM and 1 nM. The binding affinity of the antigen binding protein is determined by the association constant (Ka) and the dissociation constant (Kd) (KD=Kd/Ka). The binding affinity may be measured by BIACORE™, for example, by capture of the test antibody onto a protein-A coated sensor surface and flowing target antigen over this surface. Alternatively, the binding affinity can be measured by FORTEBIO, for example, with the test antibody receptor captured onto a protein-A coated needle and flowing target antigen over this surface.

The $K_d$ may be $1\times10^{-3}$ Ms$^{-1}$ or less, $1\times10^{-4}$ Ms$^{-1}$ or less, or $1\times10^{-5}$ Ms$^{-1}$ or less. The $K_d$ may be between $1\times10^{-5}$ Ms$^{-1}$ and $1\times10^{-4}$ Ms$^{-1}$; or between $1\times10^{-4}$ Ms$^{-1}$ and $1\times10^{-3}$ Ms$^{-1}$. A slow $K_d$ may result in a slow dissociation of the antigen binding protein-target antigen complex and improved neutralization of the target antigen.

The term "specific antigen binding activity" as used herein means antigen binding activity as measured by Surface Plasmon Resonance (SPR). IL-5 specific binding activity may be determined by SPR using a BIACORE™ instrument, for example performed in the binding mode. It is binding activity divided by total protein content in a sample.

The term "FcRn binding activity" as used herein means Neonatal Fc (FcRn) Receptor binding activity as measured by Surface Plasmon Resonance (SPR). FcRn binding may be determined using a BIACORE™ instrument. It is binding activity to the FcRn receptor, divided by the total protein concentration of the sample.

The SPR method for specific antigen binding and FcRn binding uses a reference standard of mepolizumab. The mepolizumab reference standard can be used in assays to obtain system suitability and sample comparability data, to ensure methods are performing appropriately. The reference standard can allow the establishment of a calibration curve and concentrations of the samples are interpolated from the curve.

By "isolated", it is intended that the molecule, such as an antigen binding protein or nucleic acid, is removed from the environment in which it may be found in nature. For example, the molecule may be purified away from substances with which it would normally exist in nature. For example, the mass of the molecule in a sample may be 95% of the total mass. Importantly, the mepolizumab antibody and antigen binding proteins of the disclosure are typically provided as compositions that can comprise any combination of the nucleic acids of the disclosure, buffer, residual buffer, salts, counter ions, water, alcohols or vector and the like.

The terms "$V_H$" and "$V_L$" are used herein to refer to the heavy chain variable region and light chain variable region respectively of an antigen binding protein.

"CDRs" are defined as the complementarity determining region amino acid sequences of an antigen binding protein. These are the hypervariable regions of immunoglobulin heavy and light chains. There are three heavy chain and three light chain CDRs (or CDR regions) in the variable portion of an immunoglobulin. Thus, "CDRs" as used herein refers to all three heavy chain CDRs, all three light chain CDRs, all heavy and light chain CDRs, or at least one CDR and wherein the at least one CDR is CDRH3. Framework regions follow each of these CDR regions. Acceptable heavy chain variable region and light chain variable region framework 1, framework 2 and framework 3 regions are readily recognized by those of ordinary skill in the art. Acceptable heavy chain constant regions (including hinge regions) and light chain constant regions are readily recognized by those of ordinary skill in the art as well. Acceptable antibody isotypes are similarly readily recognized by those of ordinary skill in the art.

Throughout this specification, amino acid residues in variable domain sequences and full length antibody sequences are numbered according to the Kabat numbering convention. Similarly, the terms "CDR", "CDRL1", "CDRL2", "CDRL3", "CDRH1", "CDRH2", "CDRH3" used in the specification follow the Kabat numbering convention.

It will be apparent to those skilled in the art that there are alternative numbering conventions for amino acid residues in variable domain sequences and full length antibody sequences. There are also alternative numbering conventions for CDR sequences, for example those set out according to the Chothia numbering convention. The structure and protein folding of the antibody may mean that other residues are considered part of the CDR sequence and would be understood to be so by a skilled person.

Other numbering conventions for CDR sequences available to a skilled person include "AbM" (University of Bath) and "contact" (University College London) methods. The minimum overlapping region using at least two of the Kabat, Chothia, AbM and contact methods can be determined to provide the "minimum binding unit". The minimum binding unit may be a sub-portion of a CDR.

Table 14 below represents one definition using each numbering convention for each CDR or binding unit. The Kabat numbering scheme is used in Table 14 to number the variable domain amino acid sequence. It should be noted that some of the CDR definitions may vary depending on the individual publication used.

TABLE 14

|    | Kabat CDR | Chothia CDR | AbM CDR | Contact CDR | Minimum binding unit |
|----|-----------|-------------|---------|-------------|----------------------|
| H1 | 31-35/35A/35B | 26-32/33/34 | 26-35/35A/35B | 30-35/35A/35B | 31-32 |
| H2 | 50-65 | 52-56 | 50-58 | 47-58 | 52-56 |
| H3 | 95-102 | 95-102 | 95-102 | 93-101 | 95-101 |
| L1 | 24-34 | 24-34 | 24-34 | 30-36 | 30-34 |
| L2 | 50-56 | 50-56 | 50-56 | 46-55 | 50-55 |
| L3 | 89-97 | 89-97 | 89-97 | 89-96 | 89-96 |

"Percent identity" between a query nucleic acid sequence and a subject nucleic acid sequence is the "Identities" value, expressed as a percentage, that is calculated by the BLASTN algorithm when a subject nucleic acid sequence has 100% query coverage with a query nucleic acid sequence after a pair-wise BLASTN alignment is performed. Such pair-wise BLASTN alignments between a query nucleic acid sequence and a subject nucleic acid sequence are performed by using the default settings of the BLASTN algorithm available on the National Center for Biotechnology Institute's website with the filter for low complexity regions turned off. Importantly, a query sequence may be described by a nucleic acid sequence identified in one or more claims herein.

Nucleic acid sequences which may be useful, and included, in the compositions and related methods of the disclosure may have between about 85% to about 100%, about 90% to about 100%, about 95% to about 100%, about 91%, about 92%, about 93%, about 94%, about 95%, about 96%, about 97%, about 98%, about 99% and about 100% identity to the nucleic acid sequences identified in the disclosure (e.g., nucleic acids encoding an antibody heavy chain or antibody light chain). In the disclosure, percent identity between the nucleic acid sequences described may include any discrete subrange of the percent identity ranges recited above (e.g., any range of integer values within a particular range or discrete subvalues within a particular range).

"Percent identity" between a query amino acid sequence and a subject amino acid sequence is the "Identities" value, expressed as a percentage, that is calculated by the BLASTP algorithm when a subject amino acid sequence has 100% query coverage with a query amino acid sequence after a pair-wise BLASTP alignment is performed. Such pair-wise BLASTP alignments between a query amino acid sequence and a subject amino acid sequence are performed by using the default settings of the BLASTP algorithm available on the National Center for Biotechnology Institute's website with the filter for low complexity regions turned off. Importantly, a query sequence may be described by an amino acid sequence identified in one or more claims herein.

The amino acid sequences which may be useful, and included, in compositions and related methods of the disclosure may have between about 85% to about 100%, about 90% to about 100%, about 95% to about 100%, about 91%, about 92%, about 93%, about 94%, about 95%, about 96%, about 97%, about 98%, about 99% and about 100% identity to the amino acid sequences identified in the disclosure (e.g., to an antibody heavy chain or antibody light chain). In the disclosure, percent identity between the amino acid sequences described may includes any discrete subrange of the percent identity ranges recited above (e.g., any range of integer values within a particular range or discrete subvalues within a particular range).

The terms "peptide", "polypeptide", "protein" and "peptide chain" each refer to a molecule comprising two or more amino acid residues. A peptide may be monomeric or polymeric.

It is well recognized in the art that certain amino acid substitutions are regarded as being "conservative" Amino acids are divided into groups based on common side-chain properties and substitutions within groups that maintain all or substantially all of the binding affinity of the antigen binding protein are regarded as conservative substitutions. See Table 15. The antigen binding proteins disclosed herein can comprise such "conservative" amino acid substitutions.

TABLE 15

| Side chain | Members |
|---|---|
| Hydrophobic | met, ala, val, leu, ile |
| Neutral hydrophilic | cys, ser, thr |
| Acidic | asp, glu |
| Basic | asn, gln, his, lys, arg |
| Residues that influence chain orientation | gly, pro |
| Aromatic | trp, tyr, phe |

The term "pharmaceutical composition" as used herein means a composition suitable for administration to a patient.

The pharmaceutical compositions described herein may comprise purified preparations of an antibody as described herein.

For example, the pharmaceutical preparation may comprise a purified preparation of an antibody as described herein in combination with a pharmaceutically acceptable carrier.

Typically, such pharmaceutical compositions comprise a pharmaceutically acceptable carrier as known and called for by acceptable pharmaceutical practice. Examples of such carriers include sterilized carriers, such as saline, Ringers solution, or dextrose solution, optionally buffered with suitable buffers to a pH within a range of 5 to 8.

Pharmaceutical compositions may be administered by injection or infusion (e.g., intravenous, intraperitoneal, intradermal, subcutaneous, intramuscular, or intraportal). Such compositions are suitably free of visible particulate matter. Pharmaceutical compositions may comprise between 1 mg to 10 g of antigen binding protein, for example, between 5 mg and 1 g of antigen binding protein. Alternatively, the composition may comprise between 5 mg and 500 mg of antigen binding protein, for example, between 5 mg and 50 mg.

Methods for the preparation of such pharmaceutical compositions are well known to those skilled in the art. Pharmaceutical compositions may comprise between 1 mg to 10 g of antigen binding protein in unit dosage form, optionally together with instructions for use. Pharmaceutical compositions may be lyophilized (freeze dried) for reconstitution prior to administration according to methods well known or apparent to those skilled in the art. Where antibodies have an $IgG_1$ isotype, a chelator of copper, such as citrate (e.g., sodium citrate) or EDTA or histidine, may be added to the pharmaceutical composition to reduce the degree of copper-mediated degradation of antibodies of this isotype. Pharmaceutical compositions may also comprise a solubilizer, such as arginine, a surfactant/anti-aggregation agent such as polysorbate 80, and an inert gas such as nitrogen to replace vial headspace oxygen.

The term "therapeutically effective amount" as used herein means an amount of an agent (such as an antibody or a pharmaceutical composition), which provides a therapeutic benefit in the treatment or management of one or more symptoms of a condition to be treated (such as asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis). Examples of such treatment or management of one or more symptoms of asthma—including asthma, mild asthma, moderate asthma, severe asthma, mild eosinophilic asthma, moderate eosinophilic asthma, severe eosinophilic asthma, uncontrolled eosinophilic asthma, eosinophilic asthma and sub-eosinophilic asthma—include 1) a reduction of the frequency of asthma exacerabations; 2) a reduction in the time to first clinically significant exacerbation requiring oral or systemic corticosteroids, hospitalisation, and/or emergency department (ED) visits; 3) a reduction in the frequency of exacerbations requiring hospitalization (including intubation and admittance to an intensive care unit) or ED visits; 4) a reduction in the time to first exacerbation requiring hospitalization or ED visit; 5) a change from baseline in clinic pre-bronchodilator $FEV_1$; 6) a change from baseline in clinic post-bronchodilator $FEV_1$; 7) a change from baseline in an Asthma Control Questionnaire (ACQ) score; 8) improved lung function as assessed by spirometry (e.g., vital capacity (VC), forced vital capacity (FVC), forced expiratory volume (FEV) at timed intervals of 0.5, 1.0 ($FEV_1$), 2.0, and 3.0 seconds, forced expiratory flow 25-75% (FEF 25-75) and maximal voluntary ventilation (MVV) total lung capacity, ideal volume, residual volume, expiratory reserve volume, inspiratory reserve volume, inspiratory capacity, inspiratory vital capacity, vital capacity, functional residual capacity, residual volume expressed as percent of total lung capacity, alveolar gas volume, actual volume of the lung including the volume of the conducting airway, forced vital capacity, etc.); and 9) a reduction in asthma exacerbations requiring steroids for control (such as oral steroids or steroids—like prednisone, prednisolone etc.—administered by any route). Such a reduction in asthma exacerbations requiring steroids for control may be an approximately 50% reduction in exacerbations requiring steroids (e.g., oral steroids).

Therapeutically effective amounts and treatment regimes are generally determined empirically and may be dependent on factors, such as the age, weight, and health status of the patient and disease or disorder to be treated. Such factors are within the purview of the attending physician.

The dosage of antigen binding protein administered to a subject is generally between 1 μg/kg to 150 mg/kg, between 0.1 mg/kg and 100 mg/kg, between 0.5 mg/kg and 50 mg/kg, between 1 and 25 mg/kg, between about 0.3 mg/kg and about 3 mg/kg or between 1 and 10 mg/kg of the subject's body weight. For example, the dose may be 10 mg/kg, 30 mg/kg, or 60 mg/kg. The dose may also be from 10 mg/kg to 110 mg/mg 15 mg/kg to 25 mg/kg or 15 mg/kg to 100 mg/kg. The antigen binding protein may be administered, for example, parenterally, subcutaneously, intravenously, or intramuscularly. Doses may also be administered on a per subject basis such as about 20 mg per subject to about 750 mg per subject, about 75 mg per subject to about 750 mg per subject, about 20 mg per subject to about 200 mg per subject. The dose may be any discrete subrange with these dosage ranges. For example, the dose may also be administered subcutaneously on a per subject basis such as about 100 mg per subject (e.g., once every four weeks), or 300 mg per subject (or other doses administered may be subcutaneously with provided approximately the same, or comparable, bioavailability is achieved as with intravenous administration—e.g., three doses of 100 mg per subject to achieve a total dose administered subcutaneously of 300 mg per subject).

It is preferred that pediatric subjects weighing less than 40 kg receive a dose of 40 mg and that pediatric subjects weighing greater than or equal to 40 kg receive a dose of 100 mg of mepolizumab. It is further preferred that such doses be administered subcutaneously.

Ranges provided herein, of any type, include all values within a particular range described and values about an endpoint for a particular range.

If desired, the effective daily dose of an antibody or antigen binding protein of the disclosure (e.g., as a pharmaceutical composition) may be administered as two, three, four, five, six or more doses administered separately at appropriate intervals throughout the day, optionally, in unit dosage forms. For example a dose of 100 mg to be administered to a pediatric subject weighing greater than or equal to 40 kg may be administered as two separate doses (e.g., subcutaneous injections) of 0.5 ml each of which contains 50 mg of mepolizumab.

The administration of a dose may be by slow continuous infusion over a period of from 2 to 24 hours, such as of from 2 to 12 hours, or from 2 to 6 hours. Such an administration may result in reduced side effects.

The administration of a dose may be repeated one or more times as necessary, for example, three times daily, once every day, once every 2 days, once a week, once a every 14 days, once a month, once every 3 months, once every 4 months, once every 6 months, or once every 12 months. The antigen binding proteins may be administered by maintenance therapy, for example once a week for a period of 6 months or more. The antigen binding proteins may be administered by intermittent therapy, for example, for a period of 3 to 6 months and then no dose for 3 to 6 months, followed by administration of antigen binding proteins again for 3 to 6 months, and so on, in a cycle.

For example, the dose may be administered subcutaneously, once every 14 or 28 days, in the form of multiple doses on each day of administration. In one embodiment, the dosage of the composition is 100 mg once every 4 weeks (28 days).

The antigen binding protein may be administered to the subject in such a way as to target therapy to a particular site (e.g., upper arm or thigh etc.).

The antigen binding protein in the methods of the disclosure may be used in combination with one or more other therapeutically active agents, such as antibodies or small molecule inhibitors By the term "treating" and grammatical variations thereof as used herein, is meant therapeutic therapy. In reference to a particular condition, treating means: (1) to ameliorate the condition of one or more of the biological manifestations of the condition, (2) to interfere with a) one or more points in the biological cascade that leads to or is responsible for the condition or b) one or more of the biological manifestations of the condition, (3) to alleviate one or more of the symptoms, effects or side effects associated with the condition or treatment thereof, (4) to slow the progression of the condition or one or more of the biological manifestations of the condition or (5) to prevent the onset of one or more of the biological manifestations of the condition. Prophylactic therapy is also contemplated thereby. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

The terms "individual", "subject" and "patient" are used herein interchangeably. The subject is typically a human. The subject may also be a mammal, such as a mouse, rat, or primate (e.g., a marmoset or monkey). The subject can be a non-human animal. The antigen binding proteins, compositions and methods of the disclosure also have veterinary use. The subject to be treated may be a farm animal, for example, a cow or bull, sheep, pig, ox, goat or horse, or may be a domestic animal such as a dog or cat. The animal may be any age, or a mature adult animal.

Treatment can be therapeutic, prophylactic or preventative. The subject will be one who is in need thereof. Those in need of treatment may include individuals already suffering from a particular medical disease, in addition to those who may develop the disease in the future.

Thus, the methods, antigen binding proteins and compositions of the disclosure described herein can be used for prophylactic treatment or preventative treatment if specified. In this case, methods, antigen binding proteins and compositions of the disclosure can be used to prevent or delay the onset of one or more aspects or symptoms of a disease. The subject can be asymptomatic. The subject may have a genetic predisposition to the disease. A prophylactically effective amount of the antigen binding protein is administered to such an individual. A prophylactically effective amount is an amount which prevents or delays the onset of one or more aspects or symptoms of a disease described herein.

The methods, antigen binding proteins and compositions of the disclosure need not affect a complete cure, or eradicate every symptom or manifestation of the disease to constitute a viable therapeutic treatment. As is recognised in the art, drugs employed as therapeutic agents in methods of treatment may reduce the severity of a given disease state, but need not abolish every manifestation of the disease to be regarded as useful therapeutic agents. Similarly, a prophylactically administered treatment need not be completely effective in preventing the onset of a disease in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur (for example by delaying the onset of the disease) or worsen in a subject, is sufficient.

As used herein "Area Under the Curve" or "AUC" is the area under the curve in a plot of the concentration of a substance in plasma against time. AUC can be a measure of the integral of the instantaneous concentrations during a time interval and has the units mass*time/volume. AUC is typically calculated by the trapezoidal method (e.g., linear, linear-log). AUC is usually given for the time interval zero to infinity, and other time intervals are indicated (for example AUC (t1,t2) where t1 and t2 are the starting and finishing times for the interval). Thus, as used herein "$AUC_{0-24}$" refers to an AUC over a 24 hour period and AUC(0-inf) refers to AUC from over an infinite time period.

As used herein "Tmax" refers to the observed time for reaching the maximum concentration of a substance in plasma of a mammal after administration of that substance to the mammal.

As used herein "maximum plasma concentration" or "Cmax" means the highest observed concentration of a substance (e.g., an antibody) in mammalian plasma after administration of the substance to the mammal.

As used herein "maximum plasma concentration at steady state" or "Cmax SS" means the maximum concentration in plasma at steady state as determined by pharmacokinetic modelling and is a population estimate for Cmax at steady state obtained by population PK methods. Steady state refers to the situation where the overall intake of a drug is fairly in dynamic equilibrium with its elimination. Typically, it is generally considered that steady state is reached when a time of 4 to 5 times the half-life for a drug after regular dosing of the drug is started.

As used herein "serum or plasma half life" refers to the time required for half the quantity of a substance administered to a mammal to be metabolized or eliminated from the serum or plasma of the mammal by normal biological processes.

One aspect of the disclosure is a method of treating a disease in a pediatric subject comprising the steps of: a) identifying a pediatric subject weighing less than 40 kg with a disease selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis; and b) administering a therapeutically effective amount of an antibody comprising the heavy chain amino acid sequence shown in SEQ ID NO: 1 and the light chain amino acid sequences shown in SEQ ID NO: 2 subcutaneously to the pediatric subject wherein the therapeutically effective amount of the antibody provides a maximum plasma concentration (Cmax) of the antibody that is about 10.1960±0.3345 μg/mL and an Area Under the Curve [0-infinity] value that is about 454.39±15.8876 m*day/mL; whereby the disease in the pediatric subject is treated.

In one embodiment of the methods of the disclosure the therapeutically effective amount of the antibody is about 40 mg.

In another embodiment of the methods of the disclosure the antibody is administered about once every month.

In another embodiment of the methods of the disclosure the pediatric subject has an absolute blood eosinophil count selected from the group consisting of greater than or equal to 150 cells per µL and greater than or equal to 300 cells per µL.

In another embodiment of the methods of the disclosure the pediatric subject is one selected from the group consisting of a pre-term newborn child, a term newborn child, a child 28 day to 11 months old, a child 12 months to 23 months old, a child 2 years to 6 years old, a child 16 years old to 12 years old, a child 6 years old to less than 18 years old and a child 12 to 18 years old.

In another embodiment of the methods of the disclosure the pediatric subject is about 6 years of age to about 12 years of age inclusive.

In another embodiment of the methods of the disclosure the pediatric subject has severe eosinophilic asthma.

In another embodiment of the methods of the disclosure the pediatric subject has a treatment outcome selected from the group consisting of a decrease in absolute blood eosinophil count relative to an absolute blood eosinophil count prior to administration of the antibody, a decreased score on the Asthma Control Questionnaire 7 scale relative to a score on the Asthma Control Questionnaire 7 scale prior to administration of the antibody and a decreased score on the Childhood Asthma Control Test relative to a score on the Childhood Asthma Control Test prior to administration of the antibody.

In another embodiment of the methods of the disclosure the antibody is administered by a safety syringe or an autoinjector.

Another aspect of the disclosure is a method of treating a disease in a pediatric subject comprising the steps of: a) identifying a pediatric subject weighing greater than or equal to 40 kg with a disease selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis; and b) administering a therapeutically effective amount of an antibody comprising the heavy chain amino acid sequence shown in SEQ ID NO: 1 and the light chain amino acid sequences shown in SEQ ID NO: 2 subcutaneously to the pediatric subject wherein the therapeutically effective amount of the antibody provides a maximum plasma concentration (Cmax) of the antibody that is about 16.3412±0.6364 µg/mL and an Area Under the Curve [0-infinity] value that is about 675.20±35.8980 m*day/mL; whereby the disease in the pediatric subject is treated.

In another embodiment of the methods of the disclosure the therapeutically effective amount of the antibody is about 100 mg.

Another aspect of the disclosure is a method of decreasing an absolute blood eosinophil count in a pediatric subject comprising the steps of: a) identifying a pediatric subject weighing less than 40 kg having a condition selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis and atopic dermatitis; and b) administering a therapeutically effective amount of an antibody comprising the heavy chain amino acid sequence shown in SEQ ID NO: 1 and the light chain amino acid sequences shown in SEQ ID NO: 2 subcutaneously to the pediatric subject wherein the therapeutically effective amount of the antibody provides a maximum plasma concentration (Cmax) of the antibody that is about 10.1960±0.3345 µg/mL and an Area Under the Curve [0-infinity] value that is about 454.39±15.8876 µg*day/mL; whereby the absolute blood eosinophil count in the pediatric subject is decreased.

Another aspect of the disclosure is a method of decreasing an absolute blood eosinophil count in a pediatric subject comprising the steps of: a) identifying a pediatric subject weighing greater than or equal to 40 kg having a condition selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis and atopic dermatitis; and b) administering a therapeutically effective amount of an antibody comprising the heavy chain amino acid sequence shown in SEQ ID NO: 1 and the light chain amino acid sequences shown in SEQ ID NO: 2 subcutaneously to the pediatric subject wherein the therapeutically effective amount of the antibody provides a maximum plasma concentration (Cmax) of the antibody that is about 16.3412±0.6364 µg/mL and an Area Under the Curve [0-infinity] value that is about 675.20±35.8980 µg*day/mL; whereby the absolute blood eosinophil count in a pediatric subject is decreased.

Another embodiment of the disclosure is a composition according to the disclosure and/or methods of the disclosure for use in therapy.

Another embodiment of the disclosure is a composition according to the disclosure and/or methods of the disclosure for use in treating asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis.

Another aspect of the disclosure is a composition for treating a disease selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis in a pediatric subject weighing less than 40 kg wherein said composition comprises an antibody comprising the heavy chain amino acid sequence shown in SEQ ID NO: 1 and the light chain amino acid sequences shown in SEQ ID NO: 2 and a therapeutically effective amount of the antibody administered subcutaneously to the pediatric subject provides a maximum plasma concentration (Cmax) of the antibody that is about 10.1960±0.3345 μg/mL and an Area Under the Curve [0-infinity] value that is about 454.39±15.8876 m*day/mL.

In another embodiment of the composition of the disclosure the therapeutically effective amount of the antibody is about 40 mg.

Another aspect of the disclosure is a composition for treating a disease selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis in a pediatric subject weighing greater than or equal to 40 kg wherein said composition comprises an antibody comprising the heavy chain amino acid sequence shown in SEQ ID NO: 1 and the light chain amino acid sequences shown in SEQ ID NO: 2 and a therapeutically effective amount of the antibody administered subcutaneously to the pediatric subject provides a maximum plasma concentration (Cmax) of the antibody that is about 16.3412±0.6364 μg/mL and an Area Under the Curve [0-infinity] value that is about 675.20±35.8980 m*day/mL.

In another embodiment of the composition of the disclosure the therapeutically effective amount of the antibody is about 100 mg.

Another aspect of the disclosure is a composition for decreasing an absolute blood eosinophil count in a pediatric subject weighing less than 40 kg, wherein said pediatric subject has a disease selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis; and said composition comprises an antibody comprising the heavy chain amino acid sequence shown in SEQ ID NO: 1 and the light chain amino acid sequences shown in SEQ ID NO: 2; and a therapeutically effective amount of the antibody administered subcutaneously to the pediatric subject provides a maximum plasma concentration (Cmax) of the antibody that is about 10.1960±0.3345 μg/mL and an Area Under the Curve [0-infinity] value that is about 454.39±15.8876 μg*day/mL.

Another aspect of the disclosure is a composition for decreasing an absolute blood eosinophil count in a pediatric subject weighing greater than or equal to 40 kg, wherein said pediatric subject has a disease selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis; and said composition comprises an antibody comprising the heavy chain amino acid sequence shown in SEQ ID NO: 1 and the light chain amino acid sequences shown in SEQ ID NO: 2; and a therapeutically effective amount of the antibody provides a maximum plasma concentration (Cmax) of the antibody that is about 16.3412±0.6364 μg/mL and an Area Under the Curve [0-infinity] value that is about 675.20±35.8980 μg*day/mL.

In one embodiment of the methods of the disclosure the amount of antigen binding protein is about 2 mg to about 600 mg. For example, the amount of antigen binding protein (e.g., antibody) may be a 2 mg, 10 mg, 30 mg, 100 mg, 300 mg or 600 mg dose.

In one embodiment of the method of the disclosure the antigen binding protein is administered once every 3 months or once every 6 months.

One embodiment is a method of the disclosure wherein the pharmaceutically effective carrier comprises an aqueous liquid formulation at about pH 5.5 to about pH 6.0 containing about 40 mM histidine, about 180 mM trehalose, about 100 mM arginine, about 8 mM methionine, about 0.02% weight of polysorbate 80 to volume and about 0.05 mM EDTA.

The compositions of the disclosure and those comprising the antibody, or antigen binding protein of the disclosure may further comprise a buffering agent selected from the group consisting of sodium phosphate dibasic heptahydrate, phosphate, citric acid, citrate, sodium phosphate, potassium phosphate, sodium citrate, and histidine, providing a pH of between 6.8 and 7.2 or a pH of from pH 6.2 to pH 6.6 with a pH value of 6.3 being preferred. The buffer in the compositions of the disclosure may be present in the range from about 10-30 mM, about 10-20 mM, about 20 mM or about 15.5 mM. For example, the buffer in the compositions of the disclosure is present at about 20 mM, or at about 15.5 mM sodium phosphate dibasic heptahydrate. These compositions are useful in the methods of the disclosure.

The compositions of the disclosure may comprise sodium phosphate dibasic heptahydrate and citric acid buffering agents providing a pH of from 6.2 to 6.6 inclusive with a pH value of 6.3 being preferred. The sodium phosphate dibasic heptahydrate buffering agent may be present in the range from about 15-16.4 mM and the citric acid buffering agent may be present in the range from about 3.8-4.9 mM. For example, the compositions of the disclosure may comprise about 15.5 mM sodium phosphate dibasic heptahydrate and about 4.5 mM citric acid monohydrate.

The compositions of the disclosure may further comprise a sugar. The compositions of the disclosure may further comprise sucrose. Sucrose may be present in the compositions of the disclosure in the range from about 5-20%; about 10-15%, about 11-13% or at about 12% weight by volume.

The compositions of the disclosure may further comprise polysorbate 80. Polysorbate 80 may be present in the range from about 0.01-0.1% weight by volume. For example, polysorbate 80 may be present in the compositions of the disclosure at about 0.02% weight by volume, or at about 0.05% weight by volume.

The compositions of the disclosure may further comprise EDTA. EDTA may be present in the range from about 0.01-0.1 mM. For example, EDTA may be present at about 0.05 mM.

In one embodiment, the compositions of the disclosure further comprise 20 mM sodium phosphate dibasic heptahydrate, 12% weight of sucrose to volume and 0.05% weight of polysorbate 80 to volume.

In another embodiment, the compositions of the disclosure further comprise 15.5 mM sodium phosphate dibasic, 3.9 mM citric acid monohydrate, 12% weight of sucrose to volume, 0.02% weight of polysorbate 80 to volume and 0.05 mM EDTA.

The compositions of the disclosure may comprise an aqueous liquid formulation at pH 6.2 containing 16.1 mM sodium phosphate dibasic heptahydrate, 3.9 mM citric acid monohydrate, 12% weight of sucrose to volume, 0.02% weight of polysorbate 80 to volume and 0.05 mM EDTA.

The compositions of the disclosure may comprise an aqueous liquid formulation at pH 6.2 containing 15.2 mM sodium phosphate dibasic heptahydrate, 4.8 mM citric acid monohydrate, 12% weight of sucrose to volume, 0.02% weight of polysorbate 80 to volume and 0.05 mM EDTA.

The compositions of the disclosure may comprise an aqueous liquid formulation at pH 6.4 containing 15.8 mM sodium phosphate dibasic heptahydrate, 4.2 mM citric acid monohydrate, 12% weight of sucrose to volume, 0.02% weight of polysorbate 80 to volume and 0.05 mM EDTA.

The compositions of the disclosure may comprise an aqueous liquid formulation at pH 6.6 containing 16.3 mM sodium phosphate dibasic heptahydrate, 3.7 mM citric acid monohydrate, 12% weight of sucrose to volume, 0.02% weight of polysorbate 80 to volume and 0.05 mM EDTA.

The compositions of the disclosure may comprise an aqueous liquid formulation at pH 6.3 containing 15.5 mM sodium phosphate dibasic heptahydrate, 4.5 mM citric acid monohydrate, 12% weight of sucrose to volume, 0.02% weight of polysorbate 80 to volume and 0.05 mM EDTA. Importantly, the tangential filtration and ultrafiltration exchange step of a production process may be adjusted to produce the compositions of the disclosure, such as a composition of the disclosure comprising 15.5 mM sodium phosphate dibasic heptahydrate, 4.5 mM citric citric acid monohydrate, 12% weight to volume sucrose, 0.02% weight to volume polysorbate 80, 0.05 mM EDTA at a pH of 6.3—or other such liquid formulations.

The compositions of the disclosure may comprise a purified preparation of a monoclonal antibody and a buffering agent, wherein the composition is at a pH from 6.8 to 7.2, wherein the buffering agent is histidine, phosphate, citric acid, citrate or a salt thereof.

In the compositions of the disclosure the buffering agent may be at least one selected from the group consisting of sodium phosphate dibasic heptahydrate, phosphate, citric acid and citrate.

In the compositions of the disclosure the buffering agent may be sodium phosphate, potassium phosphate, or sodium citrate.

The compositions of the disclosure may comprise a sugar, a carbohydrate and/or a salt.

The compositions of the disclosure may also comprise sucrose or trehalose.

The compositions of the disclosure may also comprise a purified preparation of a monoclonal antibody and a buffering agent, wherein the composition is at a pH from 6.8 to 7.2, wherein the buffering agent is phosphate or a salt thereof.

The composition of the disclosure may also comprise one selected from a first formulation of 20 mM sodium phosphate dibasic heptahydrate, 12% weight of sucrose to volume and 0.05% weight of polysorbate 80 to volume; and a second formulation of 15.5 mM sodium phosphate dibasic heptahydrate, 3.9 mM citric acid monohydrate, 12% weight of sucrose to volume, 0.02% weight of polysorbate 80 to volume and 0.05 mM EDTA; and a third formulation of 26 mM sodium phosphate dibasic heptahydrate, 15% weight of sucrose to volume and 0.065% weight of polysorbate 80 to volume. The composition may be at a pH between about 6.8 to about 7.2, about 6.1 to about 6.5 or about 6 to about 6.6.

The compositions described herein may be produced by any number of conventional techniques. For example, the compositions may be expressed in and purified from recombinant expression systems. In one embodiment, the composition is produced by a method of culturing a host cell under conditions suitable for expression of a polypeptide comprising SEQ ID NO: 1 and SEQ ID NO:2, wherein the composition is expressed, and optionally purified, and optionally formulated within a pharmaceutical composition.

A number of different expression systems and purification regimes can be used to produce the compositions. Generally, host cells are transformed with a recombinant expression vector encoding the antibody. A wide range of host cells can be employed, including Eukaryotic cell lines of mammalian origin (e.g., CHO, Perc6, HEK293, HeLa, NS0). Suitable host cells include mammalian cells such as CHO (e.g., CHOK1 and CHO-DG44).

The host cell may be an isolated host cell. The host cell is usually not part of a multicellular organism (e.g., plant or animal). The host cell may be a non-human host cell.

Appropriate cloning and expression vectors for use with eukaryotic or mammalian cellular hosts and methods of cloning are known in the art.

The cells may be cultured under conditions that promote expression of the antibody. For example, a production bioreactor is used to culture the cells. The production bioreactor volume may be: (i) about 20,000 litres, about 10,000 litres; about 5,000 litres; about 2,000 litres; about 1,000 litres; or about 500 litres; or (ii) between 500 and 20,000 litres; between 500 and 10,000 litres; between 500 and 5,000 litres; between 1,000 and 10,000 litres, or between 2,000 and 10,000 litres. For example, the cells may be cultured in a production bioreactor at a pH of about 6.75 to pH 7.00. Alternatively, the cells may be cultured in a production bioreactor for about 12 to about 18 days. Alternatively, the cells may be cultured in a production bioreactor at a pH of about 6.75 to pH 7.00, for about 12 to about 18 days. This culture step may help to control the level of deamidated antibody variants, for example, to reduce the level of deamidated antibody variants.

The composition may be recovered and purified by conventional protein purification procedures. For example, the composition may be harvested directly from the culture medium. Harvest of the cell culture medium may be via clarification, for example by centrifugation and/or depth filtration. Recovery of the composition is followed by purification to ensure adequate purity.

One or more chromatography steps may be used in purification, for example one or more chromatography resins; and/or one or more filtration steps. For example affinity chromatography using resins, such as protein A, G, or L may be used to purify the composition. Alternatively, or in addition to, an ion-exchange resin such as a cation-exchange may be used to purify the composition. Alternatively, or in addition to, a hydrophobic interaction chromatographic resin may be used to purify the composition. Alternatively the purification steps comprise: an affinity chromatography resin step, followed by a cation-exchange resin step, followed by a hydrophobic interaction chromatographic resin step.

For example, the harvest is placed in contact with a protein A resin. The solution comprising the composition may be eluted from the protein A resin and treated at pH 3.3 to 3.7 for 15 to 240 minutes. This protein A resin step may help to control the level of aggregated antibody variants, for example, to reduce the level of aggregated antibody variants.

The solution comprising the composition may then be further clarified by depth filtration and/or dual layer filtration.

Alternatively, or in addition to, an anion exchange resin may be used. The solution comprising the composition may be placed in contact with an anion exchange resin (for example Q-SEPHAROSE™ Fast Flow anion exchange chromatography) at a load pH of 8.3 to 8.7. The solution comprising the composition may be eluted from the anion exchange resin and held for 96 hours or less. This anion exchange resin step may help to control the level of deamidated antibody variants, for example, to reduce the level of deamidated antibody variants.

Optionally, guanidine and/or ammonium sulphate may be added to the solution comprising the composition, and held for 15 to 240 minutes.

Alternatively, or in addition to, a hydrophobic interaction chromatographic resin may be used. The solution comprising the composition may be placed in contact with a hydrophobic interaction chromatographic resin (e.g., phenyl SEPHAROSE™ fast flow chromatography) at a load ratio of 12 to 27 g protein/L resin. For example, the solution comprising the composition may be eluted using an elution gradient volume (bed volumes; BV) of about 9 to about 11. An elution peak cut stop (% of maximum peak height) of about 17 to about 23 may be used during elution from the hydrophobic interaction chromatographic resin. This hydrophobic interaction chromatographic resin step may help to control the level of aggregated antibody variants, for example, to reduce the level of aggregated antibody variants.

The solution comprising the composition may then be filtered to remove virus. The solution comprising the composition may then be formulated at an antibody concentration of about 76 g protein/L to about 82 g protein/L, or to about 100 g protein/L. The solution comprising the composition may be filled into containers and frozen. Aliquots of the solution comprising the composition may be lyophilized Lyophilizate may be reconstituted by the addition of water to produce a composition comprising 75 mg/L of protein, the monoclonal anti-IL-5 antibody and 20 mM sodium phosphate dibasic heptahydrate, 12% weight of sucrose to volume and 0.05% weight of polysorbate 80 to volume at a pH of from about 6.8 to about 7.2.

The methods of the disclosure and the compositions of the disclosure may also be used to achieve a lower steroid dose or a lower dose of other drugs—such as those shown in FIG. 2 or Table 4.

In summary, the disclosure includes:

In one aspect, a method of treating a disease in a pediatric subject comprising the steps of: a) identifying a pediatric subject weighing less than 40 kg with a disease selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis; and b) administering a therapeutically effective amount of an antibody comprising the heavy chain amino acid sequence shown in SEQ ID NO: 1 and the light chain amino acid sequences shown in SEQ ID NO: 2 subcutaneously to the pediatric subject wherein the therapeutically effective amount of the antibody provides a maximum plasma concentration (Cmax) of the antibody that is about $10.1960 \pm 0.3345$ µg/mL and an Area Under the Curve [0-infinity] value that is about $454.39 \pm 15.8876$ µg*day/mL; whereby the disease in the pediatric subject is treated.

Another aspect of the disclosure is a method of treating a disease in a pediatric subject comprising the steps of: a) identifying a pediatric subject weighing greater than or equal to 40 kg with a disease selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis; and b) administering a therapeutically effective amount of an antibody comprising the heavy chain amino acid sequence shown in SEQ ID NO: 1 and the light chain amino acid sequences shown in SEQ ID NO: 2 subcutaneously to the pediatric subject wherein the therapeutically effective amount of the antibody provides a maximum plasma concentration (Cmax) of the antibody that is about $16.3412 \pm 0.6364$ µg/mL and an Area Under the Curve [0-infinity] value that is about $675.20 \pm 35.8980$ m*day/mL; whereby the disease in the pediatric subject is treated.

Another aspect of the disclosure is a method of decreasing an absolute blood eosinophil count in a pediatric subject comprising the steps of: a) identifying a pediatric subject weighing less than 40 kg having a condition selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis and atopic dermatitis; and b) administering a therapeutically effective amount of an antibody comprising the heavy chain amino acid sequence shown in SEQ ID NO: 1 and the light chain amino acid sequences shown in SEQ ID NO: 2 subcutaneously to the pediatric subject wherein the therapeutically effective amount of the antibody provides a maximum plasma concentration (Cmax) of the antibody that is about $10.1960 \pm 0.3345$ µg/mL and an Area Under the Curve [0-infinity] value that is about $454.39 \pm 15.8876$ µg*day/mL; whereby the absolute blood eosinophil count in the pediatric subject is decreased.

Another aspect of the disclosure is a method of decreasing an absolute blood eosinophil count in a pediatric subject comprising the steps of: a) identifying a pediatric subject weighing greater than or equal to 40 kg having a condition selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis and atopic dermatitis; and b) administering a therapeutically effective amount of an antibody comprising the heavy chain amino acid sequence shown in SEQ ID NO: 1 and the light chain amino acid sequences shown in SEQ ID NO: 2 subcutaneously to the pediatric subject wherein the therapeutically effective amount of the antibody provides a maximum plasma concentration (Cmax) of the antibody that is about 16.3412±0.6364 µg/mL and an Area Under the Curve [0-infinity] value that is about 675.20±35.8980 µg*day/mL; whereby the absolute blood eosinophil count in a pediatric subject is decreased.

In one embodiment of the disclosed methods the therapeutically effective amount of the antibody is about 40 mg.

In another embodiment of the disclosed methods of the antibody is administered about once every month.

In another embodiment of the disclosed methods the pediatric subject has an absolute blood eosinophil count selected from the group consisting of greater than or equal to 150 cells per µL and greater than or equal to 300 cells per µL.

In another embodiment of the disclosed methods the pediatric subject is one selected from the group consisting of a pre-term newborn child, a term newborn child, a child 28 day to 11 months old, a child 12 months to 23 months old, a child 2 years to 6 years old, a child 16 years old to 12 years old, a child 6 years old to less than 18 years old and a child 12 to 18 years old.

In another embodiment of the disclosed methods the pediatric subject is about 6 years of age to about 12 years of age inclusive.

In another embodiment of the disclosed methods the pediatric subject has severe eosinophilic asthma.

In another embodiment of the disclosed methods the pediatric subject has a treatment outcome selected from the group consisting of a decrease in absolute blood eosinophil count relative to an absolute blood eosinophil count prior to administration of the antibody, a decreased score on the Asthma Control Questionnaire 7 scale relative to a score on the Asthma Control Questionnaire 7 scale prior to administration of the antibody and a decreased score on the Childhood Asthma Control Test relative to a score on the Childhood Asthma Control Test prior to administration of the antibody.

In another embodiment of the disclosed methods the antibody is administered by a safety syringe or an autoinjector.

In another embodiment of the disclosed methods the therapeutically effective amount of the antibody is about 100 mg.

Another embodiment of the invention is a composition according to any one aspect or embodiment of the methods of the disclosure for use in therapy.

Another embodiment of the invention is a composition according to any one aspect or embodiment of the methods of the disclosure for use in treating asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis.

Another aspect of the disclosure is a composition for treating a disease selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis in a pediatric subject weighing less than 40 kg wherein said composition comprises an antibody comprising the heavy chain amino acid sequence shown in SEQ ID NO: 1 and the light chain amino acid sequences shown in SEQ ID NO: 2 and a therapeutically effective amount of the antibody administered subcutaneously to the pediatric subject provides a maximum plasma concentration (Cmax) of the antibody that is about 10.1960±0.3345 µg/mL and an Area Under the Curve [0-infinity] value that is about 454.39±15.8876 m*day/mL.

Another aspect of the disclosure is a composition for treating a disease selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis in a pediatric subject weighing greater than or equal to 40 kg wherein said composition comprises an antibody comprising the heavy chain amino acid sequence shown in SEQ ID NO: 1 and the light chain amino acid sequences shown in SEQ ID NO: 2 and a therapeutically effective amount of the antibody administered subcutaneously to the pediatric subject provides a maximum plasma concentration (Cmax) of the antibody that is about 16.3412±0.6364 µg/mL and an Area Under the Curve [0-infinity] value that is about 675.20±35.8980 m*day/mL. Another embodiment is a composition of the disclosure wherein the therapeutically effective amount of the antibody is about 40 mg.

Another aspect of the disclosure is a composition for decreasing an absolute blood eosinophil count in a pediatric subject weighing less than 40 kg, wherein said pediatric subject has a disease selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis; and said composition comprises an antibody comprising the heavy chain amino acid sequence shown in SEQ ID NO: 1 and the light chain amino acid sequences shown in SEQ ID NO: 2; and a therapeutically effective amount of the antibody administered subcutaneously to the pediatric subject provides a maximum plasma concentration (Cmax) of the antibody that is about 10.1960±0.3345 µg/mL and an Area Under the Curve [0-infinity] value that is about 454.39±15.8876 µg*day/mL.

A composition for decreasing an absolute blood eosinophil count in a pediatric subject weighing greater than or equal to 40 kg, wherein said pediatric subject has a disease selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis; and said composition comprises an antibody comprising the heavy chain amino acid sequence shown in SEQ ID NO: 1 and the light chain amino acid sequences shown in SEQ ID NO: 2; and a therapeutically effective amount of the antibody provides a maximum plasma concentration (Cmax) of the antibody that is about 16.3412±0.6364 μg/mL and an Area Under the Curve [0-infinity] value that is about 675.20±35.8980 μg*day/mL.

Another embodiment is a composition of the disclosure wherein the antibody is administered about once every month.

Another embodiment is a composition of the disclosure wherein the pediatric subject has an absolute blood eosinophil count selected from the group consisting of greater than or equal to 150 cells per μL and greater than or equal to 300 cells per μL.

Another embodiment is a composition of the disclosure wherein the pediatric subject is one selected from the group consisting of a pre-term newborn child, a term newborn child, a child 28 day to 11 months old, a child 12 months to 23 months old, a child 2 years to 6 years old, a child 16 years old to 12 years old, a child 6 years old to less than 18 years old and a child 12 to 18 years old.

Another embodiment is a composition of the disclosure wherein the pediatric subject is about 6 years of age to about 12 years of age inclusive.

Another embodiment is a composition of the disclosure wherein the pediatric subject has severe eosinophilic asthma.

Another embodiment is a composition of the disclosure wherein the pediatric subject has a treatment outcome selected from the group consisting of a decrease in absolute blood eosinophil count relative to an absolute blood eosinophil count prior to administration of the antibody, a decreased score on the Asthma Control Questionnaire 7 scale relative to a score on the Asthma Control Questionnaire 7 scale prior to administration of the antibody and a decreased score on the Childhood Asthma Control Test relative to a score on the Childhood Asthma Control Test prior to administration of the antibody.

Another embodiment is a composition of the disclosure wherein the antibody is administered by a safety syringe or an autoinjector.

Another embodiment is a composition of the disclosure wherein the therapeutically effective amount of the antibody is about 100 mg.

EXAMPLES

Example 1

Pharmacokinetics and Pharmacodynamics of Mepolizumab Administered Subcutaneously in Children Mepolizumab is a humanized immunoglobulin G (IgG1) monoclonal antibody (mAb) that exhibits dose proportional and time-independent pharmacokinetics. The pharmacokinetic (PK) and pharmacodynamic (PD) of mepolizumab in children aged 6 to 11 years with severe eosinophilic asthma was studied as described here. In Part A of the study the PK/PD of mepolizumab 40 milligrams (mg) or 100 mg administered subcutaneously depending on participant body weight is described. Part B of the study will be a long-term safety/pharmacodynamic phase in which extended treatment for a further 52 weeks will be offered on an optional basis to those subjects eligible for continued treatment.

In the study pediatric subjects with with bodyweight <40 kilogram (kg) were dosed with mepolizumab 40 mg and participants with body weight >=40 kg were dosed with mepolizumab 100 mg subcutaneously in upper arm or thigh at Visit 2 (Week 0). Approximately 40 male or female participants aged 6 to 11 years as described below were screened to achieve approximately 28 eligible participants entering the treatment phase to allow availability of 20 evaluable participants, with a minimum of six participants enrolled in the <40 kg bodyweight group. The total duration of the study was 22 weeks and included a run-in period of 1-2 weeks, a treatment period of 12 weeks and a follow-up phase of 8 weeks. A participant was considered to have completed the study if the participant completed all phases of the study including the follow-up phase (Week 20 [visit 8]).

In the first arm of the study participants were administered 40 mg of mepolizumab (this arm included patients who completed Part A the PK/PD study and who will complete Part B). In this arm of the study participants with bodyweight <40 kg received 0.4 milliliter (mL) of reconstituted mepolizumab administered subcutaneously, in the upper arm or thigh. Mepolizumab for this arm was supplied as 100 mg lyophilized cake in sterile vials for subcutaneous administration in upper arm or thigh. The vial was reconstituted with sterile water for injection prior to individual use.

In the second arm of the study participants were administered 100 mg of mepolizumab (this arm included patients who completed Part A the PK/PD study and who will complete Part B). In this arm of the study participants with bodyweight >=40 kg received 1.0 mL of reconstituted mepolizumab subcutaneously, in the upper arm or thigh. Mepolizumab for this second arm was supplied and reconstituted as described above for the first arm of the study.

Pediatric patients in the study met the following inclusion criteria:

Between 6 and 11 years of age inclusive, at the time of screening.

Diagnosis of severe asthma, defined by the regional asthma guidelines (i.e., National Institute of Health (NIH), Global Initiative for Asthma (GINA), etc.), for at least 12 months prior to Visit 1. If the participant was naïve to the study site, the participant/guardian must self-report a physician diagnosis of asthma and the investigator must confirm by review of medical history with the participant/guardian.

Eosinophilic airway inflammation that is related to asthma characterized as eosinophilic in nature as indicated by: elevated peripheral blood eosinophil count of >=300 cells per microliter (cells/μL) demonstrated in the past 12 months OR elevated peripheral blood eosinophil count of >=150/μL at visit 1.

A well-documented requirement for regular treatment with inhaled corticosteroid (>200 Kg/day fluticasone propionate drug powder inhaler [DPI] or equivalent daily) in the 12 months prior to Visit 1 with or without maintenance oral corticosteroids (OCS). The ICS dose should represent medium or high dose in children aged 6-11 years of age [GINA].

Current treatment with an additional controller medication for at least 3 months or a documented failure in the past 12 months of an additional controller medication for at least 3 successive months. [e.g., long-acting beta-2-agonist (LABA), leukotriene receptor antagonist (LTRA), or theophylline.]

Forced expiratory volume in one second (FEV1): Persistent airflow obstruction at either Visit 1 or Visit 2 (FEV1 performed prior to first dose of study medication) as indicated by: A pre-bronchodilator FEV1<110% predicted (Quanjer, 2012) OR FEV1: Forced vital capacity (FVC) ratio <0.8.

Previously confirmed history of two or more exacerbations requiring treatment with systemic corticosteroids (CS) (intramuscular [IM], intravenous, or oral), in the 12 months prior to visit 1, despite the use of high-dose inhaled corticosteroids (ICS). For participants receiving maintenance CS, the CS treatment for the exacerbations must have been a two-fold increase or greater in the dose.

No changes in the dose or regimen of baseline ICS and/or additional controller medication during the run-in period.

Male or female: Females of childbearing potential must commit to consistent and correct use of an acceptable method of contraception for the duration of the trial and for 4 months after the last dose of investigational product. A urine pregnancy test is required of girls of childbearing potential. This test will be performed at the initial screening visit (visit 1) and will be performed at each scheduled study visit prior to the administration of investigational product, and during the early withdrawal and follow-up visits.

Parent(s)/guardian able to give written informed consent prior to participation in the study, which will include the ability to comply with the requirements and restrictions listed in the consent form. If applicable, the participant must be able and willing to give assent to take part in the study according to the local requirement.

For Part B: The subject has completed all study assessments up-to and including Visit 8 and received all 3 doses of investigational product (IP) in Part A For Part B: The Principal Investigator (PI) has performed a benefit/risk assessment and this assessment supports continued therapy with mepolizumab.

The subject's parents (or guardian) have given consent and the subject has given assent for continued treatment Results for patients treated according to Part A of the study are as follow (Table 16); fields for outcomes to be evaluated in Part B of the study are also as follow:

TABLE 16

Table 16.

| PARTICIPANT FLOW |
| --- |
| Recruitment Details |

Key information relevant to the recruitment process for the overall study, such as dates of the recruitment period and locations:
This was a multi-centre, open-label study to assess the pharmacokinetics (PK) and pharmacodynamics (PD) of three (4-weekly) doses of mepolizumab 40 or 100 milligrams (mg) subcutaneously (SC), administered to participants with severe eosinophilic asthma aged 6-11 years. The results presented are based on the interim analysis, following Part A.
Pre-Assignment Details Significant events and approaches for the overall study following participant enrollment, but prior to group assignment:
This study consisted of two phases: Part A consist of pre-screening/screening/run-in, treatment, and Follow-up. Part B consisted of long-term treatment and Follow-up. A total of 44 participants were screened and 36 were enrolled to treatment in Part A. Study was conducted at 13 sites in 4 countries (Japan, Poland, United Kingdom and United States

| Types of units assigned Reporting Groups | |
| --- | --- |
| | Description |
| Mepolizumab 40 mg SC | Participants with bodyweight <40 kilogram (kg) received 0.4 milliliter (ml) of reconstituted mepolizumab subcutaneously every four weeks, in upper arm or thigh directly from the investigator or designee, under medical supervision. Participant's weight at Week 0 (Visit 2) was considered to select dosage in Part A. Prior to administration, each vial of mepolizumab were reconstituted and swirled gently to enable complete dissolution of the product. |
| Mepolizumab 100 mg SC | Participants with bodyweight >=40 kg received 1.0 ml of reconstituted mepolizumab subcutaneously every four weeks, in upper arm or thigh directly from the investigator or designee, under medical supervision. Prior to administration, each vial of mepolizumab were reconstituted and swirled gently to enable complete dissolution of the product. On investigator discretion, injected volume was split between two injection sites and was given as 2 injections of 0.5 ml each if required. |

| Overall Study | | |
| --- | --- | --- |
| MILESTONE/REASON | Mepolizumab 40 mg SC Number of participants | Mepolizumab 100 mg SC Number of participants |
| STARTED | 26 | 10 |
| COMPLETED | 22 | 10 |
| Not Completed | 4 | 0 |
| Physician Decision | 1 | 0 |

TABLE 16-continued

Table 16.

| | | |
|---|---|---|
| Other: Adverse Event of Asthma Exacerbat | 1 | 0 |
| Withdrawal by Subject | 2 | 0 |

BASELINE CHARACTERISTICS
Population Description

This data element can be used to explain how the number of participants for analysis was determined if the Overall Number of Participants is different from the Milestones (e.g., STARTED) in the Participant Flow module.

Reporting Groups

| | Description |
|---|---|
| Mepolizumab 40 mg SC | Participants with body weight <40 kilogram (kg) received 0.4 milliliter (ml) of reconstituted mepolizumab subcutaneously every four weeks, in upper arm or thigh directly from the investigator or designee, under medical supervision. Participant's weight at Week 0 (Visit 2) was considered to select dosage in Part A. Prior to administration, each vial of mepolizumab were reconstituted and swirled gently to enable complete dissolution of the product. |
| Mepolizumab 100 mg SC | Participants with body weight >=40 kg received 1.0 ml of reconstituted mepolizumab subcutaneously every four weeks, in upper arm or thigh directly from the investigator or designee, under medical supervision. Prior to administration, each vial of mepolizumab were reconstituted and swirled gently to enable complete dissolution of the product. On investigator discretion, injected volume was split between two injection sites and was given as 2 injections of 0.5 ml each if required. |

Baseline Measures

| | Mepolizumab 40 mg SC | Mepolizumab 100 mg SC | Total |
|---|---|---|---|
| Number of Participants | 26 | 10 | 36 |
| Age Continuous | | | |
| Units: Years | | | |
| Mean ± Standard Deviation | | | |
| Analysis Population Type: Participants | | | |
| | 8.0 ± 1.79 | 10.0 ± 1.33 | 8.6 ± 1.89 |
| Number of Participants Analyzed | 26 | 10 | 36 |
| Sex: Female, Male | | | |
| Units: Participants | | | |
| Count of Participants | | | |
| Analysis Population Type: Participants | | | |
| Female | 6 (23%) | 5 (50%) | 11 (31%) |
| Male | 20 (77%) | 5 (50%) | 25 (69%) |
| Number of Participants Analyzed | 26 | 10 | 36 |
| Race/Ethnicity, Customized | | | |
| Units: Participants | | | |
| Count of Participants | | | |
| Analysis Population Type: Participants | | | |
| Central/South Asian Heritage (Her.) | | | |
| | 1 (4%) | 0 (0%) | 1 (3%) |
| Number of Participants Analyzed | 26 | 10 | 36 |
| Japanese Her. | | | |
| | 6 (23%) | 1 (10%) | 7 (19%) |
| Number of Participants Analyzed | 26 | 10 | 36 |
| Black or African American (B or Af Am) | | | |
| | 4 (15%) | 3 (30%) | 7 (19%) |
| Number of Participants Analyzed | 26 | 10 | 36 |

TABLE 16-continued

Table 16.

| White/Caucasian/European Her. | | | | |
|---|---|---|---|---|
| | | 14 (54%) | 6 (60%) | 20 (56%) |
| Number of Participants Analyzed | | 26 | 10 | 36 |
| B or Af Am and White-White/Caucasian/European Her. | | | | |
| | | 1 (4%) | 0 (0%) | 1 (3%) |
| Number of Participants Analyzed | | 26 | 10 | 36 |
| OUTCOME MEASURES 1 Primary Outcome | | | | |
| Measure Name | Maximum plasma concentration (Cmax) of mepolizumab for Part A | | | |
| Measure Description | PK of mepolizumab was evaluated in participants using Cmax. PK samples were collected at pre-dose on Week 4 and 8; and at Week 9, 12, 16 and 20. Cmax was evaluated by population PK methods and mean and standard error from the final model has been tabulated. Estimates have been presented from the final centred to mean body weights of 27 kg, 50 kg and 70 kg. Note the average body weight of 70 kg (mean body weight observed in adults) was not investigated in the study. PK Population included all participants receiving at least one dose of mepolizumab beginning at Visit 2 (Week 0) and having at least one blood sample taken at Visit 3 (Week 4) or thereafter with measurable mepolizumab plasma concentration. | | | |
| Time Frame | Week 4, 8, 9, 12, 16 and 20 | | | |
| Type of Units Analyzed | | | | |
| Measure Type | Mean | | | |
| Unit of Measure | Microgram (ug)/ml | | | |
| Measure of Dispersion | Standard error | | | |

Population Description

Explanation of how the number of participants for analysis was determined. Includes whether analysis was per protocol, intention to treat, or another method. Also provides relevant details such as imputation technique, as appropriate:
PK Population Reporting Groups

| | Description |
|---|---|
| Mepolizumab SC | Participants received mepolizumab 40 or 100 mg SC, depending on participant's body weight (40 mg for <40 kg and 100 mg for >=40 kg). Participants received 0.4 ml of reconstituted mepolizumab subcutaneously (for 40 mg dose) or 1.0 ml of reconstituted mepolizumab subcutaneously (for 100 mg dose) every four weeks, in upper arm or thigh directly from the investigator or designee, under medical supervision. Prior to administration, each vial of mepolizumab were reconstituted and swirled gently to enable complete dissolution of the product. |

Measured values

| | Mepolizumab SC |
|---|---|
| Maximum plasma concentration (Cmax) of mepolizumab for Part A | |
| Number of Participants Analyzed Units: Microgram (ug)/mL Mean (Standard error) 70 kg | 36 |
| | 12.8188 ± 0.7843 |
| Number of Participants Analyzed 50 kg | 36 |
| | 16.3412 ± 0.6364 |
| Number of Participants Analyzed 27 kg | 36 |
| | 10.1960 ± 0.3345 |
| Number of Participants Analyzed | 36 |

TABLE 16-continued

Table 16.

2 Primary Outcome

| | |
|---|---|
| Measure Name | Area under concentration time curve to infinity (AUC [0-inf]) of mepolizumab for Part A |
| Measure Description | PK of mepolizumab was evaluated in participants using AUC (0-inf). PK samples were collected pre-dose on Week 4 and 8; and at Week 9, 12, 16 and 20. AUC (0-inf) was evaluated by population PK methods and mean and standard error from the final model has been tabulated. Estimates have been presented from the final centred to mean bodyweights of 27 kg, 50 kg and 70 kg. Note the average body weight of 70 kg (meanbody weight observed in adults) was not investigated in the study. |
| Time Frame | Week 4, 8, 9, 12, 16 and 20 |
| Type of Units Analyzed | |
| Measure Type | Mean |
| Unit of Measure | Day*ug/ml |
| Measure of Dispersion | Standard error |

Population Description

Explanation of how the number of participants for analysis was determined. Includes whether analysis was per protocol, intention to treat, or another method. Also provides relevant details such as imputation technique, as appropriate:
PK Population

Reporting Groups

| | Description |
|---|---|
| Mepolizumab SC | Participants received mepolizumab 40 or 100 mg SC, depending on participant's bodyweight (40 mg for <40 kg and 100 mg for >=40 kg). Participants received 0.4 ml of reconstituted mepolizumab subcutaneously (for 40 mg dose) or 1.0 ml of reconstituted mepolizumab subcutaneously (for 100 mg dose) every four weeks, in upper arm or thigh directly from the investigator or designee, under medical supervision. Prior to administration, each vial of mepolizumab were reconstituted and swirled gently to enable complete dissolution of the product. |

Measured Values

| | Mepolizumab SC |
|---|---|
| Area under concentration time curve io infinity (AUC [0-inf]) of mepolizumab for Part A | |
| Number of Participants Analyzed | 36 |
| Units: Day*ug/mL | |
| Mean (Standard error) | |
| 70 kg | |
| | 508.23 ± 41.8036 |
| Number of Participants Analyzed | 36 |
| 50 kg | |
| | 675.20 ± 35.8980 |
| Number of Participants Analyzed | 36 |
| 27 kg | |
| | 454.39 ± 15.8876 |
| Number of Participants Analyzed | 36 |

3 Primary Outcome

| | |
|---|---|
| Measure Name | Terminalphase elimination half-life (t½) of mepolizumab during treatment period for Part A |
| Measure Description | PK of mepolizumab was evaluated in participants using t½. PK samples were collected at pre-dose on Week 4 and 8; and at Week 9, 12, 16 and 20. T½ was evaluated by population PK methods and mean and standard error from the final model has been tabulated. Estimates have been presented from the final centred to mean bodyweights of 27 kg, 50 kg and 70 kg. Note the average bodyweight of 70 kg (mean body weight observed in adults) was not investigated in the study. |

TABLE 16-continued

Table 16.

| | |
|---|---|
| Time Frame | Week 4, 8, 9, 12, 16 and 20 |
| Type of Units Analyzed | |
| Measure Type | Mean |
| Unit of Measure | Days |
| Measure of Dispersion | Standard error |

Population Description

Explanation of how the number of participants for analysis was determined. Includes whether analysis was per protocol, intention to treat, or another method. Also provides relevant details such as imputation technique, as appropriate:
PK Population Reporting Groups

| | Description |
|---|---|
| Mepolizumab SC | Participants received mepolizumab 40 or 100 mg SC, depending on participant's body weight (40 mg for <40 kg and 100 mg for >=40 kg). Participants received 0.4 ml of reconstituted mepolizumab subcutaneously (for 40 mg dose) or 1.0 ml of reconstituted mepolizumab subcutaneously (for 100 mg dose) every four weeks, in upper arm or thigh directly from the investigator or designee, raider medical supervision. Prior to administration, each vial of mepolizumab were reconstituted and swirled gently to enable complete dissolution of the product. |

Measured Values

| | Mepolizumab SC |
|---|---|
| Terminal phase elimination half-life ($t^{1\!/\!2}$) of mepolizumab during treatment period for Part A | |
| Number of Participants Analyzed | 36 |
| Units: Days | |
| Mean (Standard error) | |
| 70 kg | 20.9583 ± 1.6520 |
| Number of Participants Analyzed | 36 |
| 50 kg | 21.8420 ± 1.0999 |
| Number of Participants Analyzed | 36 |
| 27 kg | 23.5582 ± 0.8406 |
| Number of Participants Analyzed | 36 |

4 Primary Outcome

| | |
|---|---|
| Measure Name | Plasma. Apparent Clearance (Cl/F) of mepolizumab in Part A |
| Measure Description | PK of mepolizumab was evaluated in participants using Cl/F. PK samples were collected at pre-dose on Week 4 and 8; and at Week 9, 12, 16 and 20. Cl was evaluated by population PK methods and mean and standard error from the final model has been tabulated. Estimates have been presented from the final centred to mean body weights of 27 kg, 50 kg and 70 kg. Note the average body weight of 70 kg (mean body weight observed in adults) was not investigated in the study. |
| Time Frame | Week 4, 8, 9, 12, 16 and 20 |
| Type of Units Analyzed | |
| Measure Type | Mean |
| Unit of Measure | liter (l)/day |
| Measure of Dispersion | Standard Error |

TABLE 16-continued

Table 16.

| Population Description |
| --- |

Explanation of how the number of participants for analysis was determined. Includes whether analysis was per protocol, intention to treat, or another method. Also provides relevant details such as imputation technique, as appropriate:
PK Population

| Reporting Groups | |
| --- | --- |
| | Description |
| Mepolizumab SC | Participants received mepolizumab 40 or 100 mg SC, depending on participant's body weight (40 mg for <40 kg and 100 mg for >=40 kg). Participants received 0.4 ml of reconstituted mepolizumab subcutaneously (for 40 mg dose) or 1.0 ml of reconstituted mepolizumab subcutaneously (for 100 mg dose) every four weeks, in upper arm or thigh directly from the investigator or designee, under medical supervision. Prior to administration, each vial of mepolizumab were reconstituted and swirled gently to enable complete dissolution of the product. |

| Measured Values | |
| --- | --- |
| | Mepolizumab SC |
| Plasma Apparent Clearance (CL/F) of mepolizumab in Part A | |
| Number of Participants Analyzed Units: Liter (L)/day Mean (Standard error) | 36 |
| 70 kg | 0.1968 ± 0.01618 |
| Number of Participants Analyzed | 36 |
| 50 kg | 0.1481 ± 0.007874 |
| Number of Participants Analyzed | 36 |
| 27 kg | 0.08803 ± 0.003078 |
| Number of Participants Analyzed | 36 |

| 5 Primary Outcome | |
| --- | --- |
| Measure Name | Ratio to Baseline in absolute blood eosinophil count at Week 12 for Part A |
| Measure Description | PD of mepolizumab was evaluated in participants using ratio to Baseline in absolute blood eosinophil count. Blood samples were collected at Screening and at Week 0, 4, 8, 9, 12, 16 and 20. Baseline was defined as the latest value recorded prior to the first dose of mepolizumab. Ratio to Baseline was calculated as post-dose visit value/Baseline value. It was evaluated by Pharmacodynamic Eosinophils (PDe) Population which included all participants receiving at least one dose of mepolizumab beginning at Visit 2 (Week 0) and having at least one Part A blood sample evaluable for blood eosinophil count. |
| Time Frame | Baseline and Week 12 |
| Type of Units Analyzed | |
| Measure Type | Geometric Mean |
| Unit of Measure | $10^9$/L |
| Measure of Dispersion | 95% Confidence Interval |

| Population Description |
| --- |

Explanation of how the number of participants for analysis was determined. Includes whether analysis was per protocol, intention to treat, or another method. Also provides relevant details such as imputation technique, as appropriate:
PDe Population

TABLE 16-continued

Table 16.

Reporting Groups

| | Description |
|---|---|
| Mepolizumab 40 mg SC | Participants with body weight <40 kilogram (kg) received 0.4 milliliter (ml) of reconstituted mepolizumab subcutaneously every four weeks, in upper arm or thigh directly from the investigator or designee, under medical supervision. Participant's weight at Week 0 (Visit 2) was considered to select dosage in Part A. Prior to administration, each vial of mepolizumab were reconstituted and swirled gently to enable complete dissolution of the product. |
| Mepolizumab 100 mg SC | Participants with body weight >=40 kg received 1.0 ml of reconstituted mepolizumab subcutaneously every four weeks, in upper arm or thigh directly from the investigator or designee, under medical supervision. Prior to administration, each vial of mepolizumab were reconstituted and swirled gently to enable complete dissolution of the product. On investigator discretion, injected volume was split between two injection sites and was given as 2 injections of 0.5 ml each if required. |

Measured values

| | Mepolizumab 40 mg SC | Mepolizumab 100 mg SC |
|---|---|---|
| Ratio to Baseline in absolute blood eosinophil count at Week 12 for Part A | | |
| Number of Participants Analyzed | 26 | 10 |
| | 0.115 (0.067 to 0.196) | 0.166 (0.087 to 0.318) |
| Number of Participants Analyzed | 26 | 10 |

6 Primary Outcome

| | |
|---|---|
| Measure Name | Number of participants with any adverse event (AE) and any serious adverse events (SAE) in Part B |
| Measure Description | An AE is any untoward medical occurrence in a participant or clinical investigation participant, temporally associated with the use of a medicinal product, whether or not considered related to the medicinal product. Any untoward event resulting in death, life threatening, requires hospitalization or prolongation of existing hospitalization, results in disability/incapacity, congenital anomaly/birth defect, any other situation according to medical or scientific judgment or all events of possible drug-induced liver injury with hyperbilirubinaemia are to be categorized as SAE. Safety Population includes all participants who received at least one dose of mepolizumab beginning at Visit 9. Participants who enter into Part B of the study and receive any of the study treatment and have any on-treatment AE or SAE (defined as events occurring from the first dose until 28 days after the last dose of mepolizumab) is planned to be considered for analysis. |
| Time Frame | From Week 20 up to Week 80 |
| Type of Units Analyzed | |
| Measure Type | Number |
| Unit of Measure | Participants |
| Measure of Dispersion | Not Applicable |

7 Primary Outcome

| | |
|---|---|
| Measure Name | Number of participants with positive anti-mepolizumab binding antibodies and neutralizing antibodies response in Part B |
| Measure Description | Blood samples for immunogenicity are to be collected for anti-mepolizumab binding antibodies and neutralizing antibodies response in Part B at Week 44, 68 and 80. Number of participants with positive anti-mepolizumab binding antibodies and neutralizing antibodies response is planned to be summarized. |
| Time Frame | From Week 20 up to Week 80 |
| Type of Units Analyzed | |
| Measure Type | Number |
| Unit of Measure | Participants |
| Measure of Dispersion | Not Applicable |

TABLE 16-continued

Table 16.

| | |
|---|---|
| 8 Primary Outcome | |
| Measure Name | Number of participants with clinically significant changes in vital sign measurements in Part B |
| Measure Description | Sitting pulse rate and blood pressure measurements are to be performed in Part B at Week 24, 28, 32, 36, 40, 44, 48, 52, 56, 60, 64, 68, 72 and 80. Mean change from baseline and standard deviation in vital sign measurements are planned to be summarized. |
| Time Frame | From Week 20 up to Week 80 |
| Type of Units Analyzed | |
| Measure Type | Mean |
| Unit of Measure | Participants |
| Measure of Dispersion | Standard Deviation |
| 9 Primary Outcome | |
| Measure Name | Number of participants with clinically significant changes in clinical laboratory parameters in Part B |
| Measure Description | Blood samples are to be collected at Week 32, 44, 56, 68, 72 and 80 in Part B to perform hematology and clinical chemistry. Number of participants with clinically significant changes in clinical laboratory parameters are planned to be summarized. |
| Time Frame | From Week 20 up to Week 80 |
| Type of Units Analyzed | |
| Measure Type | Number |
| Unit of Measure | Participants |
| Measure of Dispersion | Not Applicable |
| 10 Secondary Outcome | |
| Measure Name | Body weight-adjusted apparent clearance of Mepolizumab for Part A |
| Measure Description | PK samples were collected at pre-dose on Week 4 and 8; and at Week 9, 12, 16 and 20. The body weight-adjusted apparent clearance was compared between adults and participants aged 6 to 11 years old with severe eosinophilic asthma when mepolizumab was administered subcutaneously. Point estimate and 90% CI for participants aged 6 to 11 years (centred to a mean body weight of 70 kg) was compared with the historic adult estimated body-weight adjusted clearance of 0.22 liter (l)/day, around which a proposed 80-125% interval was applied i.e. 0.18-0.28 l/day. Assuming an absolute bioavailability of 75% this corresponds to an apparent clearance of 0.29 l/day with the proposed 80% to 125% interval of 0.23 to 0.36 l/day. Note the average body weight of 70 kg (mean body weight observed in adults) was not observed in the study. |
| Time Frame | Week 4, 8, 9, 12, 16 and 20 |
| Type of Units Analyzed | |
| Measure Type | Mean |
| Unit of Measure | l/day |
| Measure of Dispersion | 90% Confidence Interval |

Population Description

Explanation of how the number of participants for analysis was determined. Includes whether analysis was per protocol, intention to treat, or another method. Also provides relevant details such as imputation technique, as appropriate:
PK Population Reporting Groups

| | Description |
|---|---|
| Mepolizumab SC | Participants received mepolizumab 40 or 100 mg SC, depending on participant's body weight (40 mg for <40 kg and 100 mg for >=40 kg). Participants received 0.4 ml of reconstituted mepolizumab subcutaneously (for 40 mg dose) or 1.0 ml of reconstituted mepolizumab subcutaneously (for 100 mg dose) |

TABLE 16-continued

Table 16.

every four weeks, in upper arm or thigh directly from the investigator or designee, under medical supervision. Prior to administration, each vial of mepolizumab were reconstituted and swirled gently to enable complete dissolution of the product.

Measured Values

| | Mepolizumab SC |
|---|---|
| Body weight-adjusted apparent clearance of Mepolizumab for Part A | |
| Number of Participants Analyzed | 36 |
| Units: L/day | |
| Mean (90% Confidence Interval) | |
| Weight 70 kg | |
| | 0.1968 (0.1694 to 0.2241) |
| Number of Participants Analyzed | 36 |
| Weights 50 kg | |
| | 0.1481 (0.1348 to 0.1614) |
| Number of Participants Analyzed | 36 |
| Weight 27 kg | |
| | 0.0880 (0.0828 to 0.0932) |
| Number of Participants Analyzed | 36 |

11 Secondary Outcome

| | |
|---|---|
| Measure Name | Change from Baseline in Asthma Control Questionnaire-7 (ACQ-7) at Week 12 in Part A |
| Measure Description | ACQ-7 is a simple questionnaire to measure the adequacy of asthma control and change in asthma control which occurs either spontaneously or a result of treatment. The ACQ-7 uses a 7-point scale (0 = no impairment, 6 = maximum impairment for symptoms and rescue use; and 7 categories for forced expiratory volume in 1 second [FEV1]%). The instrument has a reported high test-retest reproducibility with an intraclass correlation coefficient = 0.90. The minimally important change in score is 0.5. Baseline was defined as the latest value recorded prior to the first dose of mepolizumab. Change from Baseline was calculated as score obtained at Week 12 minus Baseline Score. Pharmacodynamic Outcome (PDo) Population included all participants who received at least one dose of mepolizumab beginning at Visit 2 and having at least one Part A assessment of pharmacodynamic outcomes. |
| Time Frame | Baseline and Week 12 |
| Type of Units Analyzed | |
| Measure Type | Mean |
| Unit of Measure | Score on a scale |
| Measure of Dispersion | Standard Deviation |

Population Description

Explanation of how the number of participants for analysis was determined. Includes whether analysis was per protocol, intention to treat, or another method. Also provides relevant details such as imputation technique, as appropriate:
PDo Population

Reporting Groups

| | Description |
|---|---|
| Mepolizumab 40 mg SC | Participants with bodyweight <40 kilogram (kg) received 0.4 milliliter (ml) of reconstituted mepolizumab subcutaneously every four weeks, in upper arm or thigh directly from the investigator or designee, under medical supervision. Participant's weight at Week 0 (Visit 2) was considered to select dosage in Part A. Prior to administration, each vial of mepolizumab were reconstituted and swirled gently to enable complete dissolution of the product. |
| Mepolizumab 100 mg SC | Participants with body weight >=40 kg received 1.0 ml of reconstituted mepolizumab subcutaneously every four weeks, in upper arm or thigh directly from the investigator or designee, under medical supervision. Prior to administration, each vial of mepolizumab were reconstituted and swirled gently to enable |

TABLE 16-continued

Table 16.

complete dissolution of the product. On investigator discretion, injected volume was split between two injection sites and was given as 2 injections of 0.5 ml each if required.

Measured Values

|  | Mepolizumab 40 mg SC | Mepolizumab 100 mg SC |
|---|---|---|
| Change from Baseline in Asthma Control Questionnaire-7 (ACQ-7) at Week 12 in Part A | | |
| Number of Participants Analyzed | 23 | 10 |
|  | −0.414 ± 1.1354 | 0.082 ± 1.3432 |
| Number of Participants Analyzed | 23 | 10 |

12 Secondary Outcome

| | |
|---|---|
| Measure Name | Change from Baseline in Asthma Control Questionnaire-7 (ACQ-7) at Week 4, 8, 16 and 20 in Part A |
| Measure Description | ACQ-7 is a simple questionnaire to measure the adequacy of asthma control and change in asthma control which occurs either spontaneously or a result of treatment. The ACQ-7 uses a 7-point scale (0 = no impairment, 6 = maximum impairment for symptoms and rescue use; and 7 categories for FEV1%). The instrument has a reported high test-retest reproducibility with an intraclass correlation coefficient = 0.90. The minimally important change in score is 0.5. Baseline was defined as the latest value recorded prior to the first dose of mepolizumab. Change from Baseline was calculated as score obtained at the indicated time point minus Baseline Score. Only those participants with data available at the specified time points were analyzed (represented by n = X in the category titles). |
| Time Frame | Baseline and up to Week 20 |
| Type of Units Analyzed | |
| Measure Type | Mean |
| Unit of Measure | Score on a scale |
| Measure of Dispersion | Standard Deviation |

Population Description

Explanation of how the number of participants for analysis was determined. Includes whether analysis was per protocol, intention to treat, or another method. Also provides relevant details such as impmation technique, as appropriate:
PDo Population

Reporting Groups

| | Description |
|---|---|
| Mepolizumab 40 mg SC | Participants with body weight <40 kilogram (kg) received 0.4 milliliter (ml) of reconstituted mepolizumab subcutaneously every four weeks, in upper arm or thigh directly from the investigator or designee, under medical supervision. Participant's weight at Week 0 (Visit 2) was considered to select dosage in Part A. Prior to administration, each vial of mepolizumab were reconstituted and swirled gently to enable complete dissolution of the product. |
| Mepolizumab 100 mg SC | Participants with body weight >=40 kg received 1.0 ml of reconstituted mepolizumab subcutaneously every four weeks, in upper arm or thigh directly from the investigator or designee, under medical supervision. Prior to administration, each vial of mepolizumab were reconstituted and swirled gently to enable |

TABLE 16-continued

Table 16.

complete dissolution of the product. On investigator discretion, injected volume was split between two injection sites and was given as 2 injections of 0.5 ml each if required.

Measured Values

| | Mepolizumab 40 mg SC | Mepolizumab 100 mg SC |
|---|---|---|
| Change from Baseline in Asthma Control Questionnaire-7 (ACQ-7) at Week 4, 8, 16 and 20 in Part A | | |
| Number of Participants Analyzed Units: Score on a scale Mean ± Standard Deviation Week 4, n = 26, 10 | 26 | 10 |
| | −0.548 ± 1.1351 | −0.473 ± 0.9607 |
| Number of Participants Analyzed Week 8, n = 26, 10 | 26 | 10 |
| | −0.652 ± 1.2270 | −0.302 ± 1.2445 |
| Number of Participants Analyzed Week 16, n = 23, 10 | 26 | 10 |
| | −0.154 ± 1.2336 | −0.087 ± 1.2541 |
| Number of Participants Analyzed Week 20, n = 24, 10 | 26 | 10 |
| | −0.261 ± 1.2303 | −0.088 ± 1.0632 |
| Number of Participants Analyzed | 26 | 10 |

13 Secondary Outcome

| | |
|---|---|
| Measure Name | Change from Baseline in Childhood Asthma Control Test (C-ACT) at Week 12 for Part A |
| Measure Description | The C-ACT assesses asthma control in children 4-11 years of age. The C-ACT is a 7-question, 2-part questionnaire, with items one through 4 were completed by the child (with assistance from a caregiver, as needed) and items 5 to 7 were completed by the caregiver. A total sum score based upon responses to all items was calculated to provide an overall measure of asthma control. Baseline was defined as the latest value recorded prior to the first dose of mepolizumab. Change from Baseline was calculated as score obtained at Week 12 minus Baseline Score. |
| Time Frame | Baseline and Week 12 |
| Type of Units Analyzed | |
| Measure Type | Mean |
| Unit of Measure | Score on a scale |
| Measure of Dispersion | Standard Deviation |

Population Description

Explanation of how the number of participants for analysis was determined. Includes whether analysis was per protocol, intention to treat, or another method. Also provides relevant details such as imputation technique, as appropriate:
PDo Population

Reporting Groups

| | Description |
|---|---|
| Mepolizumab 40 mg SC | Participants with bodyweight <40 kilogram (kg) received 0.4 milliliter (ml) of reconstituted mepolizumab subcutaneously every four weeks, in upper arm or thigh directly from the investigator or designee, under medical supervision. Participant's weight at Week 0 (Visit 2) was considered to select dosage in Part A. Prior to administration, each vial of mepolizumab were reconstituted and swirled gently to enable complete dissolution of the product. |
| Mepolizumab 100 mg SC | Participants with body weight >=40 kg received 1.0 ml of reconstituted mepolizumab subcutaneously every four weeks, in upper arm or thigh directly from the investigator or designee, under medical supervision. Prior to administration, each vial of mepolizumab were reconstituted and swirled gently to enable |

TABLE 16-continued

Table 16.

complete dissolution of the product. On investigator discretion, injected volume was split between two injection sites and was given as 2 injections of 0.5 ml each if required.

Measured Values

|  | Mepolizumab 40 mg SC | Mepolizumab 100 mg SC |
|---|---|---|
| Change from Baseline in Childhood Asthma Control Test (C-ACT) at Week 12 for Part A | | |
| Number of Participants Analyzed | 22 | 10 |
|  | 2.1 ± 4.45 | −0.3 ± 5.19 |
| Number of Participants Analyzed | 22 | 10 |

14 Secondary Outcome

| | |
|---|---|
| Measure Name | Change from Baseline in C-ACT at Week 4, 8, 16 and 20 in Part A |
| Measure Description | The C-ACT assesses asthma control in children 4-11 years of age. The C-ACT is a 7-question, 2-part questionnaire, with items one through 4 were completed by the child (with assistance from a caregiver, as needed) and items 5 to 7 were completed by the caregiver. A total sum score based upon responses to all items was calculated to provide an overall measure of asthma control. Baseline was defined as the latest value recorded prior to the first dose of mepolizumab. Change from Baseline was calculated as score obtained at the indicated time point minus Baseline Score. Only those participants with data available at the specified time points were analyzed (represented by n = X in the category titles). |
| Time Frame | Baseline and up to Week 20 |

Type of Units Analyzed

| | |
|---|---|
| Measure Type | Mean |
| Unit of Measure | Score on a scale |
| Measure of Dispersion | Standard Deviation |

Population Description

Explanation of how the number of participants for analysis was determined. Includes whether analysis was per protocol, intention to treat, or another method. Also provides relevant details such as imputation technique, as appropriate:
PDo Population

Reporting Groups

| | Description |
|---|---|
| Mepolizumab 40 mg SC | Participants with bodyweight <40 kilogram (kg) received 0.4 milliliter (ml) of reconstituted mepolizumab subcutaneously every four weeks, in upper arm or thigh directly from the investigator or designee, under medical supervision. Participant's weight at Week 0 (Visit 2) was considered to select dosage in Part A. Prior to administration, each vial of mepolizumab were reconstituted and swirled gently to enable complete dissolution of the product. |
| Mepolizumab 100 mg SC | Participants with body weight >=40 kg received 1.0 ml of reconstituted mepolizumab subcutaneously every four weeks, in upper arm or thigh directly from the investigator or designee, under medical supervision. Prior to administration, each vial of mepolizumab were reconstituted and swirled gently to enable |

TABLE 16-continued

Table 16.

complete dissolution of the product. On investigator discretion, injected volume was split between two injection sites and was given as 2 injections of 0.5 ml each if required.

Measured Values

| | Mepolizumab 40 mg SC | Mepolizumab 100 mg SC |
|---|---|---|
| Change from Baseline in C-ACT at Week 4, 8, 16 and 20 in Part A | | |
| Number of Participants Analyzed Units: Score on a scale Mean ± Standard Deviation Week 4, n = 26, 10 | 26 | 10 |
| | 1.8 ± 4.19 | 2.4 ± 4.55 |
| Number of Participants Analyzed Week 8, n = 26, 10 | 26 | 10 |
| | 3.0 ± 5.77 | 1.5 ±4.28 |
| Number of Participants Analyzed Week 16, n = 23, 10 | 26 | 10 |
| | 1.5 ± 4.62 | −0.7 ± 5.19 |
| Number of Participants Analyzed Week 20, n = 24, 10 | 26 | 10 |
| | 1.0 ± 4.23 | 0.9 ± 4.28 |
| Number of Participants Analyzed | 26 | 10 |

15 Secondary Outcome

| | |
|---|---|
| Measure Name | Number of participants with any AE and any SAE in Part A |
| Measure Description | An AE is any untoward medical occurrence in a participant or clinical investigation participant, temporally associated with the use of a medicinal product, whether or not considered related to the medicinal product. Any untoward event resulting in death, life threatening, requires hospitalization or prolongation of existing hospitalization, results in disability/incapacity, congenital anomaly/birth defect, any other situation according to medical or scientific judgment or all events of possible drug-induced liver injury with hyperbilirubinaemia were categorized as SAE. Participants who received any of the study treatment and had any on-treatment AE or SAE (defined as events occurring from the first dose until 28 days after the last dose of mepolizumab) were considered for analysis. |
| Time Frame | Up to Week 20 |
| Type of Units Analyzed | |
| Measure Type | Number |
| Unit of Measure | Participants |
| Measure of Dispersion | Not Applicable |

Population Description

Explanation of how the number of participants for analysis was determined. Includes whether analysis was per protocol, intention to treat, or another method. Also provides relevant details such as imputation technique, as appropriate:
Safety Population Reporting Groups

| | Description |
|---|---|
| Mepolizumab 40 mg SC | Participants with bodyweight <40 kilogram (kg) received 0.4 milliliter (ml) of reconstituted mepolizumab subcutaneously every four weeks, in upper arm or thigh directly from the investigator or designee, under medical supervision. Participant's weight at Week 0 (Visit 2) was considered to select dosage in Part A. Prior to administration, each vial of mepolizumab were reconstituted and swirled gently to enable complete dissolution of the product. |
| Mepolizumab 100 mg SC | Participants with body weight >=40 kg received 1.0 ml of reconstituted mepolizumab subcutaneously every four weeks, in upper arm or thigh directly from the investigator or designee, under medical supervision. Prior to administration, each vial of mepolizumab were reconstituted and swirled gently to enable complete dissolution of the product. On investigator discretion, |

TABLE 16-continued

Table 16.

injected volume was split between two injection sites and was given as 2 injections of 0.5 ml each if required.

Measured Values

|  | Mepolizumab 40 mg SC | Mepolizumab 100 mg SC |
|---|---|---|
| Number of participants with any AE and any SAE in Part A | | |
| Number of Participants Analyzed Units: Participants Number Any AE | 26 | 10 |
|  | 18 | 6 |
| Number of Participants Analyzed Any SAE | 26 | 10 |
|  | 5 | 1 |
| Number of Participants Analyzed | 26 | 10 |

16 Secondary Outcome

| | |
|---|---|
| Measure Name | Number of participants with any time change from Baseline relative to normal range in hematology parameters in Part A |
| Measure Description | Blood samples were collected at Screening and at Week 0, 4, 8, 9, 12, 16 and 20 in Part A to perform basophils, eosinophils, leukocyte (also called as white blood cells), monocyte, neutrophils, lymphocyte, platelet count, mean corpuscular hemoglobin (MCH), mean corpuscular hemoglobin concentration (MCHC), hemoglobin (Hgb), mean corpuscular volume (MCV), erythrocytes, hematocrit, reticulocytes/erythrocytes. The Baseline was the latest value recorded prior to the first dose of mepolizumab. Any time post Baseline = all visits (scheduled and unscheduled) post Baseline was considered for this visit derivation. If participant had at least one value for categories "To low" and/or "To High" along with "To Normal or No Change" then participant was counted under "To low" and/or "To High". If participant had values which belong only to "To Normal or No Change" then participant was counted under "To Normal or No Change" only. n = X: Number of participants with data analyzed at specified time points. |
| Time Frame | Up to Week 20 |
| Type of Units Analyzed | |
| Measure Type | Number |
| Unit of Measure | Participants |
| Measure of Dispersion | Not Applicable |

Population Description

Explanation of how the number of participants for analysis was determined. Includes whether analysis was per protocol, intention to treat, or another method. Also provides relevant details such as imputation technique, as appropriate:
Safety Population

Reporting Groups

| | Description |
|---|---|
| Mepolizumab 40 mg SC | Participants with body weight <40 kilogram (kg) received 0.4 milliliter (ml) of reconstituted mepolizumab subcutaneously every four weeks, in upper arm or thigh directly from the investigator or designee, under medical supervision. Participant's weight at Week 0 (Visit 2) was considered to select dosage in Part A. Prior to administration, each vial of mepolizumab were reconstituted and swirled gently to enable complete dissolution of the product. |
| Mepolizumab 100 mg SC | Participants with body weight >=40 kg received 1.0 ml of reconstituted mepolizumab subcutaneously every four weeks, in upper arm or thigh directly from the investigator or designee, under medical supervision. Prior to administration, each vial of mepolizumab were reconstituted and swirled gently to enable |

TABLE 16-continued

Table 16.

complete dissolution of the product. On investigator discretion, injected volume was split between two injection sites and was given as 2 injections of 0.5 ml each if required.

Measured Values

| | Mepolizumab 40 mg SC | Mepolizumab 100 mg SC |
|---|---|---|
| Number of participants with any time change from Baseline relative to normal range in hematology parameters in Part A | | |
| Number of Participants Analyzed Units: Participants Number Basophils, To low n = 26, 10 | 26 | 10 |
| | 0 | 0 |
| Number of Participants Analyzed Basophils, To Normal or No Change n = 26, 10 | 26 | 10 |
| | 25 | 10 |
| Number of Participants Analyzed Basophils, To high n = 26, 10 | 26 | 10 |
| | 1 | 0 |
| Number of Participants Analyzed Eosinophils, To low n = 26, 10 | 26 | 10 |
| | 15 | 6 |
| Number of Participants Analyzed Eosinophils, To Normal or No Change n = 26, 10 | 26 | 10 |
| | 10 | 4 |
| Number of Participants Analyzed Eosinophils, To high n = 26, 10 | 26 | 10 |
| | 1 | 0 |
| Number of Participants Analyzed Leukocyte, To low n = 26, 10 | 26 | 10 |
| | 8 | 2 |
| Number of Participants Analyzed Leukocyte, To Normal or No Change n = 26, 10 | 26 | 10 |
| | 17 | 8 |
| Number of Participants Analyzed Leukocyte, To high n = 26, 10 | 26 | 10 |
| | 1 | 0 |
| Number of Participants Analyzed Monocyte, To low n = 26, 10 | 26 | 10 |
| | 6 | 3 |
| Number of Participants Analyzed Monocyte, To Normal or No Change n = 26, 10 | 26 | 10 |
| | 19 | 7 |
| Number of Participants Analyzed Monocyte, To high n = 26, 10 | 26 | 10 |
| | 1 | 0 |
| Number of Participants Analyzed Neutrophils, To low n = 26, 10 | 26 | 10 |
| | 8 | 3 |
| Number of Participants Analyzed Neutrophils, To Normal or No Change n = 26, 10 | 26 | 10 |
| | 16 | 7 |
| Number of Participants Analyzed Neutrophils, To high n = 26, 10 | 26 | 10 |
| | 2 | 0 |
| Number of Participants Analyzed Lymphocyte, To low n = 26, 10 | 26 | 10 |
| | 4 | 1 |
| Number of Participants Analyzed | 26 | 10 |

TABLE 16-continued

Table 16.

| | | |
|---|---|---|
| Lymphocyte, To Normal or No Change n = 26, 10 | | |
| | 20 | 8 |
| Number of Participants Analyzed | 26 | 10 |
| Lymphocyte, To high n = 26, 10 | | |
| | 2 | 1 |
| Number of Participants Analyzed | 26 | 10 |
| Platelet count, To low n = 25, 10 | | |
| | 0 | 1 |
| Number of Participants Analyzed | 26 | 10 |
| Platelet count, To Normal or No Change n = 25, 10 | | |
| | 22 | 9 |
| Number of Participants Analyzed | 26 | 10 |
| Platelet count, To high n = 25, 10 | | |
| | 3 | 0 |
| Number of Participants Analyzed | 26 | 10 |
| MCH, To low n = 26, 10 | | |
| | 2 | 0 |
| Number of Participants Analyzed | 26 | 10 |
| MCH, To Normal or No Change n = 26, 10 | | |
| | 24 | 10 |
| Number of Participants Analyzed | 26 | 10 |
| MCH, To high n = 26, 10 | | |
| | 0 | 0 |
| Number of Participants Analyzed | 26 | 10 |
| MCHC, To low n = 26, 10 | | |
| | 1 | 1 |
| Number of Participants Analyzed | 26 | 10 |
| MCHC, To Normal or No Change n = 26, 10 | | |
| | 25 | 9 |
| Number of Participants Analyzed | 26 | 10 |
| MCHC, To high n = 26, 10 | | |
| | 0 | 0 |
| Number of Participants Analyzed | 26 | 10 |
| Hgb, To low n = 26, 10 | | |
| | 0 | 1 |
| Number of Participants Analyzed | 26 | 10 |
| Hgb, To Normal or No Change n = 26, 10 | | |
| | 26 | 9 |
| Number of Participants Analyzed | 26 | 10 |
| Hgb, To high n = 26, 10 | | |
| | 0 | 0 |
| Number of Participants Analyzed | 26 | 10 |
| MCV, To low n = 26, 10 | | |
| | 2 | 0 |
| Number of Participants Analyzed | 26 | 10 |
| MCV, To Normal or No Change n = 26, 10 | | |
| | 24 | 10 |
| Number of Participants Analyzed | 26 | 10 |
| MCV, To high n = 26, 10 | | |
| | 0 | 0 |
| Number of Participants Analyzed | 26 | 10 |
| Erythrocytes, To low n = 26, 10 | | |
| | 0 | 0 |
| Number of Participants Analyzed | 26 | 10 |
| Erythrocytes, To Normal or No Change n = 26, 10 | | |
| | 21 | 8 |
| Number of Participants Analyzed | 26 | 10 |

TABLE 16-continued

Table 16.

| | | |
|---|---|---|
| Erythrocytes, To high n = 26, 10 | 5 | 2 |
| Number of Participants Analyzed | 26 | 10 |
| Hematocrit, To low n = 26, 10 | 0 | 2 |
| Number of Participants Analyzed | 26 | 10 |
| Hematocrit, To Normal or No Change n = 26, 10 | 26 | 8 |
| Number of Participants Analyzed | 26 | 10 |
| Hematocrit, To high n = 26, 10 | 0 | 0 |
| Number of Participants Analyzed | 26 | 10 |
| Reticulocytes(Ret)/erythrocytes(Ery), To low n = 26, 10 | 8 | 1 |
| Number of Participants Analyzed | 26 | 10 |
| Ret/Ery, To Normal/No Change n = 26, 10 | 15 | 9 |
| Number of Participants Analyzed | 26 | 10 |
| Ret/Ery, To high n = 26, 10 | 3 | 0 |
| Number of Participants Analyzed | 26 | 10 |

17 Secondary Outcome

| | |
|---|---|
| Measure Name | Number of participants with any time change from Baseline relative to normal range in clinical chemistry parameters in Part A |
| Measure Description | Blood samples were collected at Screening and at Week 4, 8, 12 and 20 in Part A to perform alanine aminotransferase (AlT), alkaline phosphatase (AlP), aspartate aminotransferase (AST), gamma glutamyl transferase (GGT), albumin, protein, total billirubm, creatinine, direct billirubin, urate, calcium, carbon dioxide ($CO_2$), chloride, glucose, potassium, sodium and urea. The Baseline was defined as the latest value recorded prior to the first dose of mepolizumab. Any time post Baseline = all visits (including scheduled and unscheduled) post Baseline was considered for this visit derivation. If participant had at least one value for categories "To low" and/or "To High" along with "To Normal or No Change" then participant was counted under "To low" and/or "To High". If participant had values which belong only to "To Normal or No Change" then participant was counted raider "To Normal or No Change" only. |
| Time Frame | Up to Week 20 |
| Type of Units Analyzed | |
| Measure Type | Number |
| Unit of Measure | Participants |
| Measure of Dispersion | Not Applicable |

Population Description

Explanation of how the number of participants for analysis was determined. Includes whether analysis was per protocol, intention to treat, or another method. Also provides relevant details such as imputation technique, as appropriate:
Safety Population Reporting Groups

| | Description |
|---|---|
| Mepolizumab 40 mg SC | Participants with bodyweight <40 kilogram (kg) received 0.4 milliliter (ml) of reconstituted mepolizumab subcutaneously every four weeks, in upper arm or thigh directly from the investigator or designee, under medical supervision. Participant's weight at Week 0 (Visit 2) was considered to select dosage in Part A. Prior to administration, each vial of mepolizumab were reconstituted and swirled gently to enable complete dissolution of the product. |
| Mepolizumab 100 mg SC | Participants with body weight >=40 kg received 1.0 ml of reconstituted mepolizumab subcutaneously every four weeks, in upper arm or thigh directly from the investigator or designee, under medical supervision. Prior to administration, each vial of |

TABLE 16-continued

Table 16.

mepolizumab were reconstituted and swirled gently to enable complete dissolution of the product. On investigator discretion, injected volume was split between two injection sites and was given as 2 injections of 0.5 ml each if required.

Measured Values

|  | Mepolizumab 40 mg SC | Mepolizumab 100 mg SC |
|---|---|---|
| Number of participants with any time change from Baseline relative to normal range in clinical chemistry parameters in Part A | | |
| Number of Participants Analyzed Units: Participants Number | 26 | 10 |
| ALT, To low | 0 | 0 |
| Number of Participants Analyzed ALT, To Normal or No Change | 26 | 10 |
| | 26 | 10 |
| Number of Participants Analyzed ALT, To high | 26 | 10 |
| | 0 | 0 |
| Number of Participants Analyzed AST, To low | 26 | 10 |
| | 0 | 0 |
| Number of Participants Analyzed AST, To Normal or No Change | 26 | 10 |
| | 26 | 10 |
| Number of Participants Analyzed AST, To high | 26 | 10 |
| | 0 | 0 |
| Number of Participants Analyzed ALP, To low | 26 | 10 |
| | 0 | 0 |
| Number of Participants Analyzed ALP, To Normal or No Change | 26 | 10 |
| | 26 | 10 |
| Number of Participants Analyzed ALP, To high | 26 | 10 |
| | 0 | 0 |
| Number of Participants Analyzed GGT, To low | 26 | 10 |
| | 0 | 0 |
| Number of Participants Analyzed GGT, To Normal or No Change | 26 | 10 |
| | 26 | 10 |
| Number of Participants Analyzed GGT, To high | 26 | 10 |
| | 0 | 0 |
| Number of Participants Analyzed Albumin, To low | 26 | 10 |
| | 0 | 0 |
| Number of Participants Analyzed Albumin, To Normal or No Change | 26 | 10 |
| | 22 | 10 |
| Number of Participants Analyzed Albumin, To high | 26 | 10 |
| | 4 | 0 |
| Number of Participants Analyzed | 26 | 10 |

TABLE 16-continued

Table 16.

| | | |
|---|---|---|
| Protein, To low | | |
| | 0 | 0 |
| Number of Participants Analyzed | 26 | 10 |
| Protein, To Normal or No Change | | |
| | 23 | 10 |
| Number of Participants Analyzed | 26 | 10 |
| Protein, To high | | |
| | 3 | 0 |
| Number of Participants Analyzed | 26 | 10 |
| Total billirubin, To low | | |
| | 0 | 0 |
| Number of Participants Analyzed | 26 | 10 |
| Total billirubin, To Normal or No Change | | |
| | 26 | 10 |
| Number of Participants Analyzed | 26 | 10 |
| Total billirubin, To high | | |
| | 0 | 0 |
| Number of Participants Analyzed | 26 | 10 |
| Creatinine, To low | | |
| | 4 | 1 |
| Number of Participants Analyzed | 26 | 10 |
| Creatinine, To Normal or No Change | | |
| | 22 | 9 |
| Number of Participants Analyzed | 26 | 10 |
| Creatinine, To high | | |
| | 0 | 0 |
| Number of Participants Analyzed | 26 | 10 |
| Direct billirubin, To low | | |
| | 0 | 0 |
| Number of Participants Analyzed | 26 | 10 |
| Direct billirubin, To Normal or No Change | | |
| | 26 | 10 |
| Number of Participants Analyzed | 26 | 10 |
| Direct billirubin, To high | | |
| | 0 | 0 |
| Number of Participants Analyzed | 26 | 10 |
| Urate, To low | | |
| | 1 | 0 |
| Number of Participants Analyzed | 26 | 10 |
| Urate, To Normal or No Change | | |
| | 25 | 10 |
| Number of Participants Analyzed | 26 | 10 |
| Urate, To high | | |
| | 0 | 0 |
| Number of Participants Analyzed | 26 | 10 |
| Calcium, To low | | |
| | 0 | 0 |
| Number of Participants Analyzed | 26 | 10 |
| Calcium, To Normal or No Change | | |
| | 22 | 8 |
| Number of Participants Analyzed | 26 | 10 |
| Calcium, To high | | |
| | 4 | 2 |
| Number of Participants Analyzed | 26 | 10 |
| $CO_2$, To low | | |
| | 12 | 3 |
| Number of Participants Analyzed | 26 | 10 |

TABLE 16-continued

Table 16.

| | | |
|---|---|---|
| CO2, To Normal or No Change | | |
| | 14 | 7 |
| Number of Participants Analyzed | 26 | 10 |
| CO2, To high | | |
| | 0 | 0 |
| Number of Participants Analyzed | 26 | 10 |
| Chloride, To low | | |
| | 0 | 0 |
| Number of Participants Analyzed | 26 | 10 |
| Chloride, To Normal or No Change | | |
| | 23 | 9 |
| Number of Participants Analyzed | 26 | 10 |
| Chloride, To high | | |
| | 3 | 1 |
| Number of Participants Analyzed | 26 | 10 |
| Glucose, To low | | |
| | 2 | 0 |
| Number of Participants Analyzed | 26 | 10 |
| Glucose, To Normal or No Change | | |
| | 17 | 8 |
| Number of Participants Analyzed | 26 | 10 |
| Glucose, To high | | |
| | 7 | 2 |
| Number of Participants Analyzed | 26 | 10 |
| Potassium, To low | | |
| | 0 | 0 |
| Number of Participants Analyzed | 26 | 10 |
| Potassium, To Normal or No Change | | |
| | 26 | 10 |
| Number of Participants Analyzed | 26 | 10 |
| Potassium, To high | | |
| | 0 | 0 |
| Number of Participants Analyzed | 26 | 10 |
| Sodium, To low | | |
| | 0 | 0 |
| Number of Participants Analyzed | 26 | 10 |
| Sodium, To Normal or No Change | | |
| | 26 | 10 |
| Number of Participants Analyzed | 26 | 10 |
| Sodium, To high | | |
| | 0 | 0 |
| Number of Participants Analyzed | 26 | 10 |
| Urea, To low | | |
| | 1 | 3 |
| Number of Participants Analyzed | 26 | 10 |
| Urea, To Normal or No Change | | |
| | 25 | 7 |
| Number of Participants Analyzed | 26 | 10 |
| Urea, To high | | |
| | 0 | 0 |
| Number of Participants Analyzed | 26 | 10 |

| | |
|---|---|
| 18 Secondary Outcome | |
| Measure Name | Number of participants with positive anti-mepolizumab binding antibodies and neutralizing antibodies response in Part A |
| Measure Description | Blood sample for immunogenicity was collected for anti-mepolizumab binding antibodies and neutralizing antibodies response in Part A at Week 0, 16 and 20 prior to study treatment administration. Number of participants with |

TABLE 16-continued

Table 16.

| | |
|---|---|
| | positive anti-mepolizumab binding antibodies and neutralizing antibodies response was summarized. Participant was considered 'Positive' if they had at least one positive post-baseline assay result. Any Time Post Baseline has been presented, which included all visits (including scheduled and unscheduled) post-baseline was considered for this visit derivation. Only those participants with data available at the specified time points were analyzed (represented by n = X, X in the category titles). |
| Time Frame | Up to Week 20 |
| Type of Units Analyzed | |
| Measure Type | Number |
| Unit of Measure | Participants |
| Measure of Dispersion | Not Applicable |

Population Description

Explanation of how the number of participants for analysis was determined. Includes whether analysis was per protocol, intention to treat, or another method. Also provides relevant details such as imputation technique, as appropriate:
Safety Population Reporting Groups

| | Description |
|---|---|
| Mepolizumab 40 mg SC | Participants with body weight <40 kilogram (kg) received 0.4 milliliter (ml) of reconstituted mepolizumab subcutaneously every four weeks, in upper arm or thigh directly from the investigator or designee, under medical supervision. Participant's weight at Week 0 (Visit 2) was considered to select dosage in Part A. Prior to administration, each vial of mepolizumab were reconstituted and swirled gently to enable complete dissolution of the product. |
| Mepolizumab 100 mg SC | Participants with body weight >=40 kg received 1.0 ml of reconstituted mepolizumab subcutaneously every four weeks, in upper arm or thigh directly from the investigator or designee, under medical supervision. Prior to administration, each vial of mepolizumab were reconstituted and swirled gently to enable complete dissolution of the product. On investigator discretion, injected volume was split between two injection sites and was given as 2 injections of 0.5 ml each if required. |

Measured Values

| | Mepolizumab 40 mg SC | Mepolizumab 100 mg SC |
|---|---|---|
| Number of participants with positive anti-mepolizumab binding antibodies and neutralizing antibodies response in Part A | | |
| Number of Participants Analyzed | 26 | 10 |
| Units: Participants | | |
| Number | | |
| Anti-drug antibody, Any time post- baseline, n = 25, 10 | | |
| | 1 | 1 |
| Number of Participants Analyzed | 26 | 10 |
| Neutralizing antibody, Any time post- baseline, n = 1, 1 | | |
| | 0 | 0 |
| Number of Participants Analyzed | 26 | 10 |

19 Secondary Outcome

| | |
|---|---|
| Measure Name | Change from Baseline in sitting systolic blood pressure (SBP) and diastolic blood pressure (DBP) in Part A |
| Measure Description | Sitting blood pressure measurements were performed in Part A at Screening and at Week 0, 4, 8, 9, 12, 16 and 20. Measurements were done pre-infusion/injection with the participant sitting, having rested in this position for at least 5 minutes before each reading. The Baseline was defined as the latest value recorded prior to the first dose of mepolizumab. Change from Baseline was defined as value at indicated time point minus Baseline value. Only those participants with data available at the specified time points were analyzed (represented by n = X, X in the category titles). |

TABLE 16-continued

Table 16.

| | |
|---|---|
| Time Frame | Up to Week 20 |
| Type of Units Analyzed | |
| Measure Type | Mean |
| Unit of Measure | mmHg |
| Measure of Dispersion | Standard Deviation |

Population Description

Explanation of how the number of participants for analysis was determined. Includes whether analysis was per protocol, intention to treat, or another method. Also provides relevant details such as imputation technique, as appropriate:
Safety Population Reporting Groups

| | Description |
|---|---|
| Mepolizumab 40 mg SC | Participants with bodyweight <40 kilogram (kg) received 0.4 milliliter (ml) of reconstituted mepolizumab subcutaneously every four weeks, in upper arm or thigh directly from the investigator or designee, under medical supervision. Participant's weight at Week 0 (Visit 2) was considered to select dosage in Part A. Prior to administration, each vial of mepolizumab were reconstituted and swirled gently to enable complete dissolution of the product. |
| Mepolizumab 100 mg SC | Participants with body weight >=40 kg received 1.0 ml of reconstituted mepolizumab subcutaneously every four weeks, in upper arm or thigh directly from the investigator or designee, under medical supervision. Prior to administration, each vial of mepolizumab were reconstituted and swirled gently to enable complete dissolution of the product. On investigator discretion, injected volume was split between two injection sites and was given as 2 injections of 0.5 ml each if required. |

Measured Values

| | Mepolizumab 40 mg SC | Mepolizumab 100 mg SC |
|---|---|---|
| Change from Baseline in sitting systolic blood pressure (SBP) and diastolic blood pressure (DBP) in Part A | | |
| Number of Participants Analyzed | 26 | 10 |
| Units: mmHg | | |
| Mean ± Standard Deviation | | |
| Sitting DBP, Week 4, n = 26, 10 | 0.4 ± 5.72 | 2.1 ± 3.87 |
| Number of Participants Analyzed | 26 | 10 |
| Sitting DBP, Week 8, , n = 26, 10 | −0.4 ± 5.45 | 3.4 ± 7.59 |
| Number of Participants Analyzed | 26 | 10 |
| Sitting DBP, Week 9, , n = 22, 10 | 1.8 ± 9.82 | 4.9 ± 9.13 |
| Number of Participants Analyzed | 26 | 10 |
| Sitting DBP, Week 12, , n = 23, 10 | 1.5 ± 8.88 | 0.3 ± 9.98 |
| Number of Participants Analyzed | 26 | 10 |
| Sitting DBP, Week 16, , n = 23, 10 | 0.6 ± 6.99 | 3.9 ± 7.06 |
| Number of Participants Analyzed | 26 | 10 |
| Sitting DBP, Week 20, , n = 24, 10 | 0.7 ± 6.94 | 5.1 ± 7.03 |
| Number of Participants Analyzed | 26 | 10 |
| Sitting SBP, Week 4, n = 26, 10 | 3.6 ± 9.92 | −1.9 ± 8.81 |
| Number of Participants Analyzed | 26 | 10 |
| Sitting SBP, Week 8, , n = 26, 10 | 1.8 ± 8.65 | −0.2 ± 6.23 |
| Number of Participants Analyzed | 26 | 10 |

TABLE 16-continued

Table 16.

Sitting SBP, Week 9, , n = 22, 10

| | 2.8 ± 10.39 | −0.2 ± 12.04 |
|---|---|---|
| Number of Participants Analyzed | 26 | 10 |

Sitting SBP, Week 12, , n = 23, 10

| | 4.3 ± 9.89 | −2.9 ± 11.10 |
|---|---|---|
| Number of Participants Analyzed | 26 | 10 |

Sitting SBP, Week 16, , n = 23, 10

| | 4.3 ± 11.53 | −4.6 ± 9.94 |
|---|---|---|
| Number of Participants Analyzed | 26 | 10 |

Sitting SBP, Week 20, , n = 24, 10

| | 5.0 ± 9.21 | 1.4 ± 9.91 |
|---|---|---|
| Number of Participants Analyzed | 26 | 10 |

20 Secondary Outcome

| | |
|---|---|
| Measure Name | Change from Baseline in sitting pulse rate in Part A |
| Measure Description | Sitting pulse rate measurements was performed in Part A at Screening and at Week 0, 4, 8, 9, 12, 16 and 20. Measurements were done pre-infusion/injection with the participant sitting, having rested in this position for at least 5 minutes before each reading. The Baseline was defined as the latest value recorded prior to the first dose of mepolizumab. Change from Baseline was defined as value at indicated time point minus Baseline value. Only those participants with data available at the specified time points were analyzed (represented by n = X, X in the category titles). |
| Time Frame | Up to Week 20 |
| Type of Units Analyzed | |
| Measure Type | Mean |
| Unit of Measure | Beats per minute |
| Measure of Dispersion | Standard Deviation |

Population Description

Explanation of how the number of participants for analysis was determined. Includes whether analysis was per protocol, intention to treat, or another method. Also provides relevant details such as imputation technique, as appropriate:
Safety Population Reporting Groups

| | Description |
|---|---|
| Mepolizumab 40 mg SC | Parti cipants with body weight <40 kilogram (kg) received 0.4 milliliter (ml) of reconstituted mepolizumab subcutaneously every four weeks, in upper arm or thigh directly from the investigator or designee, under medical supervision. Participant's weight at Week 0 (Visit 2) was considered to select dosage in Part A. Prior to administration, each vial of mepolizumab were reconstituted and swirled gently to enable complete dissolution of the product. |
| Mepolizumab 100 mg SC | Participants with body weight >=40 kg received 1.0 ml of reconstituted mepolizumab subcutaneously every four weeks, in upper arm or thigh directly from the investigator or designee, under medical supervision. Prior to administration, each vial of mepolizumab were reconstituted and swirled gently to enable complete dissolution of the product. On investigator discretion, injected volume was split between two injection sites and was given as 2 injections of 0.5 ml each if required. |

Measured Values

| | Mepolizumab 40 mg SC | Mepolizumab 100 mg SC |
|---|---|---|
| Change from Baseline in sitting pulse rate in Part A | | |
| Number of Participants Analyzed | 26 | 10 |

Units: Beats per minute
Mean ± Standard Deviation
Sitting pulse rate, Week 4, n = 26, 10

| | −4.0 ± 10.91 | −1.1 ± 10.56 |
|---|---|---|
| Number of Participants Analyzed | 26 | 10 |

TABLE 16-continued

Table 16.

| Sitting pulse rate, Week 8, , n = 26, 10 | | |
|---|---|---|
| | −3.2 ± 9.11 | 1.8 ± 7.42 |
| Number of Participants Analyzed | 26 | 10 |
| Sitting pulse rate, Week 9, , n = 22, 10 | | |
| | −2.9 ± 8.31 | 2.3 ± 9.33 |
| Number of Participants Analyzed | 26 | 10 |
| Sitting pulse rate, Week 12, , n = 23, 10 | | |
| | −0.8 ± 8.31 | −0.5 ± 10.73 |
| Number of Participants Analyzed | 26 | 10 |
| Sitting pulse rate, Week 16, , n = 23, 10 | | |
| | −0.6 ± 7.65 | 3.5 ± 10.20 |
| Number of Participants Analyzed | 26 | 10 |
| Sitting pulse rate, Week 20, , n = 24, 10 | | |
| | −3.9 ± 13.13 | 1.8 ± 8.22 |
| Number of Participants Analyzed | 26 | 10 |

21 Secondary Outcome

| | |
|---|---|
| Measure Name | Change from Week 0 (Visit 2) in absolute blood eosinophil count at Weeks 32, 44, 56, 68, 72 and 80 |
| Measure Description | long term durability of PD of mepolizumab is to be evaluated in participants using change from Week 0 in absolute blood eosinophil count. Change from Week 0 (Visit 2) is to be calculated as post-dose visit value minus Week 0 value in PDe Population. |
| Time Frame | Weeks 0, 32, 44, 56, 68, 72 and 80 |
| Type of Units Analyzed | |
| Measure Type | Geometric Mean |
| Unit of Measure | 10^9/L |
| Measure of Dispersion | 95% Confidence Interval |

REPORTED ADVERSE EVENTS

| | |
|---|---|
| Time Frame | On-treatment serious adverse events (SAEs) and non-serious AEs were defined as events occurring from the first dose until 28 days after the last dose of mepolizumab. |
| Additional Description | Serious adverse events (SAEs) and Non-serious AEs were collected in members of Safety Population, comprised of all participants who received at least one dose of open label mepolizumab medication. |
| Collection Approach | Systematic Assessment |

Reporting Groups

| | Description |
|---|---|
| Mepolizumab 40 mg SC | Participants with bodyweight <40 kilogram (kg) received 0.4 milliliter (ml) of reconstituted mepolizumab subcutaneously every four weeks, in upper arm or thigh directly from the investigator or designee, under medical supervision. Participant's weight at Week 0 (Visit 2) was considered to select dosage in Part A. Prior to administration, each vial of mepolizumab were reconstituted and swirled gently to enable complete dissolution of the product. |
| Mepolizumab 100 mg SC | Participants with body weight >=40 kg received 1.0 ml of reconstituted mepolizumab subcutaneously every four weeks, in upper arm or thigh directly from the investigator or designee, under medical supervision. Prior to administration, each vial of mepolizumab were reconstituted and swirled gently to enable complete dissolution of the product. On |

TABLE 16-continued

Table 16.

investigator discretion, injected volume was split between two injection sites and was given as 2 injections of 0.5 ml each if required.

All-Cause Mortality

|  | Mepolizumab 40 mg SC | Mepolizumab 100 mg SC |
|---|---|---|
| Total | 0/26 (0%) | 0/10 (0%) |

Serious Adverse Events

|  | Mepolizumab 40 mg SC | Mepolizumab 100 mg SC |
|---|---|---|
| Total # participants affected/at risk<br>Gastrointestinal disorders<br>Nausea †[a] | 5/26 (19.23%) | 1/10 (10%) |
| # participants affected/at risk<br>General disorders<br>Chest pain †[a] | 1/26 (3.85%) | 0/10 (0%) |
| # participants affected/at risk<br>Pain †[a] | 1/26 (3.85%) | 0/10 (0%) |
| # participants affected/at risk<br>Infections and infestations<br>Cellulitis †[a] | 1/26 (3.85%) | 0/10 (0%) |
| # participants affected/at risk<br>Lower respirators tract infection †[a] | 1/26 (3.85%) | 0/10 (0%) |
| # participants affected/at risk<br>Musculoskeletal and connective tissue disorders<br>Back pain †[a] | 1/26 (3.85%) | 1/10 (10%) |
| # participants affected/at risk<br>Nervous system disorders<br>Dizziness †[a] | 1/26 (3.85%) | 0/10 (0%) |
| # participants affected/at risk<br>Headache †[a] | 1/26 (3.85%) | 0/10 (0%) |
| # participants affected/at risk<br>Respiratory thoracic and mediastinal disorders<br>Asthma †[a] | 1/26 (3.85%) | 0/10 (0%) |
| # participants affected/at risk | 3/26 (11.54%) | 0/10 (0%) |

†Indicates events were collected by systematic assessment.
* Indicates events were collected by non-systematic assessment.
[a]Source Vocabulary uses table default: MedDRA 19.1
Other Adverse Effects
Reporting Frequency Threshold 3%

|  | Mepolizumab 40 mg SC | Mepolizumab 100 mg SC |
|---|---|---|
| Total # participants affected/at risk<br>Gastrointestinal disorders<br>Abdominal pain †[a] | 18/26 (69.23%) | 6/10 (60%) |
| # participants affected/at risk<br>Abdominal pain upper †[a] | 1/26 (3.85%) | 0/10 (0%) |
| # participants affected/at risk<br>Constipation †[a] | 1/26 (3.85%) | 0/10 (0%) |
| # participants affected/at risk<br>Gastritis †[a] | 2/26 (7.69%) | 0/10 (0%) |
| # participants affected/at risk<br>Nausea †[a] | 1/26 (3.85%) | 0/10 (0%) |
| # participants affected/at risk | 3/26 (11.54%) | 0/10 (0%) |

TABLE 16-continued

Table 16.

| | | |
|---|---|---|
| Vomiting †[a] | | |
| # participants affected/at risk<br>General disorders<br>Injection site reaction †[a] | 1/26 (3.85%) | 1/10 (10%) |
| # participants affected/at risk<br>Pain †[a] | 5/26 (19.23%) | 0/10 (0%) |
| # participants affected/at risk<br>Pyrexia †[a] | 1/26 (3.85%) | 0/10 (0%) |
| # participants affected/at risk<br>Immune system disorders<br>Hypersensitivity †[a] | 1/26 (3.85%) | 0/10 (0%) |
| # participants affected/at risk<br>Infections and infestations<br>Acute sinusitis †[a] | 1/26 (3.85%) | 0/10 (0%) |
| # participants affected/at risk<br>Bronchitis †[a] | 1/26 (3.85%) | 0/10 (0%) |
| # participants affected/at risk<br>Croup infectious †[a] | 1/26 (3.85%) | 0/10 (0%) |
| # participants affected/at risk<br>Eczema infected †[a] | 1/26 (3.85%) | 0/10 (0%) |
| # participants affected/at risk<br>Gastroenteritis †[a] | 1/26 (3.85%) | 0/10 (0%) |
| # participants affected/at risk<br>Nasopharyngitis †[a] | 3/26 (11.54%) | 1/10 (10%) |
| # participants affected/at risk<br>Oral herpes †[a] | 0/26 (0%) | 1/10 (10%) |
| # participants affected/at risk<br>Otitis media acute †[a] | 1/26 (3.85%) | 0/10 (0%) |
| # participants affected/at risk<br>Pharyngitis †[a] | 1/26 (3.85%) | 0/10 (0%) |
| # participants affected/at risk<br>Pneumonia †[a] | 1/26 (3.85%) | 0/10 (0%) |
| # participants affected/at risk<br>Respiratory tract infection<br>viral †[a] | 1/26 (3.85%) | 0/10 (0%) |
| # participants affected/at risk<br>Rhinitis †[a] | 0/26 (0%) | 1/10 (10%) |
| # participants affected/at risk<br>Sinusitis †[a] | 1/26 (3.85%) | 1/10 (10%) |
| # participants affected/at risk<br>Tinea infection †[a] | 1/26 (3.85%) | 0/10 (0%) |
| # participants affected/at risk<br>Upper respiratory tract<br>infection †[a] | 2/26 (7.69%) | 1/10 (10%) |
| # participants affected/at risk<br>Viral upper respiratory tract<br>infection †[a] | 2/26 (7.69%) | 0/10 (0%) |
| # participants affected/at risk<br>Wound infection †[a] | 0/26 (0%) | 1/10 (10%) |
| # participants affected/at risk | | |

TABLE 16-continued

Table 16.

| | | |
|---|---|---|
| Injury, poisoning and procedural complications<br>Ankle fracture †[a] | | |
| # participants affected/at risk<br>Investigations<br>Alanine aminotransferase increased †[a] | 1/26 (3.85%) | 0/10 (0%) |
| # participants affected/at risk<br>Body temperature increased †[a] | 0/26 (0%) | 1/10 (10%) |
| # participants affected/at risk<br>Neutrophil count decreased †[a] | 1/26 (3.85%) | 0/10 (0%) |
| # participants affected/at risk<br>Metabolism and nutrition disorders<br>Hypercholesterolemia †[a] | 1/26 (3.85%) | 0/10 (0%) |
| # participants affected/at risk<br>Hyperglycaemia †[a] | 0/26 (0%) | 1/10 (10%) |
| # participants affected/at risk<br>Hypertriglyceridaemia †[a] | 0/26 (0%) | 1/10 (10%) |
| # participants affected/at risk<br>Musculoskeletal and connective tissue disorders<br>Musculoskeletal pain †[a] | 0/26 (0%) | 1/10 (10%) |
| # participants affected/at risk<br>Nervous system disorders<br>Dizziness †[a] | 1/26 (3.85%) | 0/10 (0%) |
| # participants affected/at risk<br>Dizziness postural †[a] | 1/26 (3.85%) | 0/10 (0%) |
| # participants affected/at risk<br>Headache †[a] | 0/26 (0%) | 1/10 (10%) |
| # participants affected/at risk<br>Lethargy †[a] | 3/26 (11.54%) | 2/10 (20%) |
| # participants affected/at risk<br>Renal and urinary disorders<br>Urinary retention †[a] | 1/26 (3.85%) | 0/10 (0%) |
| # participants affected/at risk<br>Respiratory, thoracic and mediastinal disorders<br>Asthma †[a] | 1/26 (3.85%) | 0/10 (0%) |
| # participants affected/at risk<br>Cough †[a] | 1/26 (3.85%) | 0/10 (0%) |
| # participants affected/at risk<br>Dysphonia †[a] | 1/26 (3.85%) | 0/10 (0%) |
| # participants affected/at risk<br>Epistaxis †[a] | 0/26 (0%) | 1/10 (10%) |
| # participants affected/at risk<br>Fibrinous bronchitis †[a] | 1/26 (3.85%) | 0/10 (0%) |
| # participants affected/at risk<br>Nasal congestion †[a] | 1/26 (3.85%) | 0/10 (0%) |
| # participants affected/at risk<br>Oropharyngeal pain †[a] | 0/26 (0%) | 1/10 (10%) |
| # participants affected/at risk<br>Pharyngeal erythema †[a] | 2/26 (7.69%) | 0/10 (0%) |
| # participants affected/at risk<br>Productive cough †[a] | 1/26 (3.85%) | 1/10 (10%) |
| # participants affected/at risk | 0/26 (0%) | 1/10 (10%) |

TABLE 16-continued

Table 16.

| | | |
|---|---|---|
| Upper respiratory tract inflammation †[a] | | |
| # participants affected/at risk | 1/26 (3.85%) | 0/10 (0%) |
| Wheezing †[a] | | |
| # participants affected/at risk | 2/26 (7.69%) | 1/10 (10%) |
| Skin and subcutaneous tissue disorders | | |
| Acne †[a] | | |
| # participants affected/at risk | 0/26 (0%) | 1/10 (10%) |
| Dermatitis allergic †[a] | | |
| # participants affected/at risk | 0/26 (0%) | 1/10 (10%) |
| Dry skin †[a] | | |
| # participants affected/at risk | 0/26 (0%) | 1/10 (10%) |
| Rash †[a] | | |
| # participants affected/at risk | 2/26 (7.69%) | 0/10 (0%) |

†Indicates events were collected by systematic methods.
* Indicates events were collected by non-systematic methods.
[a]Source Vocabulary uses table default: MedDRA 19.1

The "50 kg" group identified above for certain rows corresponds to pediatric patients weighing greater than or equal to 40 kg and the "27 kg" group identified above for certain rows corresponds to pediatric patients weighing less than 40 kg.

Example 2

Pharmacokinetics and Pharmacodynamic Analyses

Pharmacokinetic (PK) and pharmacodynamic (PD) analyses of study results were performed, in part, as described here. Mepolizumab plasma PK concentrations collected in the first part of the study were analysed by population-PK methods, using the NLMIXED procedure in SAS software (Version 9.2). A two-compartment PK model with first order absorption and first order elimination, parameterised in terms of macro-constants (i.e., A, B, alpha, beta), was used with distribution parameters fixed to adult values, since the number of blood draws were kept to a minimum. The ratio of blood eosinophil count to baseline was summarised using descriptive statistics. An indirect response PK/PD model, was used to estimate the blood concentration resulting in the maximum drug effect (maximum reduction in eosinophils) and 50% of the maximum drug effect. Derived exposures (area under the concentration-time curve to infinite time) normalised to the average bodyweight in each of the subcutaneous dose groups were 454 µg*day/mL (40 mg [subjects <40 kg]) and 675 µg*day/mL (100 mg [subjects >40 kg]). Estimated half-life ($t_{1/2}$) was approximately 23 days. PK data is shown in Table 17. In the methods or compositions of the disclosure Cmax SS values about those listed in Table 17 or including the indicated ranges shown in Table 17 may be recited instead of Cmax values.

TABLE 17

| | Pharmacokinetic parameter estimate (95% CIs) | |
|---|---|---|
| | Normalised to 27 kg | Normalised to 50 kg |
| AUC(0-inf) (µg*day/mL) | 454.4 (422.1, 486.7) | 675.2 (602.2, 748.1) |
| Cmax SS (µg/mL) | 17.8 (15.3, 20.2) | 28.5 (25.0, 31.9) |

TABLE 17-continued

| | Pharmacokinetic parameter estimate (95% CIs) | |
|---|---|---|
| | Normalised to 27 kg | Normalised to 50 kg |
| CL/F (L/day) | 0.088 (0.082, 0.094) | 0.15 (0.13, 0.16) |
| Cav (µ/mL) | 16.2 (15.1, 17.4) | 24.1 (21.5, 26.7) |
| Half-life (days) | 23.6 (21.9, 25.3) | 21.8 (19.6, 24.1) |
| Between-subject variability for CL/F | 0.0239 (0.0112, 0.0366) | |
| Residual | 0.0292 (0.0292, 0.0358) | |

Results presented according to the median body weight in each group AUC(0-inf), area under the concentration-time curve from time zero (pre-dose) extrapolated to infinite time; Cav, average concentration; CI, confidence interval; CL/F, apparent plasma clearance; Cmax SS, maximum plasma concentration at steady state.

Figure 3:
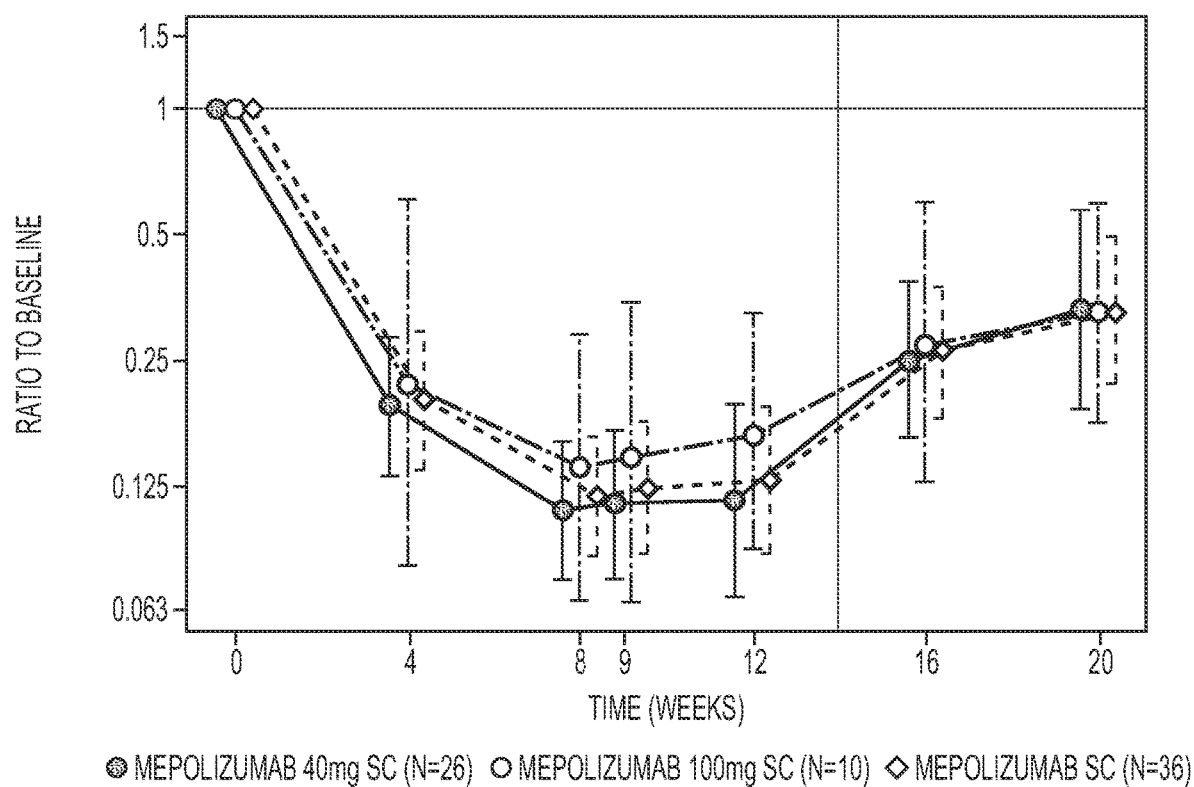
FIG. 3. Ratio of blood eosinophil count to baseline (geometric mean 95% confidence intervals).

A marked and similar blood eosinophil reduction in both treatment groups was observed in this 6 to 11 year old population, which was evident from Week 4 (first post-dose assessment) and maintained throughout the treatment phase and with a return towards baseline in the 8 week post-treatment phase (FIG. 3). At week 12, reductions from baseline in blood eosinophils were 89% (40 mg SC), 83% (100 mg SC), and 87% (overall) (FIG. 3). Absolute blood eosinophil count (geometric mean) showed a similar blood eosinophil reduction and trends. In FIG. 3, Weeks 0-12 were considered on-treatment, Weeks 16-20 were considered post-treatment and—where a result of zero was recorded—a small value (0.005) was added prior to log transformation.

Example 3

Informal Sequence Listing

Underlining below identifies CDR sequences, according to the Kabat definition of CDRs, in the variable heavy and variable light chain portions of the antibodies or the nucleic acid sequences encoding these CDR sequences. For example, in SEQ ID NO: 1 the frameworks and CDRs are presented as plaintext framework1, underlined CDR1, plaintext framework2, underlined CDR2, plaintext framework3, underlined CDR3 and plaintext framework4 in order from the amino proximal portion to the carboxy terminal portion of the sequences presented. Italics below identify signal sequences. Asterisks to the right of a character for a single letter amino acid code indicates the amino acid residue to the left is a N-glycosylation site. This scheme is used in SEQ ID NO:s 1-4, 11, 12 and 19-22, etc. for example Amino terminal methionine residues shown in these sequences can be cleaved. Thus, the sequences here showing an amino terminal methionine residue should also be considered to disclose the cleaved versions of these proteins lacking such an amino terminal methionine residue. Nucleic acids sequences are presented as DNA nucleic acid sequences and include "t" nucleic acid residues, the corresponding RNA sequence should also be considered as disclosed such that "t" nucleic acid residues may also be regarded as disclosing a "u" nucleic acid residue. Additionally, the 5' proximal "atg" start codon and the 3' proximal "taa," "tag," and "tga" stop codons have been omitted from the cDNA nucleic acid sequences below. This is the case for SEQ ID NO:s 31-34, etc. for example

```
MEPOLIZUMAB FULL LENGTH HEAVY CHAIN
                                                      SEQ ID NO: 1
QVTLRESGPALVKPTQTLTLTCTVSGFSLTSYSVHWVRQPPGKGLEWLGVIWASGGT

DYNSALMSRLSISKDTSRNQVVLTMTNMDPVDTATYYCARDPPSSLLRLDYWGRGT

PVTVSSASTKGPSVFPLAPSSKSTSGGTAALGCLVKDYFPEPVTVSWNSGALTSGVHT

FPAVLQSSGLYSLSSVVTVPSSSLGTQTYICNVNHKPSNTKVDKRVEPKSCDKTHTCP

PCPAPELLGGPSVFLFPPKPKDTLMISRTPEVTCVVVDVSHEDPEVKFNWYVDGVEV

HNAKTKPREEQYN*STYRVVSVLTVLHQDWLNGKEYKCKVSNKALPAPIEKTISKAK

GQPREPQVYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPGK

MEPOLIZUMAB FULL LENGTH LIGHT CHAIN
                                                      SEQ ID NO: 2
DIVMTQSPDSLAVSLGERATINCKSSQSLLNSGNQKNYLAWYQQKPGQPPKLLIYGA

STRESGVPDRFSGSGSGTDFTLTISSLQAEDVAVYYCQNVHSFPFTFGGGTKLEIKRTV

AAPSVFIFPPSDEQLKSGTASVVCLLNNFYPREAKVQWKVDNALQSGNSQESVTEQD

SKDSTYSLSSTLTLSKADYEKHKVYACEVTHQGLSSPVTKSFNRGEC

MEPOLIZUMAB VH
                                                      SEQ ID NO: 3
QVTLRESGPALVKPTQTLTLTCTVSGFSLTSYSVHWVRQPPGKGLEWLGVIWASGGT

DYNSALMSRLSISKDTSRNQVVLTMTNMDPVDTATYYCARDPPSSLLRLDYWGRGT

PVTVSS

MEPOLIZUMAB VL
                                                      SEQ ID NO: 4
DIVMTQSPDSLAVSLGERATINCKSSQSLLNSGNQKNYLAWYQQKPGQPPKLLIYGA

STRESGVPDRFSGSGSGTDFTLTISSLQAEDVAVYYCQNVHSFPFTFGGGTKLEIK

MEPOLIZUMAB CDRH1
                                                      SEQ ID NO: 5
SYSVH

MEPOLIZUMAB CDRH2
                                                      SEQ ID NO: 6
VIWASGGTDYNSALMS

MEPOLIZUMAB CDRH3
                                                      SEQ ID NO: 7
DPPSSLLRLDY

MEPOLIZUMAB CDRL1
                                                      SEQ ID NO: 8
KSSQSLLNSGNQKNYLA

MEPOLIZUMAB CDRL2
                                                      SEQ ID NO: 9
GASTRES

MEPOLIZUMAB CDRL3
                                                      SEQ ID NO: 10
QNVHSFPFT
```

-continued

HUMAN IL-5 (MATURE PROTEIN)
SEQ ID NO: 11
IPTEIPTSALVKETLALLSTHRTLLIANETLRIPVPVHKNHQLCTEEIFQGIGTLESQTVQ

GGTVERLFKNLSLIKKYIDGQKKKCGEERRRVNQFLDYLQEFLGVMNTEWIIES

HUMAN IL-5 RECEPTOR SUBUNIT ALPHA ISOFORM 1 (MATURE PROTEIN)
SEQ ID NO: 12
DLLPDEKISLLPPVNFTIKVTGLAQVLLQWKPNPDQEQRNVNLEYQVKINAPKEDDY

ETRITESKCVTILHKGFSASVRTILQNDHSLLASSWASAELHAPPGSPGTSIVNLTCTTN

TTEDNYSRLRSYQVSLHCTWLVGTDAPEDTQYFLYYRYGSWTEECQEYSKDTLGRN

IACWFPRTFILSKGRDWLAVLVNGSSKHSAIRPFDQLFALHAIDQINPPLNVTAEIEGT

RLSIQWEKPVSAFPIHCFDYEVKIHNTRNGYLQIEKLMTNAFISIIDDLSKYDVQVRAA

VSSMCREAGLWSEWSQPIYVGNDEHKPLREWFVIVIMATICFILLILSLICKICHLWIK

LFPPIPAPKSNIKDLFVTTNYEKAGSSETEIEVICYIEKPGVETLEDSVF

HUMAN IL-5 RECEPTOR COMMON SUBUNIT BETA (MATURE PROTEIN)
SEQ ID NO: 13
WERSLAGAEETIPLQTLRCYNDYTSHITCRWADTQDAQRLVNVTLIRRVNEDLLEPV

SCDLSDDMPWSACPHPRCVPRRCVIPCQSFVVTDVDYFSFQPDRPLGTRLTVTLTQH

VQPPEPRDLQISTDQDHFLLTWSVALGSPQSHWLSPGDLEFEVVYKRLQDSWEDAAI

LLSNTSQATLGPEHLMPSSTYVARVRTRLAPGSRLSGRPSKWSPEVCWDSQPGDEAQ

PQNLECFFDGAAVLSCSWEVRKEVASSVSFGLFYKPSPDAGEEECSPVLREGLGSLHT

RHHCQIPVPDPATHGQYIVSVQPRRAEKHIKSSVNIQMAPPSLNVTKDGDSYSLRWET

MKMRYEHIDHTFEIQYRKDTATWKDSKTETLQNAHSMALPALEPSTRYWARVRVRT

SRTGYNGIWSEWSEARSWDTESVLPMWVLALIVIFLTIAVLLALRFCGIYGYRLRRK

WEEKIPNPSKSHLFQNGSAELWPPGSMSAFTSGSPPHQGPWGSRFPELEGVFPVGFGD

SEVSPLTIEDPKHVCDPPSGPDTTPAASDLPTEQPPSPQPGPPAASHTPEKQASSFDFNG

PYLGPPHSRSLPDILGQPEPPQEGGSQKSPPPGSLEYLCLPAGGQVQLVPLAQAMGPG

QAVEVERRPSQGAAGSPSLESGGGPAPPALGPRVGGQDQKDSPVAIPMSSGDTEDPG

VASGYVSSADLVFTPNSGASSVSLVPSLGLPSDQTPSLCPGLASGPPGAPGPVKSGFEG

YVELPPIEGRSPRSPRNNPVPPEAKSPVLNPGERPADVSPTSPQPEGLLVLQQVGDYCF

LPGLGPGPLSLRSKPSSPGPGPEIKNLDQAFQVKKPPGQAVPQVPVIQLFKALKQQDY

LSLPPWEVNKPGEVC

The present invention now being fully described, it will be apparent to one of ordinary skill in the art that many changes and modifications can be made thereto without departing from the spirit or scope of the appended claims.

---

What is claimed is:

1. An aqueous liquid formulation comprising:
   (a) 40 mg of an antibody comprising the heavy chain amino acid sequence of SEQ ID NO: 1 and the light chain amino acid sequence of SEQ ID NO: 2;
   (b) a buffering agent selected from sodium phosphate dibasic heptahydrate, phosphate, citric acid, citrate, sodium phosphate, potassium phosphate, sodium citrate, histidine, or a combination thereof;
   (c) pH between 6.2 and 6.6
   (d) sucrose in an amount ranging from 5% to 20% weight by volume
   (e) polysorbate 80 in an amount ranging from 0.01% to 0.1% weight by volume; and
   (f) EDTA in an amount ranging from 0.01 mM to 0.1 mM.

2. The aqueous liquid formulation of claim 1, wherein polysorbate 80 is present in an amount of 0.05% weight by volume.

3. The aqueous liquid formulation of claim 1, wherein sucrose is present in an amount of 12% weight by volume.

4. The aqueous liquid formulation of claim 1, wherein EDTA is present in an amount of 0.05 mM.

5. The aqueous liquid formulation of claim 1, wherein the buffering agent is selected from sodium phosphate dibasic heptahydrate, citric acid monohydrate, or a combination thereof.

6. The aqueous liquid formulation of claim 5, wherein sodium phosphate dibasic heptahydrate is present in an amount ranging from 10 mM to 30 mM.

7. The aqueous liquid formulation of claim 5, wherein sodium phosphate dibasic heptahydrate is present in an amount ranging from 15 mM to 16.4 mM.

8. The aqueous liquid formulation of claim 5, wherein citric acid monohydrate is present in an amount ranging from 3.8 mM to 4.9 mM.

9. The aqueous liquid formulation of claim 5, wherein sodium phosphate dibasic heptahydrate is present in an amount of 15.5 mM, and citric acid monohydrate is present in an amount of 4.5 mM.

10. The aqueous liquid formulation of claim 1, wherein the pH is 6.3.

11. An aqueous liquid formulation comprising:
    (a) 40 mg of an antibody comprising the heavy chain amino acid sequence of SEQ ID NO: 1 and the light chain amino acid sequence of SEQ ID NO: 2;
    (b) 15 mM sodium phosphate dibasic heptahydrate and 4.5 mM citric acid monohydrate at about pH 6.3;
    (c) 12% sucrose weight by volume;
    (d) 0.02% polysorbate 80 weight by volume; and
    (e) 0.05 mM EDTA.

12. An autoinjector comprising the aqueous liquid formulation of claim 11.

13. A safety syringe comprising the aqueous liquid formulation of claim 11.

* * * * *

SEQUENCE LISTING

```
<160> NUMBER OF SEQ ID NOS: 13

<210> SEQ ID NO 1
<211> LENGTH: 449
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 1

Gln Val Thr Leu Arg Glu Ser Gly Pro Ala Leu Val Lys Pro Thr Gln
1               5                   10                  15
```

```
Thr Leu Thr Leu Thr Cys Thr Val Ser Gly Phe Ser Leu Thr Ser Tyr
                20                  25                  30

Ser Val His Trp Val Arg Gln Pro Pro Gly Lys Gly Leu Glu Trp Leu
            35                  40                  45

Gly Val Ile Trp Ala Ser Gly Gly Thr Asp Tyr Asn Ser Ala Leu Met
        50                  55                  60

Ser Arg Leu Ser Ile Ser Lys Asp Thr Ser Arg Asn Gln Val Val Leu
 65                  70                  75                  80

Thr Met Thr Asn Met Asp Pro Val Asp Thr Ala Thr Tyr Tyr Cys Ala
                85                  90                  95

Arg Asp Pro Pro Ser Ser Leu Leu Arg Leu Asp Tyr Trp Gly Arg Gly
            100                 105                 110

Thr Pro Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
```

435                 440                 445
Lys

<210> SEQ ID NO 2
<211> LENGTH: 220
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 2

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Val His Ser Phe Pro Phe Thr Phe Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 3
<211> LENGTH: 119
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 3

Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Thr Ser Tyr
            20                  25                  30

Ser Val His Trp Val Arg Gln Pro Pro Gly Lys Gly Leu Glu Trp Leu
        35                  40                  45

Gly Val Ile Trp Ala Ser Gly Gly Thr Asp Tyr Asn Ser Ala Leu Met
    50                  55                  60

Ser Arg Leu Ser Ile Ser Lys Asp Thr Ser Arg Asn Gln Val Val Leu
65                  70                  75                  80

Thr Met Thr Asn Met Asp Pro Val Asp Thr Ala Thr Tyr Tyr Cys Ala
                85                  90                  95

Arg Asp Pro Pro Ser Ser Leu Leu Arg Leu Asp Tyr Trp Gly Arg Gly
            100                 105                 110

Thr Pro Val Thr Val Ser Ser
        115

<210> SEQ ID NO 4
<211> LENGTH: 113
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 4

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Val His Ser Phe Pro Phe Thr Phe Gly Gly Gly Thr Lys Leu Glu Ile
            100                 105                 110

Lys

<210> SEQ ID NO 5
<211> LENGTH: 5
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 5

Ser Tyr Ser Val His
1               5

<210> SEQ ID NO 6
<211> LENGTH: 16
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 6

Val Ile Trp Ala Ser Gly Gly Thr Asp Tyr Asn Ser Ala Leu Met Ser
1               5                   10                  15

<210> SEQ ID NO 7
<211> LENGTH: 11
<212> TYPE: PRT

```
<213> ORGANISM: Artificial Sequence
<220> FEATURE:
<223> OTHER INFORMATION: Amino acid sequence identified using molecular
      biology techniques.

<400> SEQUENCE: 7

Asp Pro Pro Ser Ser Leu Leu Arg Leu Asp Tyr
1               5                   10

<210> SEQ ID NO 8
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 8

Lys Ser Ser Gln Ser Leu Leu Asn Ser Gly Asn Gln Lys Asn Tyr Leu
1               5                   10                  15

Ala

<210> SEQ ID NO 9
<211> LENGTH: 7
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 9

Gly Ala Ser Thr Arg Glu Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 10

Gln Asn Val His Ser Phe Pro Phe Thr
1               5

<210> SEQ ID NO 11
<211> LENGTH: 9
<212> TYPE: PRT
<213> ORGANISM: Homo Sapien

<400> SEQUENCE: 11

Gln Asn Val His Ser Phe Pro Phe Thr
1               5

<210> SEQ ID NO 12
<211> LENGTH: 400
<212> TYPE: PRT
<213> ORGANISM: Homo Sapien

<400> SEQUENCE: 12

Asp Leu Leu Pro Asp Glu Lys Ile Ser Leu Leu Pro Pro Val Asn Phe
1               5                   10                  15

Thr Ile Lys Val Thr Gly Leu Ala Gln Val Leu Leu Gln Trp Lys Pro
            20                  25                  30
```

```
Asn Pro Asp Gln Glu Gln Arg Asn Val Asn Leu Glu Tyr Gln Val Lys
         35                  40                  45

Ile Asn Ala Pro Lys Glu Asp Tyr Glu Thr Arg Ile Thr Glu Ser
 50                  55                  60

Lys Cys Val Thr Ile Leu His Lys Gly Phe Ser Ala Ser Val Arg Thr
 65                  70                  75                  80

Ile Leu Gln Asn Asp His Ser Leu Leu Ala Ser Ser Trp Ala Ser Ala
                 85                  90                  95

Glu Leu His Ala Pro Pro Gly Ser Pro Gly Thr Ser Ile Val Asn Leu
            100                 105                 110

Thr Cys Thr Thr Asn Thr Thr Glu Asp Asn Tyr Ser Arg Leu Arg Ser
            115                 120                 125

Tyr Gln Val Ser Leu His Cys Thr Trp Leu Val Gly Thr Asp Ala Pro
        130                 135                 140

Glu Asp Thr Gln Tyr Phe Leu Tyr Tyr Arg Tyr Gly Ser Trp Thr Glu
145                 150                 155                 160

Glu Cys Gln Glu Tyr Ser Lys Asp Thr Leu Gly Arg Asn Ile Ala Cys
                165                 170                 175

Trp Phe Pro Arg Thr Phe Ile Leu Ser Lys Gly Arg Asp Trp Leu Ala
            180                 185                 190

Val Leu Val Asn Gly Ser Ser Lys His Ser Ala Ile Arg Pro Phe Asp
        195                 200                 205

Gln Leu Phe Ala Leu His Ala Ile Asp Gln Ile Asn Pro Pro Leu Asn
    210                 215                 220

Val Thr Ala Glu Ile Glu Gly Thr Arg Leu Ser Ile Gln Trp Glu Lys
225                 230                 235                 240

Pro Val Ser Ala Phe Pro Ile His Cys Phe Asp Tyr Glu Val Lys Ile
                245                 250                 255

His Asn Thr Arg Asn Gly Tyr Leu Gln Ile Glu Lys Leu Met Thr Asn
            260                 265                 270

Ala Phe Ile Ser Ile Ile Asp Asp Leu Ser Lys Tyr Asp Val Gln Val
        275                 280                 285

Arg Ala Ala Val Ser Ser Met Cys Arg Glu Ala Gly Leu Trp Ser Glu
290                 295                 300

Trp Ser Gln Pro Ile Tyr Val Gly Asn Asp Glu His Lys Pro Leu Arg
305                 310                 315                 320

Glu Trp Phe Val Ile Val Met Ala Thr Ile Cys Phe Ile Leu Leu
                325                 330                 335

Ile Leu Ser Leu Ile Cys Lys Ile Cys His Leu Trp Ile Lys Leu Phe
            340                 345                 350

Pro Pro Ile Pro Ala Pro Lys Ser Asn Ile Lys Asp Leu Phe Val Thr
        355                 360                 365

Thr Asn Tyr Glu Lys Ala Gly Ser Ser Glu Thr Glu Ile Glu Val Ile
    370                 375                 380

Cys Tyr Ile Glu Lys Pro Gly Val Glu Thr Leu Glu Asp Ser Val Phe
385                 390                 395                 400

<210> SEQ ID NO 13
<211> LENGTH: 881
<212> TYPE: PRT
<213> ORGANISM: Homo Sapien

<400> SEQUENCE: 13

Trp Glu Arg Ser Leu Ala Gly Ala Glu Glu Thr Ile Pro Leu Gln Thr
 1               5                  10                  15
```

-continued

```
Leu Arg Cys Tyr Asn Asp Tyr Thr Ser His Ile Thr Cys Arg Trp Ala
            20                  25                  30

Asp Thr Gln Asp Ala Gln Arg Leu Val Asn Val Thr Leu Ile Arg Arg
        35                  40                  45

Val Asn Glu Asp Leu Leu Glu Pro Val Ser Cys Asp Leu Ser Asp Asp
 50                  55                  60

Met Pro Trp Ser Ala Cys Pro His Pro Arg Cys Val Pro Arg Arg Cys
 65                  70                  75                  80

Val Ile Pro Cys Gln Ser Phe Val Val Thr Asp Val Asp Tyr Phe Ser
                85                  90                  95

Phe Gln Pro Asp Arg Pro Leu Gly Thr Arg Leu Thr Val Thr Leu Thr
            100                 105                 110

Gln His Val Gln Pro Pro Glu Pro Arg Asp Leu Gln Ile Ser Thr Asp
        115                 120                 125

Gln Asp His Phe Leu Leu Thr Trp Ser Val Ala Leu Gly Ser Pro Gln
130                 135                 140

Ser His Trp Leu Ser Pro Gly Asp Leu Glu Phe Glu Val Val Tyr Lys
145                 150                 155                 160

Arg Leu Gln Asp Ser Trp Glu Asp Ala Ala Ile Leu Leu Ser Asn Thr
                165                 170                 175

Ser Gln Ala Thr Leu Gly Pro Glu His Leu Met Pro Ser Ser Thr Tyr
            180                 185                 190

Val Ala Arg Val Arg Thr Arg Leu Ala Pro Gly Ser Arg Leu Ser Gly
        195                 200                 205

Arg Pro Ser Lys Trp Ser Pro Glu Val Cys Trp Asp Ser Gln Pro Gly
210                 215                 220

Asp Glu Ala Gln Pro Gln Asn Leu Glu Cys Phe Phe Asp Gly Ala Ala
225                 230                 235                 240

Val Leu Ser Cys Ser Trp Glu Val Arg Lys Glu Val Ala Ser Ser Val
                245                 250                 255

Ser Phe Gly Leu Phe Tyr Lys Pro Ser Pro Asp Ala Gly Glu Glu Glu
            260                 265                 270

Cys Ser Pro Val Leu Arg Glu Gly Leu Gly Ser Leu His Thr Arg His
        275                 280                 285

His Cys Gln Ile Pro Val Pro Asp Pro Ala Thr His Gly Gln Tyr Ile
290                 295                 300

Val Ser Val Gln Pro Arg Arg Ala Glu Lys His Ile Lys Ser Ser Val
305                 310                 315                 320

Asn Ile Gln Met Ala Pro Pro Ser Leu Asn Val Thr Lys Asp Gly Asp
                325                 330                 335

Ser Tyr Ser Leu Arg Trp Glu Thr Met Lys Met Arg Tyr Glu His Ile
            340                 345                 350

Asp His Thr Phe Glu Ile Gln Tyr Arg Lys Asp Thr Ala Thr Trp Lys
        355                 360                 365

Asp Ser Lys Thr Glu Thr Leu Gln Asn Ala His Ser Met Ala Leu Pro
370                 375                 380

Ala Leu Glu Pro Ser Thr Arg Tyr Trp Ala Arg Val Arg Val Arg Thr
385                 390                 395                 400

Ser Arg Thr Gly Tyr Asn Gly Ile Trp Ser Glu Trp Ser Glu Ala Arg
                405                 410                 415

Ser Trp Asp Thr Glu Ser Val Leu Pro Met Trp Val Leu Ala Leu Ile
            420                 425                 430
```

-continued

Val Ile Phe Leu Thr Ile Ala Val Leu Leu Ala Leu Arg Phe Cys Gly
            435                 440                 445

Ile Tyr Gly Tyr Arg Leu Arg Arg Lys Trp Glu Glu Lys Ile Pro Asn
450                 455                 460

Pro Ser Lys Ser His Leu Phe Gln Asn Gly Ser Ala Glu Leu Trp Pro
465                 470                 475                 480

Pro Gly Ser Met Ser Ala Phe Thr Ser Gly Ser Pro Pro His Gln Gly
                485                 490                 495

Pro Trp Gly Ser Arg Phe Pro Glu Leu Glu Gly Val Phe Pro Val Gly
                500                 505                 510

Phe Gly Asp Ser Glu Val Ser Pro Leu Thr Ile Glu Asp Pro Lys His
                515                 520                 525

Val Cys Asp Pro Pro Ser Gly Pro Asp Thr Thr Pro Ala Ala Ser Asp
    530                 535                 540

Leu Pro Thr Glu Gln Pro Pro Ser Pro Gln Pro Gly Pro Pro Ala Ala
545                 550                 555                 560

Ser His Thr Pro Glu Lys Gln Ala Ser Ser Phe Asp Phe Asn Gly Pro
                565                 570                 575

Tyr Leu Gly Pro Pro His Ser Arg Ser Leu Pro Asp Ile Leu Gly Gln
                580                 585                 590

Pro Glu Pro Pro Gln Glu Gly Gly Ser Gln Lys Ser Pro Pro Pro Gly
            595                 600                 605

Ser Leu Glu Tyr Leu Cys Leu Pro Ala Gly Gly Gln Val Gln Leu Val
            610                 615                 620

Pro Leu Ala Gln Ala Met Gly Pro Gly Gln Ala Val Glu Val Glu Arg
625                 630                 635                 640

Arg Pro Ser Gln Gly Ala Ala Gly Ser Pro Ser Leu Glu Ser Gly Gly
                645                 650                 655

Gly Pro Ala Pro Pro Ala Leu Gly Pro Arg Val Gly Gly Gln Asp Gln
            660                 665                 670

Lys Asp Ser Pro Val Ala Ile Pro Met Ser Ser Gly Asp Thr Glu Asp
            675                 680                 685

Pro Gly Val Ala Ser Gly Tyr Val Ser Ser Ala Asp Leu Val Phe Thr
690                 695                 700

Pro Asn Ser Gly Ala Ser Ser Val Ser Leu Val Pro Ser Leu Gly Leu
705                 710                 715                 720

Pro Ser Asp Gln Thr Pro Ser Leu Cys Pro Gly Leu Ala Ser Gly Pro
                725                 730                 735

Pro Gly Ala Pro Gly Pro Val Lys Ser Gly Phe Glu Gly Tyr Val Glu
            740                 745                 750

Leu Pro Pro Ile Glu Gly Arg Ser Pro Arg Ser Pro Arg Asn Asn Pro
            755                 760                 765

Val Pro Pro Glu Ala Lys Ser Pro Val Leu Asn Pro Gly Glu Arg Pro
    770                 775                 780

Ala Asp Val Ser Pro Thr Ser Pro Gln Pro Glu Gly Leu Leu Val Leu
785                 790                 795                 800

Gln Gln Val Gly Asp Tyr Cys Phe Leu Pro Gly Leu Gly Pro Gly Pro
                805                 810                 815

Leu Ser Leu Arg Ser Lys Pro Ser Ser Pro Gly Pro Gly Pro Glu Ile
                820                 825                 830

Lys Asn Leu Asp Gln Ala Phe Gln Val Lys Lys Pro Pro Gly Gln Ala
            835                 840                 845

Val Pro Gln Val Pro Val Ile Gln Leu Phe Lys Ala Leu Lys Gln Gln

-continued

```
            850                 855                 860
Asp Tyr Leu Ser Leu Pro Pro Trp Glu Val Asn Lys Pro Gly Glu Val
865                 870                 875                 880
Cys
```